(12) United States Patent
Kesteleyn et al.

(10) Patent No.: US 10,786,484 B2
(45) Date of Patent: *Sep. 29, 2020

(54) MONO- OR DI-SUBSTITUTED INDOLE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Berlare (BE); Jean-François Bonfanti, Ande (FR); Tim Hugo Maria Jonckers, Heist-op-den-Berg (BE); Pierre Jean-Marie Bernard Raboisson, Rosieres (BE); Dorothée Alice Marie-Eve Bardiot, Heverlee (BE); Arnaud Didier M Marchand, Bierbeek (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/759,844

(22) PCT Filed: Sep. 15, 2016

(86) PCT No.: PCT/EP2016/071852

§ 371 (c)(1),
(2) Date: Mar. 14, 2018

(87) PCT Pub. No.: WO2017/046258

PCT Pub. Date: Mar. 23, 2017

(65) Prior Publication Data

US 2018/0256544 A1 Sep. 13, 2018

(30) Foreign Application Priority Data

Sep. 16, 2015 (EP) .................................... 15185522
Apr. 1, 2016 (EP) .................................... 16163465

(51) Int. Cl.
*C07D 209/12* (2006.01)
*A61K 31/404* (2006.01)
*A61P 31/14* (2006.01)

(52) U.S. Cl.
CPC ............ *A61K 31/404* (2013.01); *A61P 31/14* (2018.01); *C07D 209/12* (2013.01); *Y02A 50/385* (2018.01)

(58) Field of Classification Search
CPC .................................................. C07D 209/12
See application file for complete search history.

(56) References Cited

U.S. PATENT DOCUMENTS

| 7,601,735 | B2 | 10/2009 | Tyms et al. |
| 8,324,217 | B2 | 12/2012 | Colburn et al. |
| 8,524,764 | B2 | 9/2013 | Canales et al. |
| 8,884,030 | B2 | 11/2014 | Canales et al. |
| 8,993,604 | B2 | 3/2015 | Byrd et al. |
| 9,029,376 | B2 | 5/2015 | Byrd et al. |
| 9,522,923 | B2 | 12/2016 | Richards et al. |
| 9,944,598 | B2 * | 4/2018 | Kesteleyn ............ C07D 209/14 |
| 10,029,984 | B2 * | 7/2018 | Kesteleyn ............ C07D 209/14 |
| 10,064,870 | B2 | 9/2018 | Rajagopalan et al. |
| 10,071,961 | B2 * | 9/2018 | Vandyck .............. C07D 405/12 |
| 10,117,850 | B2 * | 11/2018 | Griffioen .............. C07D 403/12 |
| 10,206,902 | B2 | 2/2019 | Kesteleyn et al. |
| 10,323,026 | B2 | 6/2019 | Ikeda et al. |
| 2005/0239821 | A1 | 10/2005 | Neyts et al. |
| 2006/0194835 | A1 | 8/2006 | Dugourd et al. |
| 2006/0211698 | A1 | 9/2006 | Botyanszki et al. |
| 2008/0318338 | A1 | 12/2008 | Kamal et al. |
| 2016/0297810 | A1 | 10/2016 | Bardiot et al. |
| 2017/0002006 | A1 | 1/2017 | Corte et al. |
| 2017/0096429 | A1 | 4/2017 | Corte et al. |
| 2017/0281633 | A1 | 10/2017 | Boylan et al. |
| 2017/0281766 | A1 | 10/2017 | Wiltzius |
| 2017/0283500 | A1 | 10/2017 | Wiltzius et al. |
| 2017/0298017 | A1 | 10/2017 | Kesteleyn et al. |
| 2018/0256545 | A1 | 9/2018 | Kesteleyn et al. |
| 2018/0346419 | A1 | 12/2018 | Kesteleyn et al. |
| 2019/0104738 | A1 | 4/2019 | Narine et al. |
| 2019/0112266 | A1 | 4/2019 | Kesteleyn et al. |
| 2019/0183931 | A1 | 6/2019 | Bakker et al. |

FOREIGN PATENT DOCUMENTS

| WO | 02089780 A2 | 11/2002 |
| WO | 03050295 A2 | 6/2003 |
| WO | 2009149054 A1 | 12/2009 |
| WO | 2010027500 A1 | 3/2010 |
| WO | 2011037643 A2 | 3/2011 |
| WO | 2011088303 A1 | 7/2011 |
| WO | WO 2013/045516 A1 | 4/2013 |
| WO | 2016050841 A1 | 4/2016 |
| WO | 2016053455 A1 | 4/2016 |
| WO | 2017079216 A1 | 5/2017 |

(Continued)

OTHER PUBLICATIONS

Prasad L. Polavarapu, et al., Intrinsic Rotation and Molecular Structure, Chirality 15: S143-S149 (2003).

(Continued)

*Primary Examiner* — Golam M Shameem
(74) *Attorney, Agent, or Firm* — Amster, Rothstein & Ebenstein LLP

(57) ABSTRACT

The present invention concerns mono- or di-substituted indole compounds, methods to prevent or treat dengue viral infections by using said compounds and also relates to said compounds for use as a medicine, more preferably for use as a medicine to treat or prevent dengue viral infections.

The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

17 Claims, No Drawings
Specification includes a Sequence Listing.

(56) References Cited

FOREIGN PATENT DOCUMENTS

| WO | 2017167832 A1 | 10/2017 |
|---|---|---|
| WO | 2017167950 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 A1 | 10/2017 |
| WO | 2018178238 A1 | 10/2018 |
| WO | 2018178240 A1 | 10/2018 |
| WO | 2018215315 A1 | 11/2018 |
| WO | 2018215316 A1 | 11/2018 |

OTHER PUBLICATIONS

Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.
Boltromeyuk V.V., Obshchaya khimiya (General Chemistry), Minsk, Vysheyshaya shkola, 2012, p. 65) (translation).
Banker, et al., (1996) Modern Pharmaceuticals, 3rd Edition, Revised and Expanded, p. 596.
Wolff et al., Burger's Medicinal Chemistry and Drug Discovery, 5th Ed. part 1, p. 975-977 (1995).
Prevention, Dengue, Centers for Disease Control and Prevention (Sep. 27, 2012) https://www.cdc.govidengue/prevention/index.html, internet.
Lidia Moreira Lima et al., Bioisosterism: A Useful Strategy for Molecular Modification and Drug Design, Current Medicinal Chemistry, Bentham Science Publishers Ltd. (2005) 12, pp. 23-49.
N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nih.gov/bioassay/540276.
EP Search Report dated Nov. 19, 2019 from EP 19183201.3.
"Solvation," Wikipedia, at internet address: https://en.wikipedia.org/wiki/Solvation, web page last edited on Mar. 13, 2019, 6 pages.
Examination Report dated Jan. 7, 2020 from Indian Patent Appln. No. 201727014547.
Japanese Office Action dated Jun. 2, 2020 from Japanese Patent Appln. No. JP2017-243354 (English language translation).
ACS on STN Registry No. 931079-09-3, Apr. 20, 2007.
ACS on STN Registry No. 931007-71-5, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.
ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.
International Search Report dated Nov. 25, 2016 from International Patent Appln. No. PCT/EP2016/071852.
Written Opinion dated Nov. 25, 2016 from International Patent Appln. No. PCT/EP2016/071852.

\* cited by examiner

MONO- OR DI-SUBSTITUTED INDOLE DERIVATIVES AS DENGUE VIRAL REPLICATION INHIBITORS

This application is a national stage application of PCT/EP2016/071852, filed 15 Sep. 2016, which claims priority benefit of Application No. EP15185522.8 filed 16 Sep. 2015 and EP16163465.3 filed 1 Apr. 2016. The complete disclosures of the aforementioned related patent applications are hereby incorporated herein by reference for all purposes.

The present invention relates to mono- or di-substituted indole derivatives, methods to prevent or treat dengue viral infections by using these compounds and also relates to these compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of these compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control the disease associated with dengue viral infection, the only available methods at present are mosquito eradication strategies to control the vector. Although progress is being made in the development of vaccines against dengue, many difficulties are encountered. These include the existence of a phenomenon referred to as antibody-dependent enhancement (ADE).

Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Recently (December 2015), the dengue vaccine produced by Sanofi Pasteur was first approved in Mexico. The vaccine has also been approved in Brazil, The Philippines and El Salvador. Regulatory review processes are continuing in other countries where dengue is a public health priority. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

The present invention now provides compounds, mono- or di-substituted indole derivatives, which show high potent activity against all four (4) serotypes of the Dengue virus. Also the compounds according to the invention possess a good pharmacokinetic profile and surprisingly these specific compounds show an improved chiral stability.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision of compounds of formula (I)

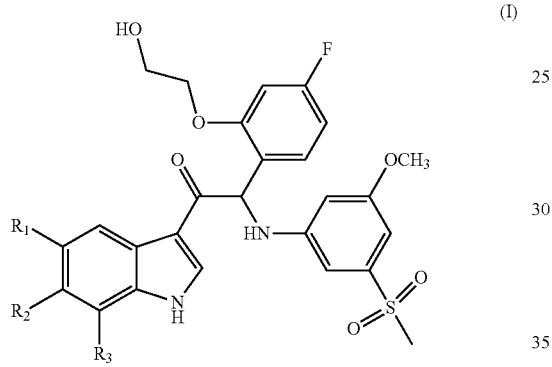

(I)

a stereo-isomeric form, a pharmaceutically acceptable salt, solvate or polymorph thereof comprising a mono- or di-substituted indole group; said compound is selected from the group wherein:
$R_1$ is H, $R_2$ is F or Cl and $R_3$ is H or $CH_3$;
$R_1$ is F, $R_2$ is F and $R_3$ is H;
$R_1$ is $CH_3$, $R_2$ is $OCH_3$ and $R_3$ is H;
$R_1$ is $CH_3$, $R_2$ is F and $R_3$ is H;
$R_1$ is $CH_3$, $R_2$ is H and $R_3$ is F;
$R_1$ is Cl, $R_2$ is H and $R_3$ is $CH_3$;
$R_1$ is $OCF_3$, $R_2$ is H or $OCH_3$ and $R_3$ is H and
$R_1$ is $OCF_3$, $R_2$ is H and $R_3$ is $CH_3$.

In particular the compounds of the invention or their stereo-isomeric form, a pharmaceutically acceptable salt, solvate or polymorph thereof are selected from the group:

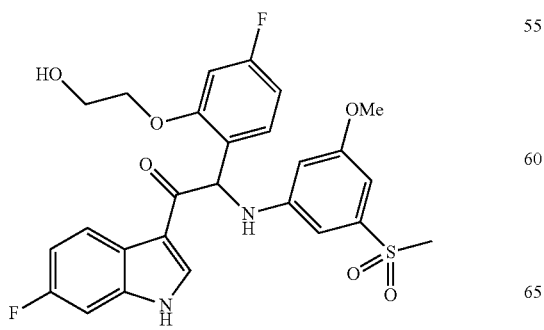

-continued

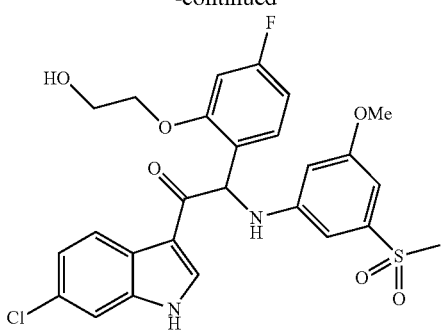

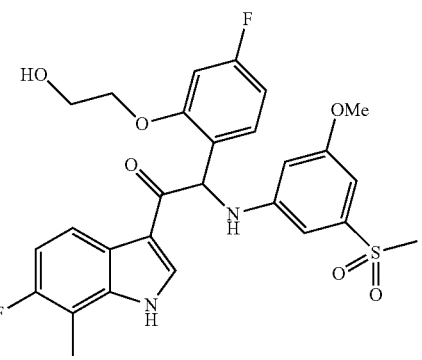

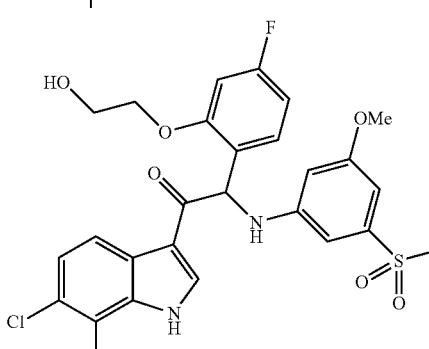

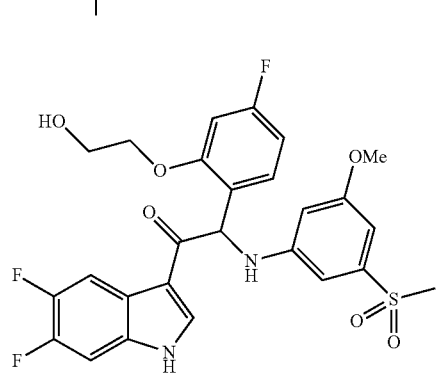

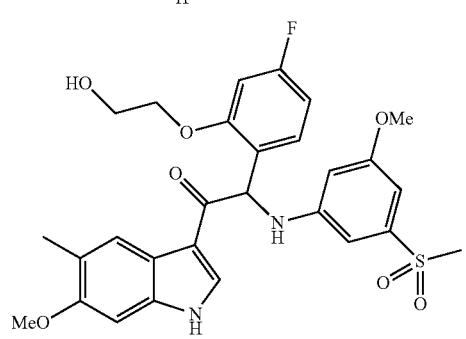

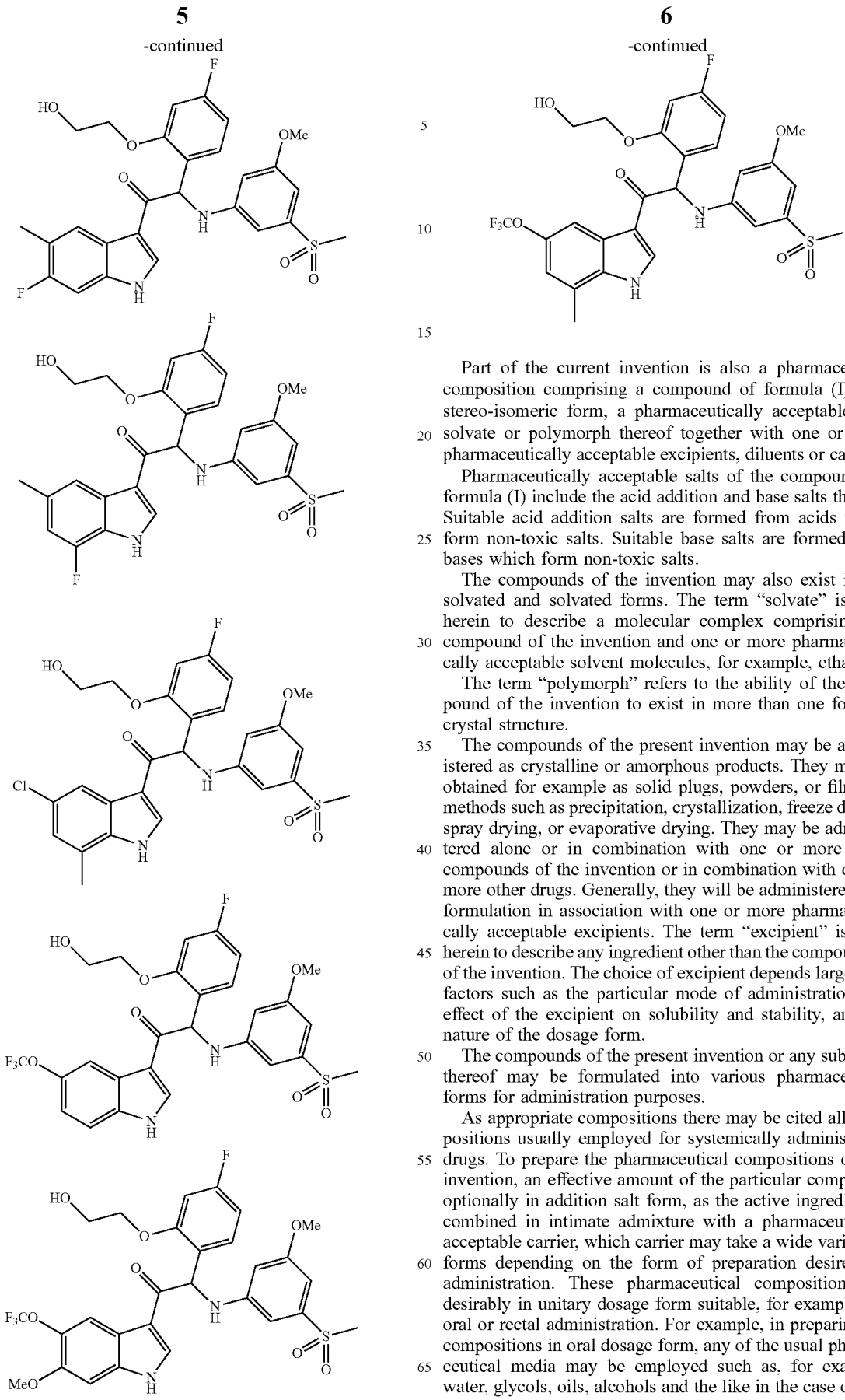

Part of the current invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes.

As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess.

Said mixture may contain all dia-stereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

General Synthetic Approaches

The synthesis of compounds of general formula I can be performed as outlined in Scheme 1. A 2-(4-fluoro-2-(2-hydroxyethoxy)phenyl)acetic acid derivative of general formula II, containing a O-protecting group PG of the hydroxyl function (PG may be for example an O-benzyl protecting group), can be converted to the corresponding acid chloride derivative of general formula III with a chlorination reagent like for example oxalyl chloride or thionyl chloride. The Friedel-Crafts reaction of the acid chloride of general formula III with a substituted indole of general formula IV can be performed using a Lewis acid reagent like for example $Et_2AlCl$ in a suitable solvent like for example $CH_2Cl_2$, and under suitable reaction conditions that typically involve cooling, to provide the 3-acylated indole of general formula V. Removal of the protecting group PG from the compounds of general formula V can be performed by for example reductive hydrogenolysis (PG=benzyl) in a suitable solvent like for example EtOAc, to provide the compounds of general formula VI. The introduction of an aniline moiety in alpha position to the carbonyl moiety of the compounds of general formula VI can be accomplished by a reaction sequence that involves for example bromination of VI with a reagent like for example phenyltrimethylammonium tribromide in a suitable solvent like for example THF, to provide the compounds of general formula VII, and subsequent reaction of the compounds of general formula VII with 3-methoxy-5-(methyl-sulfonyl)aniline (VIII) in a suitable solvent like for example $CH_3CN$, and optionally using a base like for example TEA or DIPEA, to provide the compounds of general formula I as racemic mixtures. Chiral separation of the compounds of general formula I can be performed by for example chiral chromatography to provide the Enantiomers A and B of general formula I.

Scheme 1

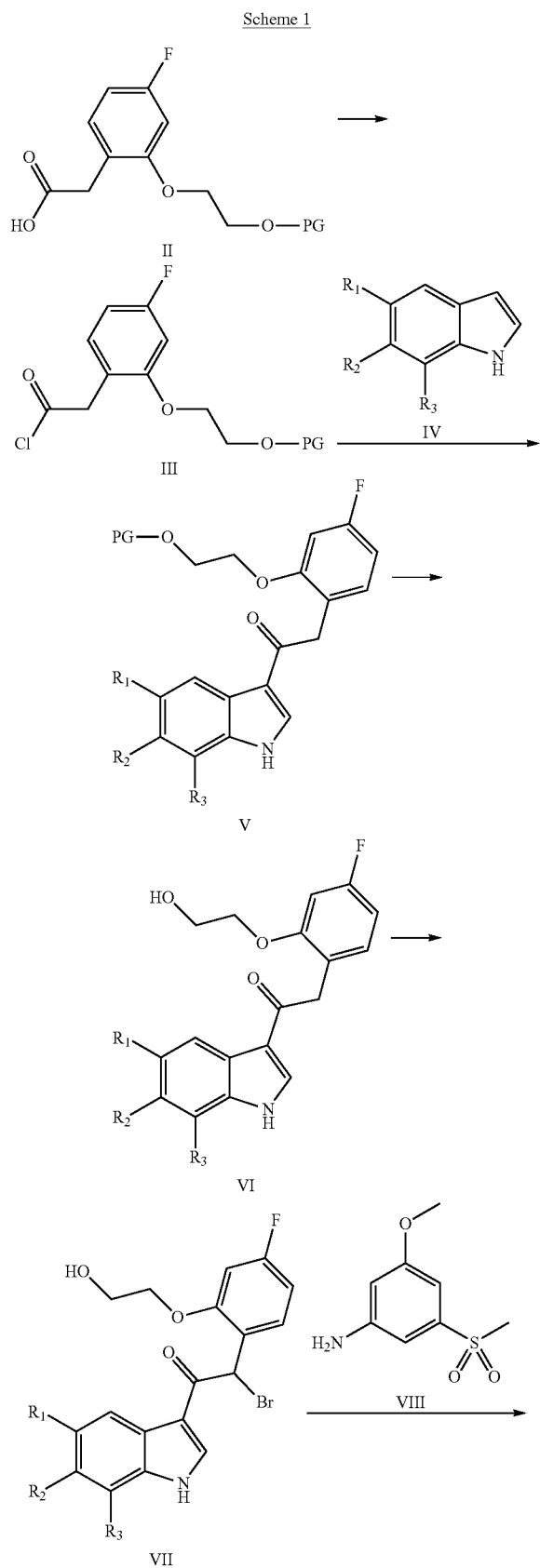

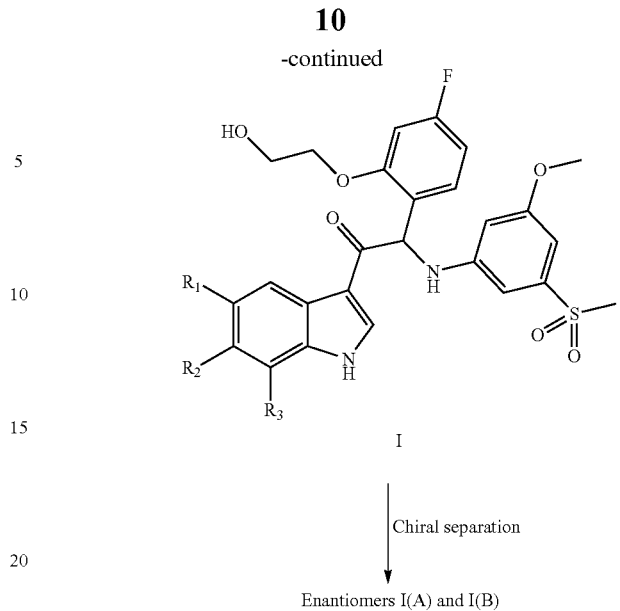

Alternatively, the conversion of the intermediates of general formula V to the Compounds of general formula I can also be accomplished by the reaction sequence outlined in Scheme 2: bromination at the alpha position of the carbonyl function of the intermediates of general formula V with a suitable bromination reagent such as for example phenyltrimethylammonium tribromide in a suitable solvent like for example THF, provides the compounds of general formula IX. Subsequent reaction of the compounds of general formula IX with 3-methoxy-5-(methylsulfonyl)aniline (VIII) in a suitable solvent like for example $CH_3CN$, and optionally using a base like for example TEA or DIPEA, provides the compounds of general formula X. After removal of the O-protecting group (PG) from the compounds of general formula X by for example reductive hydrogenolysis (PG=benzyl) in suitable solvent like for example EtOAc or MeOH, the compounds of general formula I are generated as racemic mixtures. The chiral separation of the compounds of general formula I can be performed by for example chiral chromatography to provide the Enantiomers A and B of general formula I.

Scheme 2

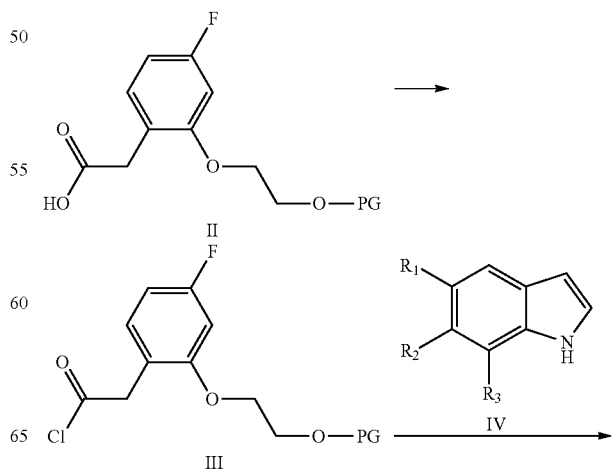

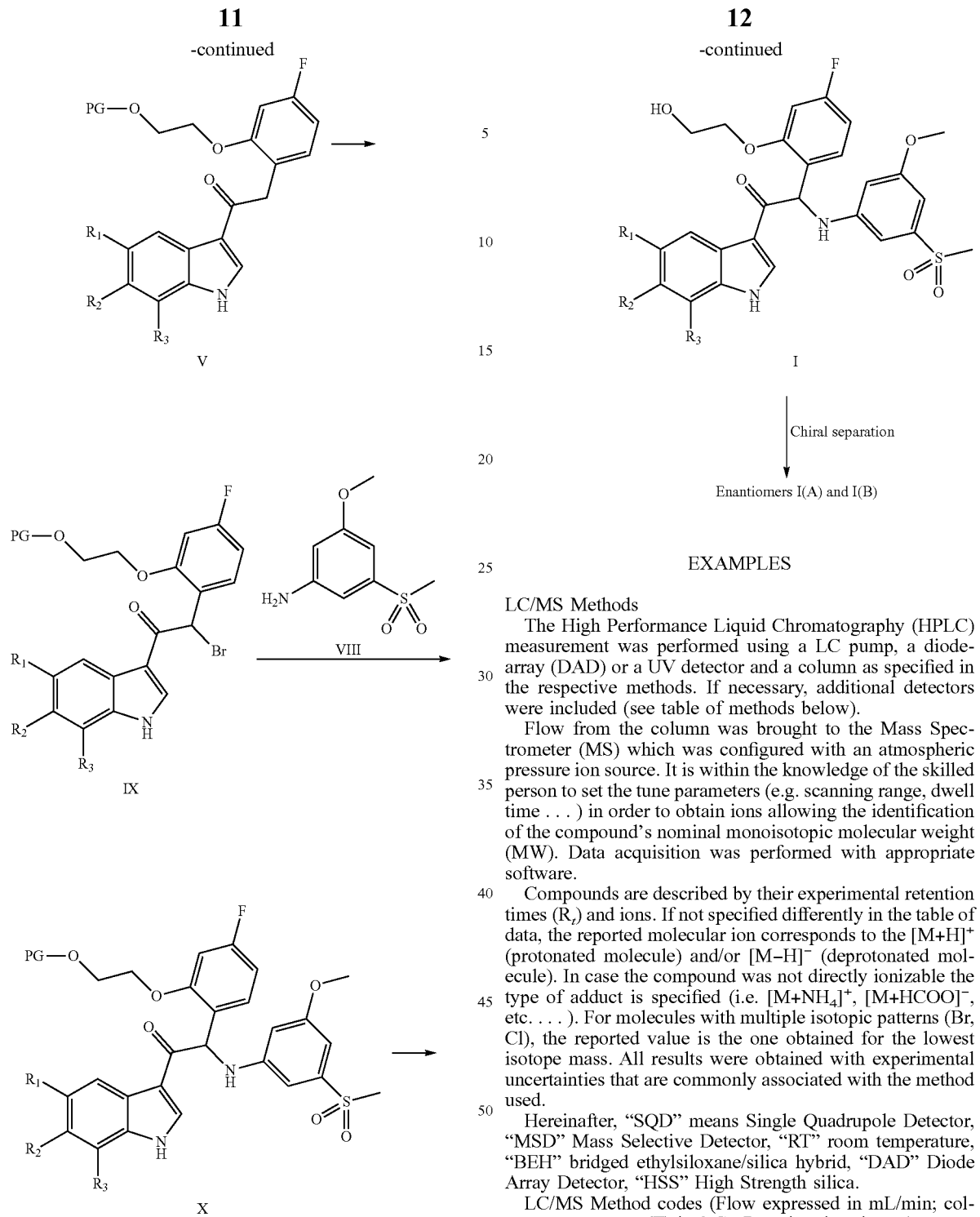

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes)

| Method code | Instrument | Column | Mobile phase | Gradient | Flow Col T | Run time (min) |
|---|---|---|---|---|---|---|
| LC-A | Waters: Acquity ® UPLC ® - DAD-SQD | Waters: BEH C18 (1.7 µm, 2.1 × 50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 mL/min 55° C. | 2 |

-continued

| Method code | Instrument | Column | Mobile phase | Gradient | Flow Col T | Run time (min) |
|---|---|---|---|---|---|---|
| LC-B | Waters: Acquity ® UPLC ® - DAD-SQD | Waters: HSS T3 (1.8 µm, 2.1 × 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 mL/min 55° C. | 3.5 |
| LC-C | Waters: Acquity ® UPLC ® - DAD-Quattro Micro ™ | Waters: BEH C18 (1.7 µm, 2.1 × 100 mm) | A: 95% $CH_3COONH_4$ 7 mM/5% $CH_3CN$ B: $CH_3CN$ | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-D | Waters: Acquity ® UPLC ® - DAD-Acquity ® TQ detector | Waters: BEH C18 (1.7 µm, 2.1 × 50 mm) | A: 10 mM $CH_3COONH_4$, pH 10 B: $CH_3CN$ | 80% A to 40% A in 3.4 min, to 10% A in 0.6 min, held for 1 min. | 0.5 mL/min 40° C. | 5 |
| LC-E | Waters: Acquity ® UPLC ® - DAD-Acquity ®TQ detector | Waters: BEH C18 (1.7 µm, 2.1 × 50 mm) | A: 10 mM $CH_3COONH_4$, pH 10 B: $CH_3CN$ | 50% A to 10% A in 3.5 min, held for 1.5 min. | 0.5 mL/min 40° C. | 5 |
| LC-F | Waters: Acquity ® UPLC ® - DAD-Acquity ® TQ detector | Waters: HSS C18 (1.8 µm, 2.1 × 50 mm) | A: 0.1% Formic acid in $H_2O$ B: $CH_3CN$ | 50% A to 10% A in 3.5 min, held for 1.5 min. | 0.5 mL/min 40° C. | 5 |
| LC-G | Waters: Acquity ® H-Class - DAD and SQD2 ™ | Waters: BEH C18 (1.7 µm, 2.1 × 100 mm) | A: 95% $CH_3COONH_4$ 7 mM/5% $CH_3CN$ B: $CH_3CN$ | 84.2% A/15.8% B to 10.5% A in 2.18 min, held for 1.96 min, back to 84.2% A/15.8% B in 0.73 min, held for 0.49 min. | 0.343 mL/min 40° C. | 6.1 |

SFC/MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| SFC-A | Daicel Chiralpak ® IA column (5 µm, 150 × 4.6 mm) | A: $CO_2$ B: MeOH | 50% B hold 7 min, | 3 35 | 7 100 |
| SFC-B | Daicel Chiralpak ® IC column (5 µm, 150 × 4.6 mm) | A: $CO_2$ B: MeOH + 0.3% $iPrNH_2$ | 30% B hold 7 min, | 3 35 | 7 100 |
| SFC-C | Daicel Chiralcel ® OD-H column (5 µm, 150 × 4.6 mm) | A: $CO_2$ B: EtOH + 0.3% $iPrNH_2$ | 30% B hold 7 min, | 3 35 | 7 100 |
| SFC-D | Daicel Chiralpak ® AS3 column (3.0 µm, 150 × 4.6 mm) | A: $CO_2$ B: EtOH + 0.2% $iPrNH_2$ + 3% $H_2O$ | 25% B hold 6 min, to 50% in 1 min hold 2.5 min | 2.5 40 | 9.5 110 |
| SFC-E | Daicel Chiralpak ® AS3 column (3.0 µm, 150 × 4.6 mm) | A: $CO_2$ B: EtOH + 0.2% $iPrNH_2$ + 3% $H_2O$ | 10%-50% B in 6 min, hold 3.5 min | 2.5 40 | 9.5 110 |

| Method code | column | mobile phase | gradient | Flow Col T | Run time BPR |
|---|---|---|---|---|---|
| SFC-F | Daicel Chiralpak ® AD-H column (5 μm, 140 × 4.6 mm) | A: CO$_2$ B: iPrOH + 0.3% iPrNH$_2$ | 30% B hold 7 min | 3 35 | 7 100 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations

Optical rotations were measured on a Perkin-Elmer 341 polarimeter with a sodium lamp and reported as follows: $[\alpha]°$ ($\lambda$, c g/100 ml, solvent, T° C.). $[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Example 1: Synthesis of 1-(6-fluoro-1H-indol-3-yl)-2-(4-fluoro-2-(2-hydroxyethoxy)-phenyl)-2-((3-methoxy-5-(methylsulfonyl)phenyl)amino)ethanone (Compound 1) and Chiral Separation into Enantiomers 1A and 1B

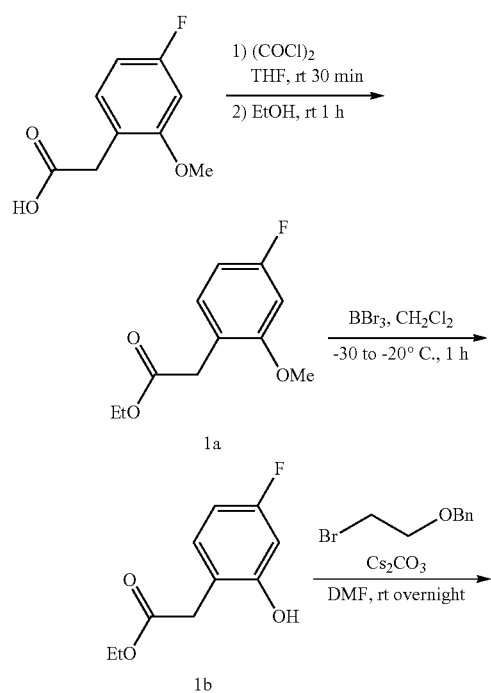

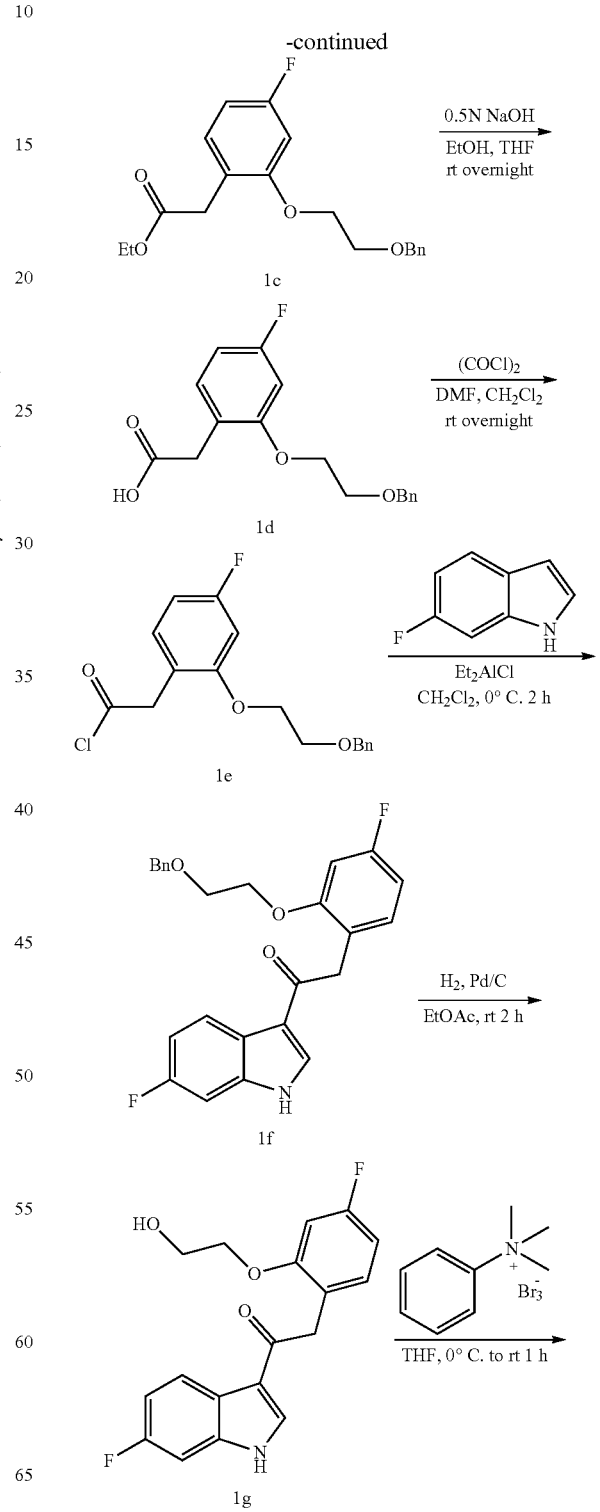

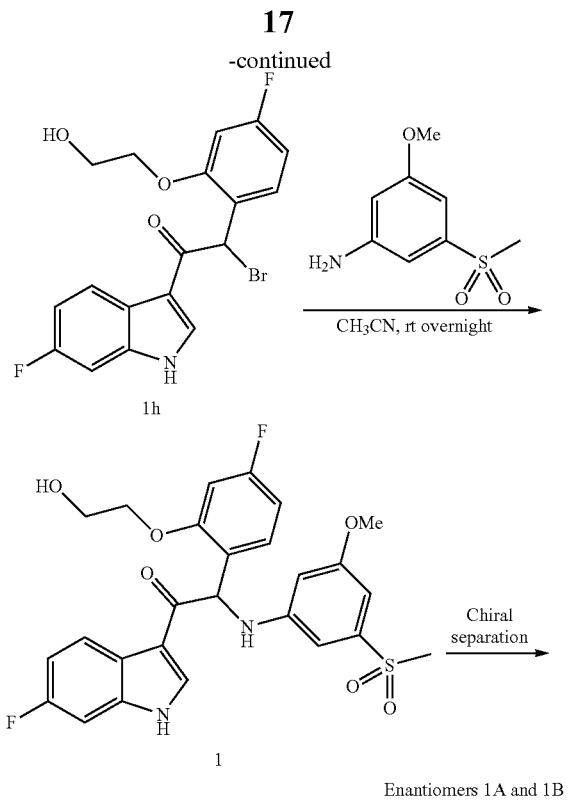

Enantiomers 1A and 1B

Synthesis of Intermediate 1a

A solution of 2-(4-fluoro-2-methoxyphenyl)acetic acid [CAS 886498-61-9] (2.15 g, 11.7 mmol) in dry THF (40 mL) was cooled at 0° C. Oxalyl chloride (2.04 mL, 23.4 mmol) and two drops of DMF were added. The reaction mixture was stirred at room temperature for 30 min. The solvent was evaporated under reduced pressure. The residue was dissolved in ethanol (40 mL) and the reaction mixture was stirred at room temperature for 1 h. The reaction mixture was concentrated under reduced pressure. The residue was purified by flash chromatography on silica gel using a gradient of EtOAc (5% to 50%) in heptane to furnish ethyl 2-(4-fluoro-2-methoxyphenyl)acetate 1a (2.40 g) as an oil.

Synthesis of Intermediate 1b

To a solution of ethyl 2-(4-fluoro-2-methoxyphenyl)acetate 1a (2.40 g, 11.3 mmol) in $CH_2Cl_2$ (110 mL), cooled at −30° C., was added dropwise a 1M $BBr_3$ solution in $CH_2Cl_2$ (22.6 mL, 22.6 mmol) while maintaining the temperature below −20° C. The reaction mixture was stirred at −30° C. for 1 h before quenching with methanol. The pH was adjusted to 8 by addition of an aqueous saturated solution of $NaHCO_3$. The phases were separated. The aqueous phase was extracted with dichloromethane. The organic phases were combined, dried over $Na_2SO_4$, filtered and concentrated under reduced pressure. The residue was purified by flash chromatography on silica gel using a gradient of ethyl acetate (5% to 50%) in heptane to afford ethyl 2-(4-fluoro-2-hydroxyphenyl)acetate 1b (2.10 g) as an oil.

Synthesis of Intermediate 1c

To a mixture of ethyl 2-(4-fluoro-2-hydroxyphenyl)acetate 1b [CAS 1261751-44-3] (1.24 g, 6.26 mmol) and cesium carbonate (4.08 g, 12.5 mmol) in DMF (20 mL) was added benzyl 2-bromoethyl ether [CAS 1462-37-9] (1.61 g, 7.51 mmol). The reaction mixture was stirred at room temperature overnight. $H_2O$ was added and the reaction mixture was extracted with EtOAc. The organic phase was dried over $Na_2SO_4$, filtered and concentrated under reduced pressure. The residue was purified by flash chromatography on silica gel using a gradient of $CH_2Cl_2$ (15% to 100%) in heptane to give ethyl 2-(2-(2-(benzyloxy)ethoxy)-4-fluorophenyl)acetate 1c (1.55 g).

Synthesis of Intermediate 1d

To a solution of ethyl 2-(2-(2-(benzyloxy)ethoxy)-4-fluorophenyl)acetate 1c (1.55 g, 4.66 mmol) in a mixture of EtOH (45 mL) and THF (22 mL) was added 0.5N NaOH (28 mL, 14.0 mmol). The reaction mixture was stirred at room temperature overnight. The reaction mixture was partially concentrated under reduced pressure to remove the organic solvents. The residue was acidified with 1N HCl to pH 2-3 and was extracted with EtOAc. The organic phase was dried over $MgSO_4$, filtered and concentrated under reduced pressure to give 2-(2-(2-(benzyloxy)ethoxy)-4-fluorophenyl)acetic acid 1d (1.41 g).

Synthesis of Intermediate 1e

To a solution of 2-(2-(2-(benzyloxy)ethoxy)-4-fluorophenyl)acetic acid 1d (1.41 g, 4.63 mmol) in dry $CH_2Cl_2$ (20 mL), cooled at 0° C., were added oxalyl chloride (0.811 mL, 9.27 mmol) and DMF (2 drops). The reaction mixture was stirred at room temperature overnight. The reaction mixture was concentrated under reduced pressure to give 2-(2-(2-(benzyloxy)ethoxy)-4-fluorophenyl)acetyl chloride 1e (1.50 g) which was used in the next step without further purification.

Synthesis of Intermediate 1f

Diethylaluminum chloride 1M in hexane (4.72 mL, 4.72 mmol) was added dropwise, at 0° C., to a solution of 6-fluoro-1H-indole [CAS 399-51-9] (0.42 g, 3.11 mmol) in $CH_2Cl_2$ (6 mL). After stirring for 30 min at 0° C., a solution of 2-(2-(2-(benzyloxy)ethoxy)-4-fluorophenyl)acetyl chloride 1e (1.50 g, 4.66 mmol) in dichloromethane (6 mL) was slowly added. The reaction mixture was stirred at 0° C. for 2 h. 1M Rochelle salt solution was added. The reaction mixture was stirred at room temperature for 2 h and was extracted twice with EtOAc. The organic phases were combined, washed with brine, dried over $MgSO_4$, filtered and concentrated under reduced pressure. The residue was purified by flash chromatography on silica gel using a gradient of EtOAc (2% to 40%) in heptane. Further purification by flash chromatography on silica gel using a gradient of EtOAc (0% to 10%) in $CH_2Cl_2$ furnished 2-(2-(2-(benzyloxy)ethoxy)-4-fluorophenyl)-1-(6-fluoro-1H-indol-3-yl)ethanone 1f (0.88 g).

Synthesis of Intermediate 1g

A mixture of 2-(2-(2-(benzyloxy)ethoxy)-4-fluorophenyl)-1-(6-fluoro-1H-indol-3-yl)-ethanone 1f (0.88 g, 2.09 mmol) and 10% palladium on carbon (0.088 g) in EtOAc (90 mL) was stirred at room temperature for 2 h under $H_2$ atmosphere. The reaction mixture was filtered through a pad of Celite® and the filter cake was washed with $CH_2Cl_2$ and MeOH. The combined filtrates were concentrated under reduced pressure. The residue was solidified by trituration with CH$_2$Cl$_2$. The solids were filtered off and dried under vacuum to give 1-(6-fluoro-1H-indol-3-yl)-2-(4-fluoro-2-(2-hydroxyethoxy)phenyl)ethanone 1g (0.59 g).

Synthesis of Intermediate 1h

A solution of phenyltrimethylammonium tribromide [CAS 4207-56-1] (0.70 g, 1.86 mmol) in THF (10 mL) was added dropwise at 0° C. to a solution of 1-(6-fluoro-1H-indol-3-yl)-2-(4-fluoro-2-(2-hydroxyethoxy)phenyl)ethanone 1g (0.56 g, 1.69 mmol) in THF (15 mL). The mixture was stirred at 0° C. for 15 min and at room temperature for 1 h. The precipitate was filtered off and washed with EtOAc. The filtrate was concentrated under reduced pressure to give 2-bromo-1-(6-fluoro-1H-indol-3-yl)-2-(4-fluoro-2-(2-hydroxyethoxy) phenyl)ethanone 1h (0.69 g) which was used without further purification in the next step.

Synthesis of Compound 1 and Chiral Separation into Enantiomers 1A and 1B

A mixture of 2-bromo-1-(6-fluoro-1H-indol-3-yl)-2-(4-fluoro-2-(2-hydroxyethoxy) phenyl)ethanone 1h (0.69 g, 1.69 mmol) and 3-methoxy-5-(methylsulfonyl)aniline [CAS 62606-02-4] (1.02 g, 5.07 mmol) in CH$_3$CN (10 mL) was stirred at room temperature overnight. The reaction mixture was diluted with EtOAc and washed with 1N HCl. The organic layer was washed with an aqueous saturated NaHCO$_3$ solution, H$_2$O and brine, dried over Na$_2$SO$_4$, filtered and concentrated under reduced pressure. The residue was purified by flash chromatography on silica gel using a gradient of EtOAc (15% to 70%) in CH$_2$Cl$_2$. The fractions containing the desired compound were combined and concentrated under reduced pressure. The residue was recrystallized from a mixture of EtOAc, Et$_2$O and heptane to afford a first batch of 1-(6-fluoro-1H-indol-3-yl)-2-(4-fluoro-2-(2-hydroxyethoxy)phenyl)-2-((3-methoxy-5-(methylsulfonyl)phenyl)amino)ethanone (Compound 1, 0.47 g) as a racemic mixture. The filtrate was concentrated under reduced pressure and the residue was recrystallized from a mixture of EtOAc, Et$_2$O and heptane to give a second batch of Compound 1 (0.11 g) as a racemic mixture.

The chiral separation of the Enantiomers of Compound 1 (620 mg) was performed using Normal Phase Chiral separation (Stationary phase: Chiralpak® AD 1000A 20 µm (Daicel) (600 g), Mobile phase: EtOH/MeOH (1/1). The product fractions were combined and evaporated under reduced pressure to provide Enantiomer 1A as the first eluted product and Enantiomer 1B as the second eluted product. Both enantiomers were dissolved in a mixture of water (5 ml)+MeOH (20 ml). The solvent was partially evaporated under reduced pressure (40° C. water bath) to a residual amount of approximately 5 ml. The resulting suspensions were diluted with water (10-15 mL) and vigorously stirred for 2 days. The solids were isolated by filtration and dried under vacuum at room temperature to provide Enantiomer 1A (227 mg) and Enantiomer 1B (251 mg) as white powders.

Compound 1

$^1$H NMR (300 MHz, DMSO-d$_6$) δ ppm 3.08 (s, 3H) 3.72 (s, 3H) 3.87-4.10 (m, 2H) 4.17 (m, 2H) 5.30 (br. s., 1H) 6.36 (d, J=7.8 Hz, 1H) 6.57 (t, J=1.6 Hz, 1H) 6.65 (s, 1H) 6.72 (td, J=8.5, 2.5 Hz, 1H) 6.92-6.96 (m, 2H) 7.03-7.10 (m, 2H) 7.24 (dd, J=9.6, 2.3 Hz, 1H) 7.38 (dd, J=8.6, 6.9 Hz, 1H) 8.16 (dd, J=8.8, 5.6 Hz, 1H) 8.68 (s, 1H) 12.16 (br. s., 1H)

LC/MS (method LC-D): R$_t$ 3.43 min, MH$^+$531

Enantiomer 1A $^1$H NMR (360 MHz, DMSO-d$_6$) δ ppm 3.08 (s, 3H) 3.72 (s, 3H) 3.89-4.07 (m, 2H) 4.18 (t, J=4.7 Hz, 2H) 5.30 (br t, J=5.7 Hz, 1H) 6.35 (d, J=7.8 Hz, 1H) 6.55-6.59 (m, 1H) 6.62-6.67 (m, 1H) 6.71 (br td, J=8.4, 2.6 Hz, 1H) 6.91-6.97 (m, 2H) 7.01-7.09 (m, 2H) 7.24 (dd, J=9.6, 2.4 Hz, 1H) 7.38 (dd, J=8.6, 6.8 Hz, 1H) 8.15 (dd, J=8.9, 5.5 Hz, 1H) 8.68 (s, 1H) 12.16 (brs, 1H)

LC/MS (method LC-B): R$_t$ 1.91 min, MH$^+$ 531

[α]$_D^{20}$: +118.6° (c 0.4335, DMF)

Chiral SFC (method SFC-D): R$_t$ 1.68 min, MH$^+$ 531, chiral purity 100%.

Enantiomer 1B $^1$H NMR (360 MHz, DMSO-d$_6$) δ ppm 3.08 (s, 3H) 3.71 (s, 3H) 3.89-4.06 (m, 2H) 4.17 (br t, J=4.8 Hz, 2H) 5.30 (br t, J=5.2 Hz, 1H) 6.35 (d, J=7.7 Hz, 1H) 6.55-6.59 (m, 1H) 6.62-6.67 (m, 1H) 6.71 (br td, J=8.4, 2.7 Hz, 1H) 6.90-6.97 (m, 2H) 7.02-7.10 (m, 2H) 7.23 (dd, J=9.6, 2.5 Hz, 1H) 7.37 (dd, J=8.6, 6.8 Hz, 1H) 8.15 (dd, J=8.8, 5.5 Hz, 1H) 8.68 (s, 1H) 12.15 (brs, 1H)

LC/MS (method LC-B): R$_t$ 1.91 min, MH$^+$ 531

[α]$_D^{20}$: −115.4° (c 0.3985, DMF)

Chiral SFC (method SFC-D): R$_t$ 2.20 min, MH$^+$ 531, chiral purity 100%.

Example 2: Synthesis of 1-(6-chloro-1H-indol-3-yl)-2-(4-fluoro-2-(2-hydroxyethoxy)-phenyl)-2-((3-methoxy-5-(methylsulfonyl)phenyl)amino)ethanone (Compound 2) and Chiral Separation into Enantiomers 2A and 2B

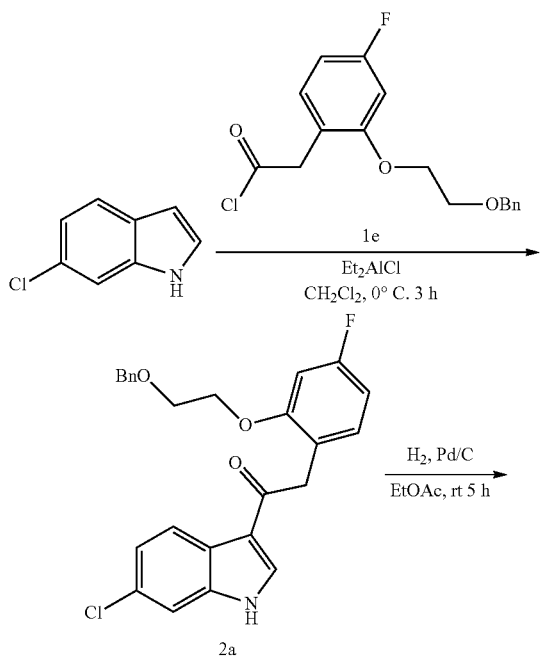

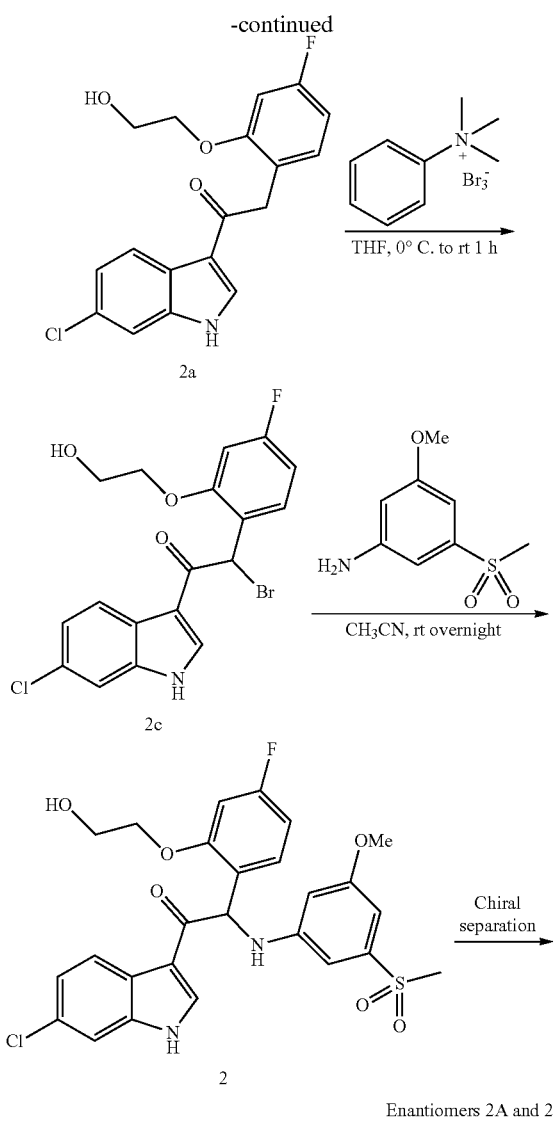

Synthesis of Intermediate 2a

Diethylaluminum chloride 1M in hexane (13.1 mL, 13.1 mmol) was added dropwise, at 0° C., to a solution of 6-chloro-1H-indole [CAS 17422-33-2] (1.33 g, 8.76 mmol) in CH₂Cl₂ (20 mL). After 30 min at 0° C., a solution of 2-(2-(2-(benzyl-oxy)ethoxy)-4-fluorophenyl)acetyl chloride 1e (4.24 g, 13.1 mmol, synthesis: see Example 1) in CH₂Cl₂ (10 mL) was slowly added. The reaction mixture was stirred at 0° C. for 3 h. 1M Rochelle salt solution was added. After 30 min at room temperature, the reaction mixture was diluted with CH₂Cl₂ and washed with 6N HCl. The phases were separated. The organic phase was washed with brine, filtered over a phase separator filter and concentrated under reduced pressure. The residue was purified by flash chromatography on silica gel using a gradient of EtOAc (10% to 80%) in heptane. The fractions containing the desired product were combined and concentrated under reduced pressure. The residue was purified by precipitation from a mixture of EtOAc and heptane to yield 2-(2-(2-(benzyloxy) ethoxy)-4-fluorophenyl)-1-(6-chloro-1H-indol-3-yl)ethanone 2a (2.39 g).

Synthesis of Intermediate 2b

A mixture 2-(2-(2-(benzyloxy)ethoxy)-4-fluorophenyl)-1-(6-chloro-1H-indol-3-yl)-ethanone 2a (2.05 g, 4.68 mmol) and 10% palladium on carbon (0.20 g) in EtOAc (30 mL) was stirred at room temperature for 5 h under H₂ atmosphere. The reaction mixture was filtered through diatomaceous earth and washed with THF. The filtrate was concentrated under reduced pressure. The residue was triturated with EtOAc. The precipitate was filtered off to give 1-(6-chloro-1H-indol-3-yl)-2-(4-fluoro-2-(2-hydroxyethoxy) phenyl)ethanone 2b (1.41 g).

Synthesis of Intermediate 2c

A solution of phenyltrimethylammonium tribromide [CAS 4207-56-1] (1.83 g, 4.87 mmol) in THF (15 mL) was added dropwise, at 0° C., to a solution of 1-(6-chloro-1H-indol-3-yl)-2-(4-fluoro-2-(2-hydroxyethoxy)phenyl)ethanone 2b (1.54 g, 4.43 mmol) in THF (30 mL). The mixture was stirred at room temperature for 1 h. The precipitate was filtered off and washed with THF. The filtrate was concentrated under reduced pressure to give 2-bromo-1-(6-chloro-1H-indol-3-yl)-2-(4-fluoro-2-(2-hydroxyethoxy)phenyl) ethanone 2c (1.89 g) which was used in the next step without further purification.

Synthesis of Compound 2 and Chiral Separation into Enantiomers 2A and 2B

A mixture of 2-bromo-1-(6-chloro-1H-indol-3-yl)-2-(4-fluoro-2-(2-hydroxyethoxy)-phenyl)ethanone 2c (1.89 g, 4.43 mmol) and 3-methoxy-5-(methylsulfonyl)aniline [CAS 62606-02-4] (2.67 g, 13.3 mmol) in CH₃CN (45 mL) was stirred at room temperature overnight. The reaction mixture was concentrated under reduced pressure. The residue was partitioned between EtOAc and 1N HCl. The phases were separated. The organic phase was washed with an aqueous saturated NaHCO₃ solution and brine, dried over MgSO₄, filtered and concentrated under reduced pressure. The residue was purified by flash chromatography on silica gel using a gradient of EtOAc (40% to 100%) in heptane. The fractions containing the desired product were combined and concentrated under reduced pressure. The residue was triturated with a mixture of Et₂O and CH₂Cl₂. The precipitate was filtered off and purified by flash chromatography on silica gel using a gradient of MeOH (1% to 10%) in CH₂Cl₂ to give 1-(6-chloro-1H-indol-3-yl)-2-(4-fluoro-2-(2-hydroxyethoxy)phenyl)-2-((3-methoxy-5-(methylsulfonyl) phenyl)amino)-ethanone (Compound 2, 1.05 g) as a racemic mixture.

The enantiomers of Compound 2 (1.01 g) were separated via Chiral SFC (Stationary phase: Chiralpak® IA 5 μm 20×250 mm, Mobile phase: 50% CO₂, 50% MeOH) yielding 460 mg of the first eluted enantiomer and 424 mg of the second eluted enantiomer. The two fractions were purified again by flash chromatography on silica gel (15-40 μm, 12 g, CH₂Cl₂/MeOH 99.5/0.5). The pure fractions were combined and evaporated to dryness. The residues were solidified by trituration with a mixture of Et₂O and diisopropyl ether. The solids were filtered off and dried to provide 353 mg of the first eluted enantiomer and 363 mg the second eluted enantiomer. The first eluted enantiomer was further purified via achiral SFC (Stationary phase: DEAP (diethylaminopropyl) 5 μm 150×21.2 mm, Mobile phase: 60% CO₂, 40% EtOH (+0.3% iPrNH₂)). The pure fractions were combined and evaporated to dryness and then solidified by trituration with MeOH/water. The precipitate was filtered off, rinsed with diisopropyl ether and dried to give Enantiomer 2A (269 mg). The second eluted enantiomer was further purified via achiral SFC (Stationary phase: DEAP 5 μm 150×21.2 mm, Mobile phase: 60% $CO_2$, 40% EtOH (+0.3% $iPrNH_2$)). The pure fractions were combined and evaporated to dryness and then solidified by trituration with MeOH/water. The precipitate was filtered off, rinsed with diisopropyl ether and dried to give Enantiomer 2B (261 mg).

Compound 2

$^1$H NMR (300 MHz, DMSO-$d_6$) δ ppm 3.10 (s, 3H) 3.74 (s, 3H) 3.86-4.12 (m, 2H) 4.20 (m, 2H) 5.32 (br. s., 1H) 6.38 (d, J=7.7 Hz, 1H) 6.59 (s, 1H) 6.67 (s, 1H) 6.74 (td, J=8.4, 2.2 Hz, 1H) 6.91-7.00 (m, 2H) 7.08 (d, J=7.7 Hz, 1H) 7.24 (dd, J=8.5, 1.7 Hz, 1H) 7.39 (t, J=7.7 Hz, 1H) 7.52 (d, J=1.5 Hz, 1H) 8.18 (d, J=8.5 Hz, 1H) 8.72 (s, 1H) 12.24 (br. s., 1H)

LC/MS (method LC-F): $R_t$ 1.25 min, $MH^+$ 547

Enantiomer 2A $^1$H NMR (500 MHz, DMSO-$d_6$) δ ppm 3.08 (s, 3H) 3.72 (s, 3H) 3.89-4.07 (m, 2H) 4.18 (br t, J=4.3 Hz, 2H) 5.31 (br s, 1H) 6.36 (d, J=7.9 Hz, 1H) 6.57 (s, 1H) 6.65 (br s, 1H) 6.72 (td, J=8.4, 2.0 Hz, 1H) 6.90-6.98 (m, 2H) 7.06 (br d, J=7.9 Hz, 1H) 7.22 (dd, J=8.5, 1.6 Hz, 1H) 7.37 (t, J=7.7 Hz, 1H) 7.50 (d, J=1.3 Hz, 1H) 8.16 (d, J=8.5 Hz, 1H) 8.70 (s, 1H) 12.21 (br s, 1H)

LC/MS (method LC-C): $R_t$ 2.94 min, $MH^+$ 547

$[\alpha]_D^{20}$: +127.6° (c 0.25, DMF)

Chiral SFC (method SFC-A): $R_t$ 2.02 min, $MH^+$ 547, chiral purity 98.22%.

Melting point: 118° C.

Enantiomer 2B $^1$H NMR (500 MHz, DMSO-$d_6$) δ ppm 3.08 (s, 3H) 3.72 (s, 3H) 3.89-4.07 (m, 2H) 4.15-4.20 (m, 2H) 5.31 (br s, 1H) 6.36 (d, J=7.6 Hz, 1H) 6.57 (s, 1H) 6.65 (br s, 1H) 6.72 (td, J=8.4, 2.0 Hz, 1H) 6.89-6.99 (m, 2H) 7.06 (br d, J=7.6 Hz, 1H) 7.22 (dd, J=8.5, 1.3 Hz, 1H) 7.37 (t, J=7.7 Hz, 1H) 7.50 (d, J=1.3 Hz, 1H) 8.16 (d, J=8.5 Hz, 1H) 8.70 (s, 1H) 12.21 (brs, 1H)

LC/MS (method LC-C): $R_t$ 2.94 min, $MH^+$ 547

$[\alpha]_D^{20}$: −125.6° (c 0.2555, DMF)

Chiral SFC (method SFC-A): $R_t$ 2.40 min, $MH^+$ 547, chiral purity 100%.

Melting point: 117° C.

Example 3: Synthesis of 2-(4-fluoro-2-(2-hydroxyethoxy)phenyl)-1-(6-fluoro-7-methyl-1H-indol-3-yl)-2-((3-methoxy-5-(methylsulfonyl)phenyl)amino)ethanone (Compound 3) and Chiral Separation into Enantiomers 3A and 3B

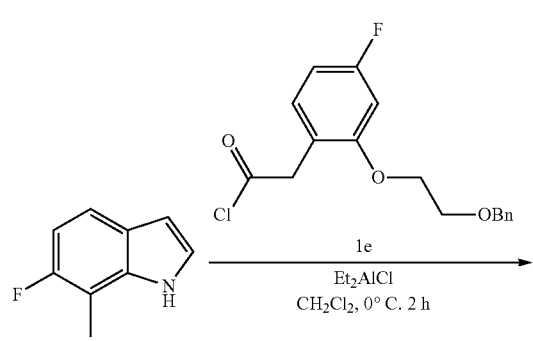

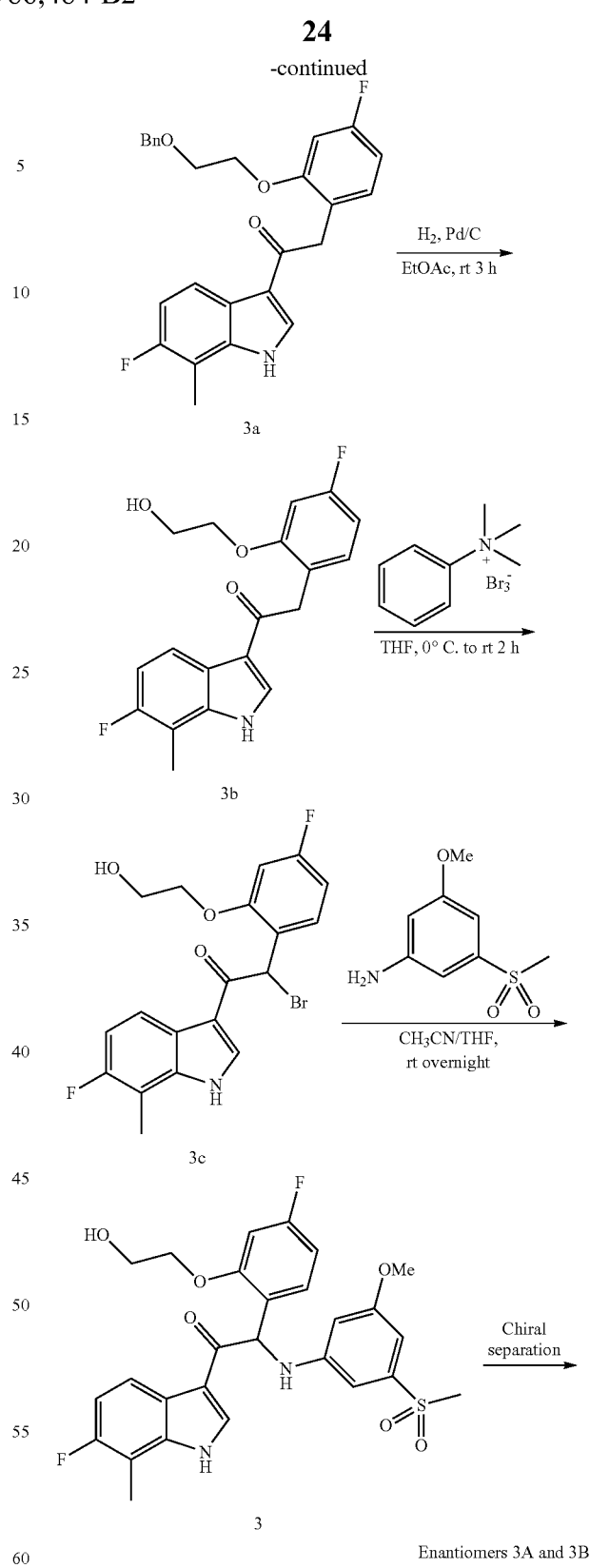

Synthesis of Intermediate 3a

Diethylaluminum chloride 1M in hexane (13.2 mL, 13.2 mmol) was added dropwise, at 0° C., to a solution of 6-fluoro-7-methyl-1H-indole [CAS 57817-10-4] (1.3 g, 8.71 mmol) in $CH_2Cl_2$ (17 mL). After 30 min at 0° C., a solution of 2-(2-(2-(benzyloxy)ethoxy)-4-fluorophenyl)acetyl chloride 1e (4.22 g, 13.1 mmol, synthesis: see Example 1) in dichloromethane (17 mL) was slowly added. The reaction mixture was stirred at 0° C. for 2 h. 1M Rochelle salt solution was added. The reaction mixture was stirred at room temperature for 2 h and extracted twice with EtOAc. The organic phases were combined, washed with brine, dried over $MgSO_4$, filtered and concentrated under reduced pressure. The residue was taken up with a minimum of $CH_2Cl_2$. The precipitate was filtered off, washed with $CH_2Cl_2$ and dried under vacuum to give a first batch of 2-(2-(2-(benzyloxy)ethoxy)-4-fluorophenyl)-1-(6-fluoro-7-methyl-1H-indol-3-yl)ethanone 3a (1.2 g). The filtrate was concentrated under reduced pressure. The residue was purified by flash chromatography on silica gel using a gradient of EtOAc (5% to 50%) in heptane. The fractions containing the product were combined and concentrated under reduced pressure. The residue was triturated with $CH_3CN$. The solids were filtered off, washed with $CH_2Cl_2$ and dried under vacuum to give a second batch of 2-(2-(2-(benzyloxy)ethoxy)-4-fluorophenyl)-1-(6-fluoro-7-methyl-1H-indol-3-yl)ethanone 3a (0.88 g). The filtrate was partially concentrated. The formed solid was filtered off, washed with $CH_2Cl_2$ and dried under vacuum to give a third batch of 2-(2-(2-(benzyloxy)ethoxy)-4-fluorophenyl)-1-(6-fluoro-7-methyl-1H-indol-3-yl)ethanone 3a (0.17 g).

Synthesis of Intermediate 3b

A mixture 2-(2-(2-(benzyloxy)ethoxy)-4-fluorophenyl)-1-(6-fluoro-7-methyl-1H-indol-3-yl)ethanone 3a (1.95 g, 4.48 mmol) and 10% palladium on carbon (0.2 g) in EtOAc (120 mL) was stirred at room temperature for 3 h under $H_2$ atmosphere. The reaction mixture was filtered through a pad of Celite®. The filtrate was concentrated under reduced pressure. The residue was taken up with a minimum of $CH_2Cl_2$. The precipitate was filtered off and dried under vacuum to give 2-(4-fluoro-2-(2-hydroxyethoxy)phenyl)-1-(6-fluoro-7-methyl-1H-indol-3-yl)ethanone 3b (1.27 g).

Synthesis of Intermediate 3c

A solution of phenyltrimethylammonium tribromide [CAS 4207-56-1] (1.77 g, 4.71-mmol) in THF (28 mL) was added dropwise, at 0° C., to a solution of 2-(4-fluoro-2-(2-hydroxyethoxy)phenyl)-1-(6-fluoro-7-methyl-1H-indol-3-yl)ethanone 3b (1.48 g, 4.29 mmol) in THF (40 mL). The reaction mixture was stirred at 0° C. for 15 min and at room temperature for 2 h. The precipitate was filtered off and washed with EtOAc. The filtrate was concentrated under reduced pressure to give 2-bromo-2-(4-fluoro-2-(2-hydroxyethoxy)phenyl)-1-(6-fluoro-7-methyl-1H-indol-3-yl)ethanone 3c (1.82 g) which was used in the next step without further purification.

Synthesis of Compound 3 and Chiral Separation into Enantiomers 3A and 3B

A mixture of 2-bromo-2-(4-fluoro-2-(2-hydroxyethoxy)phenyl)-1-(6-fluoro-7-methyl-1H-indol-3-yl)ethanone 3c (1.16 g, 2.63 mmol) and 3-methoxy-5-(methylsulfonyl)aniline [CAS 62606-02-4] (1.59 g, 7.90 mmol) in $CH_3CN$ (6 mL) and THF (6 mL) was stirred at room temperature overnight. The reaction mixture was diluted with EtOAc and washed with 1N HCl. The phases were separated. The organic phase was washed with 1N HCl, an aqueous saturated $NaHCO_3$ solution, $H_2O$ and brine, dried over $MgSO_4$, filtered and concentrated under reduced pressure. The residue was purified by flash chromatography on silica gel using a gradient of EtOAc (15% to 100%) in $CH_2Cl_2$. The fractions containing the desired compound were combined and concentrated under reduced pressure. The residue was taken up with a minimum of $CH_2Cl_2$. The precipitate was filtered off and dried under vacuum to give a first batch of 2-(4-fluoro-2-(2-hydroxyethoxy)phenyl)-1-(6-fluoro-7-methyl-1H-indol-3-yl)-2-((3-methoxy-5-(methylsulfonyl)phenyl)amino)ethanone (Compound 3, 0.73 g) as a racemic mixture. The filtrate was concentrated under reduced pressure. The residue was triturated with $CH_2Cl_2$ and $CH_3CN$. The solids were filtered off and dried under reduced pressure to provide a second batch of Compound 3 (0.23 g) as a racemic mixture. The filtrate was concentrated under reduced pressure. The residue was purified by flash chromatography on silica gel using a gradient of EtOAc (15% to 100%) in $CH_2Cl_2$. The fractions containing Compound 3 were combined and concentrated under reduced pressure. The residue was triturated with $CH_2Cl_2$. The solids were filtered off and dried under reduced pressure to provide a third batch of Compound 3 (0.20 g) as a racemic mixture.

The chiral separation of the Enantiomers of Compound 3 (1.15 g) was performed using Normal Phase Chiral separation (Stationary phase: AS 20 µm, Mobile phase: 100% MeOH). The product fractions were combined and evaporated to provide Enantiomer 3A as the first eluted product and Enantiomer 3B as the second eluted product. Enantiomer 3A was purified by flash chromatography (Stationary phase: Grace Reveleris® silica 40 g, Mobile phase: heptane/EtOAc/EtOH gradient 100/0/0 to 40/45/15). The fractions containing product were combined and evaporated, and co-evaporated with MeOH. The foamy residue was stirred up in $H_2O$ (8 mL) and MeOH (2.5 mL) was added dropwise. After stirring for 15 minutes, the precipitate was filtered off, washed with $H_2O$/MeOH 3/1 (4×1.5 mL), and dried under vacuum at 50° C. to provide Enantiomer 3A (0.341 g). Enantiomer 3B was purified by flash chromatography (Stationary phase: Grace Reveleris® silica 40 g, Mobile phase: heptane/EtOAc/EtOH gradient 100/0/0 to 40/45/15). The fractions containing product were combined and evaporated. The oily residue was stirred up in $H_2O$ (8 mL) and MeOH (17.5 mL) was added dropwise. After stirring for 15 minutes, the precipitate was filtered off, washed with MeOH/$H_2O$ 1/1 (4×1.5 mL), and dried under vacuum at 50° C. to provide Enantiomer 3B (0.266 g).

Compound 3

$^1$H NMR (300 MHz, DMSO-$d_6$) δ ppm 2.39 (s, 3H) 3.08 (s, 3H) 3.72 (s, 3H) 3.90-4.11 (m, 2H) 4.17 (m, 2H) 5.32 (br. s., 1H) 6.39 (d, J=7.7 Hz, 1H) 6.57 (s, 1H) 6.66 (s, 1H) 6.71 (td, J=8.5, 2.3 Hz, 1H) 6.89-7.10 (m, 4H) 7.37 (t, J=7.1 Hz, 1H) 7.99 (dd, J=8.7, 5.5 Hz, 1H) 8.63 (s, 1H) 12.22 (br. s., 1H)

LC/MS (method LC-E): $R_t$ 1.07 min, MH$^+$ 545

Enantiomer 3A $^1$H NMR (360 MHz, DMSO-$d_6$) δ ppm 2.35-2.43 (m, 3H) 3.08 (s, 3H) 3.72 (s, 3H) 3.89-4.10 (m, 2H) 4.17 (t, J=4.8 Hz, 2H) 5.32 (t, J=5.7 Hz, 1H) 6.39 (d, J=7.7 Hz, 1H) 6.56-6.58 (m, 1H) 6.65-6.68 (m, 1H) 6.71 (td, J=8.5, 2.4 Hz, 1H)

6.91-6.98 (m, 2H) 6.98-7.07 (m, 2H) 7.37 (dd, J=8.6, 6.8 Hz, 1H) 7.99 (dd, J=8.7, 5.2 Hz, 1H) 8.63 (d, J=3.2 Hz, 1H) 12.22 (d, J=3.2 Hz, 1H)

LC/MS (method LC-A): $R_t$ 1.08 min, MH+ 545

$[\alpha]_D^{20}$: +110.0° (c 0.46, DMF)

Chiral SFC (method SFC-E): $R_t$ 3.30 min, MH+ 545, chiral purity 100%.

Melting point: 212° C.

Enantiomer 3B $^1$H NMR (360 MHz, DMSO-$d_6$) δ ppm 2.35-2.42 (m, 3H) 3.08 (s, 3H) 3.72 (s, 3H) 3.90-4.10 (m, 2H) 4.18 (t, J=4.8 Hz, 2H) 5.32 (t, J=5.7 Hz, 1H) 6.39 (d, J=7.7 Hz, 1H) 6.55-6.59 (m, 1H) 6.66-6.68 (m, 1H) 6.71 (td, J=8.5, 2.4 Hz, 1H) 6.91-6.97 (m, 2H) 6.98-7.07 (m, 2H) 7.37 (dd, J=8.6, 6.8 Hz, 1H) 7.99 (dd, J=8.7, 5.2 Hz, 1H) 8.64 (d, J=3.2 Hz, 1H) 12.22 (d, J=3.2 Hz, 1H)

LC/MS (method LC-A): $R_t$ 1.08 min, MH+ 545

$[\alpha]_D^{20}$: −107.3° (c 0.4985, DMF)

Chiral SFC (method SFC-E): $R_t$ 3.74 min, MH+ 545, chiral purity 100%.

Melting point: 214° C.

Example 4: Synthesis of 1-(6-chloro-7-methyl-1H-indol-3-yl)-2-(4-fluoro-2-(2-hydroxyethoxy)phenyl)-2-((3-methoxy-5-(methylsulfonyl)phenyl)amino)-ethanone (Compound 4) and Chiral Separation into Enantiomers 4A and 4B

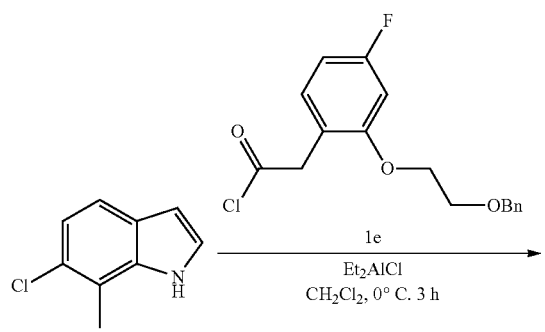

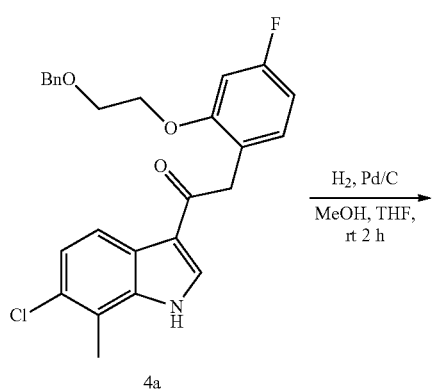

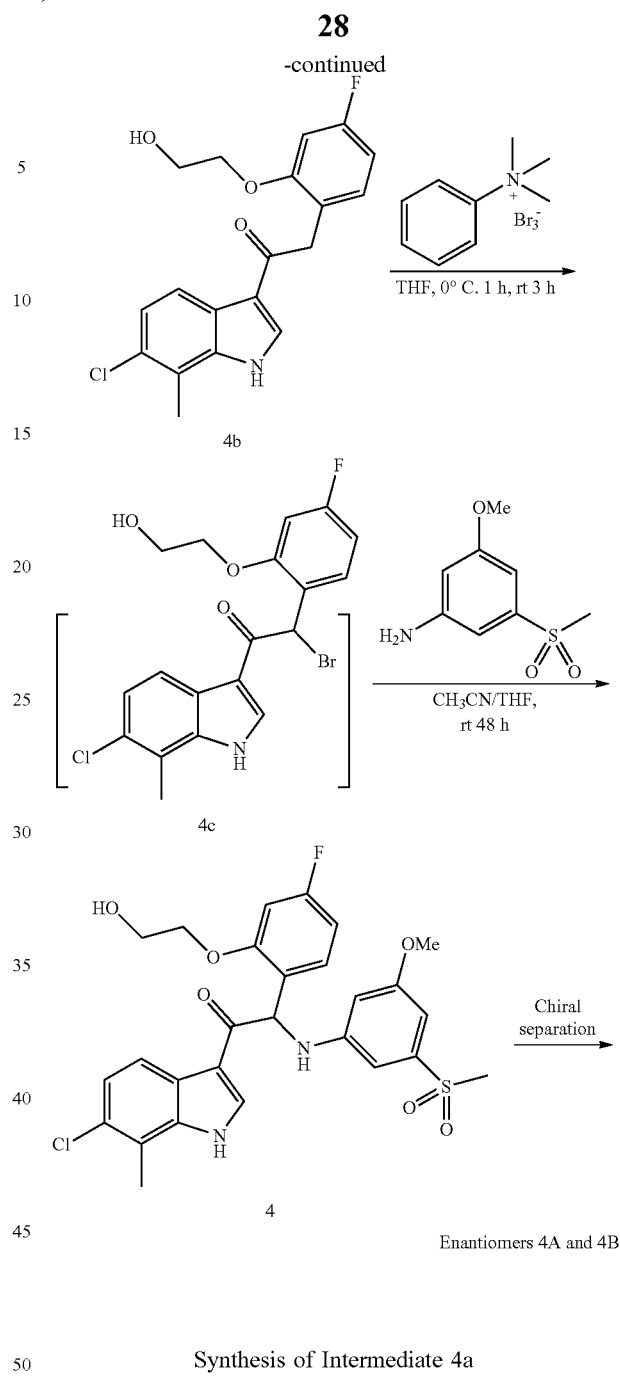

Enantiomers 4A and 4B

Synthesis of Intermediate 4a

Diethylaluminum chloride 1M in hexane (13.5 mL, 13.5 mmol) was added dropwise, at 0° C., to a solution of 6-chloro-7-methyl-1H-indole [CAS 57817-09-1](1.49 g, 9 mmol) in CH$_2$Cl$_2$ (70 mL). After 30 min at 0° C., 2-(2-(2-(benzyloxy)-ethoxy)-4-fluorophenyl)acetyl chloride 1e (8.5 g, 26.3 mmol) in CH$_2$Cl$_2$ (20 mL) was added slowly at 0° C. The reaction was stirred at 0° C. for 3 h. Ice-water was added and the reaction mixture was extracted with CH$_2$CO$_2$. The organic layer was dried over MgSO$_4$, filtered, and the solvent was evaporated under vacuum. The crude product was purified by flash chromatography on silica gel (15-40 μm, 120 g, CH$_2$Cl$_2$/CH$_3$OH 99.5/0.5). The pure fractions were combined and evaporated to dryness to give 2-(2-(2-(benzyloxy)ethoxy)-4-fluorophenyl)-1-(6-chloro-7-methyl-1H-indol-3-yl)ethanone 4a (1.86 g).

Synthesis of Intermediate 4b

A mixture of 2-(2-(2-(benzyloxy)ethoxy)-4-fluorophenyl)-1-(6-chloro-7-methyl-1H-indol-3-yl)ethanone 4a (1.76 g, 3.9 mmol) in CH$_3$OH (40 mL) and THF (40 mL) was hydrogenated under an atmospheric pressure of H$_2$ for 2 h with Pd/C (10%) (170 mg, 0.16 mmol) as a catalyst. The mixture was filtered through a pad of Celite® and washed with EtOAc/THF 70/30. The filtrate was concentrated under reduced pressure. The residue was solidified by trituration with CH$_3$CN/diisopropyl ether. The precipitate was filtered off and dried to afford 1-(6-chloro-7-methyl-1H-indol-3-yl)-2-(4-fluoro-2-(2-hydroxyethoxy)phenyl)ethanone 4b as a white powder (800 mg).

Synthesis of Compound 4 and Chiral Separation of Enantiomers 4A and 4B

Under a N$_2$ flow at 0° C., a solution of phenyltrimethylammonium tribromide [CAS 4207-56-1] (0.89 g, 2.38 mmol) in THF (40 mL) was added dropwise to a solution of 1-(6-chloro-7-methyl-1H-indol-3-yl)-2-(4-fluoro-2-(2-hydroxyethoxy)phenyl)-ethanone 4b (0.86 g, 2.38 mmol) in THF (20 mL). The mixture was stirred at 0° C. for 1 h, the cooling bath was removed and stirring was continued at room temperature for 3 h. 3-Methoxy-5-(methylsulfonyl) aniline [CAS 62606-02-4] (1.43 g, 7.13 mmol) in CH$_3$CN (20 mL) was added dropwise and the resulting mixture was stirred at room temperature for 48 h. The mixture was concentrated under reduced pressure. The residue was taken up with EtOAc and was washed with HCl 1N (twice), dried over MgSO$_4$, filtered, and the solvent was evaporated under reduced pressure. The crude product was crystallized from CH$_3$CN/diisopropyl ether to give 1-(6-chloro-7-methyl-1H-indol-3-yl)-2-(4-fluoro-2-(2-hydroxyethoxy)phenyl)-2-((3-methoxy-5-(methylsulfonyl)phenyl)amino)ethanone (Compound 4, 1.07 g) as a racemic mixture.

The enantiomers of Compound 4 (837 mg) were separated via chiral SFC (Stationary phase: Chiralcel® OD-H 5 μm 250×30 mm, Mobile phase: 60% CO$_2$, 40% EtOH (+0.3% iPrNH$_2$)) yielding 326 mg of the first eluted enantiomer and 350 mg of the second eluted enantiomer. The first eluted enantiomer was solidified by trituration with CH$_3$CN/diisopropyl ether. The precipitate was filtered off and dried to give 298 mg of Enantiomer 4A. The second eluted enantiomer was crystallized from CH$_3$CN/diisopropyl ether. The precipitate was filtered off and dried to give 267 mg of Enantiomer 4B.

Compound 4

$^1$H NMR (500 MHz, DMSO-d$_6$) δ ppm 3.09 (s, 3H) 3.72 (s, 3H) 3.92-4.08 (m, 2H) 4.13-4.21 (m, 2H) 5.32 (br s, 1H) 6.40 (d, J=7.6 Hz, 1H) 6.57 (s, 1H) 6.67 (br s, 1H) 6.71 (td, J=8.4, 2.0 Hz, 1H) 6.92-6.98 (m, 2H) 7.05 (br d, J=7.6 Hz, 1H) 7.23 (d, J=8.5 Hz, 1H) 7.37 (t, J=7.7 Hz, 1H) 8.00 (d, J=8.5 Hz, 1H) 8.64 (s, 1H) 12.28 (br s, 1H)

LC/MS (method LC-C): R$_t$ 3.07 min, MH$^+$ 561

Enantiomer 4A $^1$H NMR (500 MHz, DMSO-d$_6$) δ ppm 3.08 (s, 3H) 3.72 (s, 3H) 3.91-4.07 (m, 2H) 4.17 (t, J=4.6 Hz, 2H) 5.31 (br s, 1H) 6.39 (d, J=7.9 Hz, 1H) 6.57 (t, J=1.7 Hz, 1H) 6.66 (br s, 1H) 6.71 (td, J=8.5, 2.5 Hz, 1H) 6.91-6.98 (m, 2H) 7.04 (d, J=7.6 Hz, 1H) 7.22 (d, J=8.5 Hz, 1H) 7.37 (dd, J=8.5, 6.9 Hz, 1H) 8.00 (d, J=8.5 Hz, 1H) 8.64 (s, 1H) 12.28 (br s, 1H)

LC/MS (method LC-C): R$_t$ 3.07 min, MH$^+$ 561

[α]$_D^{20}$: −110.2° (c 0.256, DMF)

Chiral SFC (method SFC-B): R$_t$ 3.52 min, chiral purity 100%.

Enantiomer 4B $^1$H NMR (500 MHz, DMSO-d$_6$) δ ppm 3.08 (s, 3H) 3.72 (s, 3H) 3.92-4.07 (m, 2H) 4.17 (t, J=4.6 Hz, 2H) 5.32 (br s, 1H) 6.39 (d, J=7.6 Hz, 1H) 6.57 (t, J=1.7 Hz, 1H) 6.66 (s, 1H) 6.71 (td, J=8.4, 2.4 Hz, 1H) 6.91-6.97 (m, 2H) 7.04 (d, J=7.9 Hz, 1H) 7.22 (d, J=8.5 Hz, 1H) 7.37 (dd, J=8.8, 6.9 Hz, 1H) 8.00 (d, J=8.5 Hz, 1H) 8.64 (s, 1H) 12.19 (br s, 1H)

LC/MS (method LC-C): R$_t$ 3.07 min, MH$^+$ 561

[α]$_D^{20}$: +112.8° (c 0.257, DMF)

Chiral SFC (method SFC-B): R$_t$ 4.69 min, chiral purity 100%.

Melting point: 162° C.

Example 5: Synthesis of 1-(5,6-difluoro-1H-indol-3-yl)-2-(4-fluoro-2-(2-hydroxy-ethoxy)phenyl)-2-((3-methoxy-5-(methylsulfonyl)phenyl)amino)ethanone (Compound 5) and Chiral Separation into Enantiomers 5A and 5B

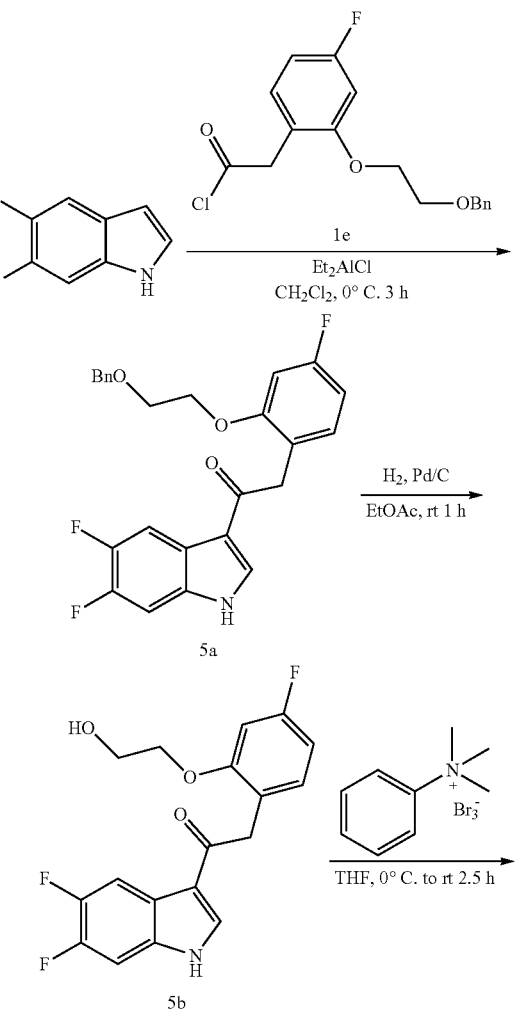

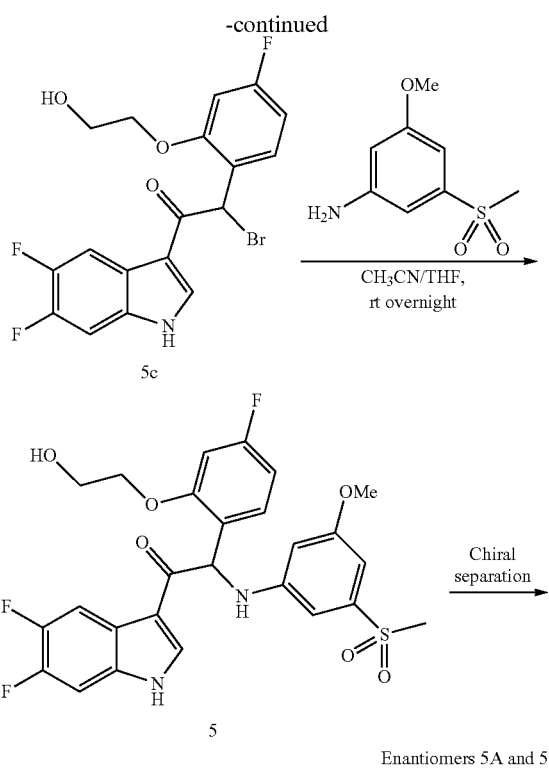

Synthesis of Intermediate 5a

Diethylaluminum chloride 1M in hexane (9.5 mL, 9.50 mmol) was added dropwise, at 0° C., to a solution of 5,6-difluoro-1H-indole [CAS 169674-01-5] (0.73 g, 4.73 mmol) in CH$_2$Cl$_2$ (20 mL). After 30 min at 0° C., a solution of 2-(2-(2-(benzyl-oxy)ethoxy)-4-fluorophenyl)acetyl chloride 1e (2.29 g, 7.10 mmol, synthesis: see Example 1) in dichloromethane (12 mL) was slowly added. The reaction mixture was stirred at 0° C. for 3 h. 1M Rochelle salt solution was added. After stirring at room temperature for 2 h, the reaction mixture was acidified with 1N HCl and was extracted twice with EtOAc. The organic phases were combined, washed with brine, dried over MgSO$_4$, filtered and concentrated under reduced pressure. The residue was purified by flash chromatography on silica gel using a gradient of EtOAc (0% to 50%) in heptane to afford 2-(2-(2-(benzyloxy)ethoxy)-4-fluoro-phenyl)-1-(5,6-difluoro-1H-indol-3-yl)ethanone 5a (0.66 g).

Synthesis of Intermediate 5b

A mixture 2-(2-(2-(benzyloxy)ethoxy)-4-fluorophenyl)-1-(5,6-difluoro-1H-indol-3-yl)-ethanone 5a (0.66 g, 1.50 mmol) and 10% palladium on carbon (0.07 g) in EtOAc (15 mL) was stirred at room temperature for 1 h under H$_2$ atmosphere. The reaction mixture was filtered through Celite®. The filtrate was concentrated under reduced pressure. The residue was purified by flash chromatography on silica gel using a gradient of EtOAc (30% to 85%) in heptane to give 1-(5,6-difluoro-1H-indol-3-yl)-2-(4-fluoro-2-(2-hydroxyethoxy)phenyl)ethanone 5b (0.28 g).

Synthesis of Intermediate 5c

A solution of phenyltrimethylammonium tribromide [CAS 4207-56-1] (0.93 g, 2.47 mmol) in THF (10 mL) was added dropwise, at 0° C., to a solution of 1-(5,6-di-fluoro-1H-indol-3-yl)-2-(4-fluoro-2-(2-hydroxyethoxy)-phenyl)ethanone 5b (0.79 g, 2.29 mmol) in THF (15 mL). The reaction mixture was stirred at 0° C. for 15 min and at room temperature for 2.5 h. The precipitate was filtered off and washed with EtOAc. The filtrate was concentrated under reduced pressure to give 2-bromo-1-5,6-difluoro-1H-indol-3-yl)-2-(4-fluoro-2-(2-hydroxyethoxy)phenyl)ethanone 5c (0.98 g) which was used in the next step without further purification.

Synthesis of Compound 5 and Chiral Separation into Enantiomers 5A and 5B

A mixture of 2-bromo-1-(5,6-difluoro-1H-indol-3-yl)-2-(4-fluoro-2-(2-hydroxy-ethoxy)phenyl)ethanone 5c (0.98 g, 2.28 mmol) and 3-methoxy-5-(methylsulfonyl)-aniline [CAS 62606-02-4] (1.36 g, 6.78 mmol) in CH$_3$CN (6 mL) and THF (6 mL) was stirred at room temperature overnight. The reaction mixture was concentrated under reduced pressure. The residue was partitioned between EtOAc and 1N HCl. The phases were separated. The aqueous phase was extracted twice with EtOAc. The organic phases were combined, washed with brine, dried over MgSO$_4$, filtered and concentrated under reduced pressure. The residue was purified by flash chromatography on silica gel using a gradient of EtOAc (15% to 70%) in CH$_2$Cl$_2$. The fractions containing the desired compound were combined and concentrated under reduced pressure. The residue was triturated with EtOAc. The solids were filtered off and dried under vacuum to give 1-(5,6-difluoro-1H-indol-3-yl)-2-(4-fluoro-2-(2-hydroxyethoxy)phenyl)-2-((3-methoxy-5-(methylsulfonyl)phenyl)-amino)ethanone (Compound 5, 0.53 g) as a racemic mixture.

The chiral separation of the Enantiomers of Compound 5 (482 mg) was performed using Normal Phase Chiral separation (Stationary phase: AS 20 µm, Mobile phase: 100% MeOH). The product fractions were combined and evaporated under reduced pressure to provide Enantiomer 5A as the first eluted product and Enantiomer 5B as the second eluted product. Enantiomer 5A was purified by flash chromatography (Stationary phase: Grace Reveleris® silica 12 g, Mobile phase: heptane/EtOAc/EtOH gradient 100/0/0 to 40/45/15). The fractions containing product were combined, evaporated under reduced pressure and co-evaporated from CH$_3$CN. The residue was lyophilized from a mixture of CH$_3$CN (3 mL) and water (3 mL) and dried under vacuum at 50° C. to provide Enantiomer 5A (0.147 g). Enantiomer 5B was purified by flash chromatography (Stationary phase: Grace Reveleris® silica 12 g, Mobile phase: heptane/EtOAc/EtOH gradient 100/0/0 to 40/45/15). The fractions containing product were combined, evaporated under reduced pressure and co-evaporated from CH$_3$CN. The residue was lyophilized from a mixture of CH$_3$CN (3 mL) and water (3 mL) and dried under vacuum at 50° C. to provide Enantiomer 5B (0.107 g).

Compound 5

$^1$H NMR (300 MHz, DMSO-d$_6$) δ ppm 3.08 (s, 3H) 3.72 (s, 3H) 3.89-4.09 (m, 2H) 4.18 (m, 2H) 5.30 (t, J=5.3 Hz, 1H) 6.36 (d, J=7.8 Hz, 1H) 6.58 (s, 1H) 6.65 (s, 1H) 6.71 (td, J=8.5, 2.3 Hz, 1H) 6.90-6.99 (m, 2H) 7.07 (d, J=7.8 Hz, 1H) 7.37 (t, J=7.1 Hz, 1H) 7.50 (dd, J=10.7, 7.0 Hz, 1H) 8.01 (dd, J=11.2, 8.2 Hz, 1H) 8.72 (s, 1H) 12.29 (br. s., 1H)

Enantiomer 5A $^1$H NMR (360 MHz, DMSO-$d_6$) δ ppm 3.08 (s, 3H) 3.72 (s, 3H) 3.86-4.07 (m, 2H) 4.17 (t, J=4.8 Hz, 2H) 5.30 (t, J=5.5 Hz, 1H) 6.35 (d, J=7.8 Hz, 1H) 6.57 (t, J=1.9 Hz, 1H) 6.63-6.67 (m, 1H) 6.72 (td, J=8.5, 2.4 Hz, 1H) 6.91-6.97 (m, 2H) 7.07 (d, J=7.8 Hz, 1H) 7.37 (dd, J=8.6, 6.8 Hz, 1H) 7.50 (dd, J=10.7, 7.0 Hz, 1H) 8.01 (dd, J=11.1, 8.1 Hz, 1H) 8.72 (s, 1H) 12.29 (brs, 1H)

LC/MS (method LC-A): $R_t$ 1.03 min, MH$^+$ 549

[α]$_D^{20}$: +122.7° (c 0.49, DMF)

Chiral SFC (method SFC-E): $R_t$ 3.28 min, MH$^+$ 549, chiral purity 100%.

Enantiomer 5B $^1$H NMR (360 MHz, DMSO-$d_6$) δ ppm 3.08 (s, 3H) 3.72 (s, 3H) 3.86-4.07 (m, 2H) 4.18 (br t, J=4.8 Hz, 2H) 5.30 (t, J=5.5 Hz, 1H) 6.36 (d, J=7.8 Hz, 1H) 6.58 (t, J=1.8 Hz, 1H) 6.63-6.67 (m, 1H) 6.73 (td, J=8.5, 2.5 Hz, 1H) 6.91-6.97 (m, 2H) 7.07 (d, J=7.8 Hz, 1H) 7.38 (dd, J=8.6, 6.8 Hz, 1H) 7.50 (dd, J=10.7, 6.9 Hz, 1H) 8.02 (dd, J=11.1, 8.1 Hz, 1H) 8.72 (s, 1H) 12.29 (brs, 1H)

LC/MS (method LC-A): $R_t$ 1.04 min, MH$^+$ 549

[α]$_D^{20}$: −123.3° (c 0.48, DMF)

Chiral SFC (method SFC-E): $R_t$ 3.74 min, MH$^+$ 549, chiral purity 100%.

Example 6: Synthesis of 2-(4-fluoro-2-(2-hydroxy-ethoxy)phenyl)-2-((3-methoxy-5-(methylsulfonyl)phenyl)amino)-1-(6-methoxy-5-methyl-1H-indol-3-yl)ethanone (Compound 6) and Chiral Separation into Enantiomers 6A and 6B

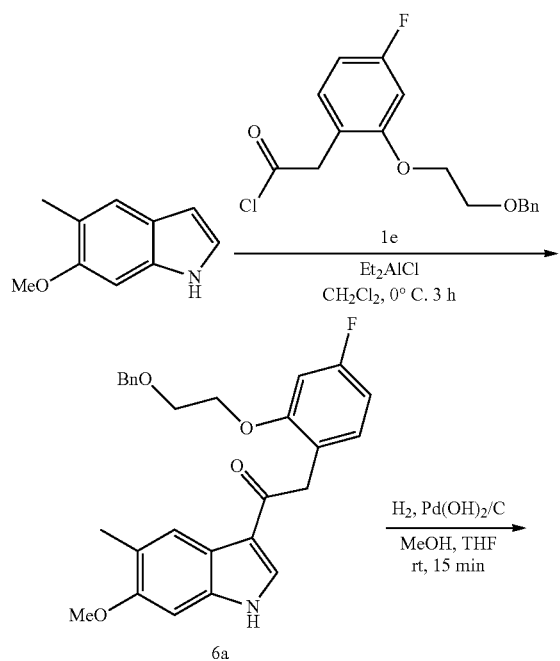

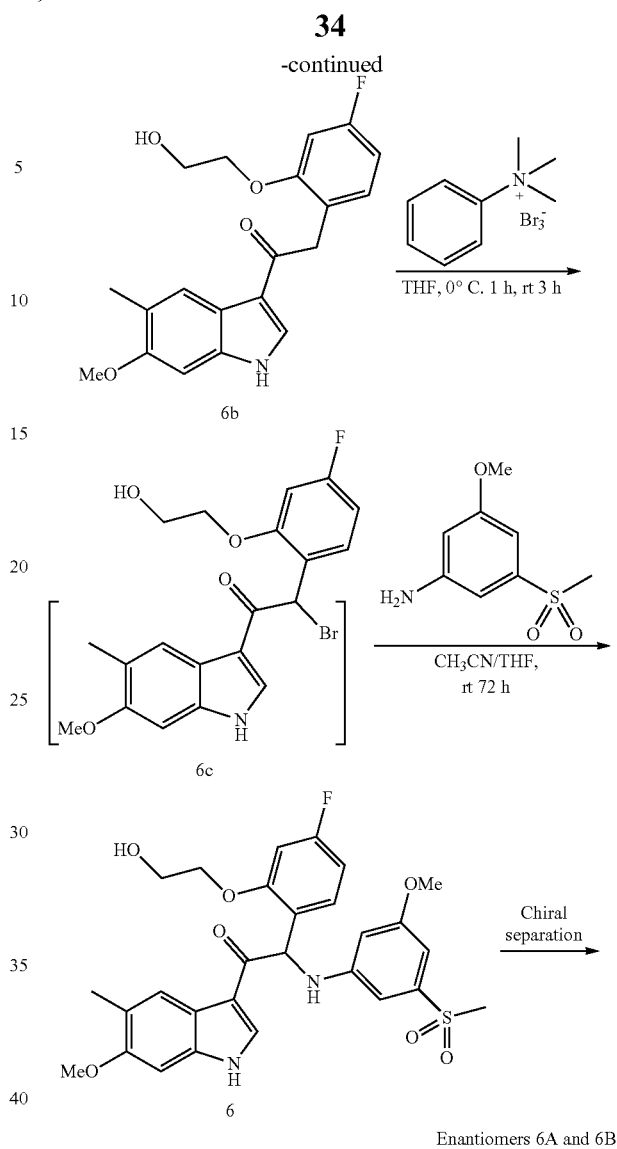

Enantiomers 6A and 6B

Synthesis of Intermediate 6a

Diethylaluminum chloride 1M in hexane (35.8 mL, 35.8 mmol) was added dropwise, at 0° C., to a solution of 6-methoxy-5-methyl-1H-indole [CAS 1071973-95-9] (3.85 g, 23.9 mmol) in CH$_2$Cl$_2$ (50 mL). After 30 min at 0° C., 2-(2-(2-(benzyl-oxy)ethoxy)-4-fluorophenyl)acetyl chloride 1e (8.5 g, 26.3 mmol) in CH$_2$Cl$_2$ (50 mL) was added slowly at 0° C. The reaction was stirred at 0° C. for 3 h. Ice-water was added and the reaction mixture was extracted with CH$_2$CO$_2$/CH$_3$OH 90/10. The organic layer was washed with a saturated Rochelle salt solution and then with brine, dried over MgSO$_4$, filtered, and the solvent was evaporated under reduced pressure. The residue was taken up with the minimum amount of CH$_2$Cl$_2$, the precipitate was filtered off and dried to provide 2-(2-(2-(benzyloxy)ethoxy)-4-fluorophenyl)-1-(6-methoxy-5-methyl-1H-indol-3-yl)ethanone 6a (6.6 g).

Synthesis of Intermediate 6b

A mixture of 2-(2-(2-(benzyloxy)ethoxy)-4-fluorophenyl)-1-(6-methoxy-5-methyl-1H-indol-3-yl)ethanone 6a (5.2 g, 11.6 mmol) in CH$_3$OH (200 mL) and THF (100 mL) was hydrogenated under atmospheric pressure of H$_2$ for 15 min with 20% Pd(OH)$_2$/C (2.45 g, 3.49 mmol). The mixture was filtered through a pad of Celite® and washed with EtOAc/THF 70/30. The filtrate was concentrated under reduced pressure. The compound was triturated with Et$_2$O, the precipitate was filtered off and dried to afford 2-(4-fluoro-2-(2-hydroxyethoxy)phenyl)-1-(6-methoxy-5-methyl-1H-indol-3-yl)ethanone 6b as a white powder (2.54 g).

Synthesis of Compound 6 and Chiral Separation of Enantiomers 6A and 6B

Under a N$_2$ flow, at 0° C., a solution of phenyltrimethylammonium tribromide [CAS 4207-56-1] (2.4 g, 6.38 mmol) in THF (15 mL) was added dropwise to a solution of 2-(4-fluoro-2-(2-hydroxyethoxy)phenyl)-1-(6-m ethoxy-5-methyl-1H-indol-3-yl)-ethanone 6b (2.28 g, 6.38 mmol) in THF (100 mL). The mixture was stirred at 0° C. for 1 h, the cooling bath was removed and stirring was continued at room temperature for 3 h. 3-Methoxy-5-(methylsulfonyl) aniline [CAS 62606-02-4] (3.85 g, 19.1 mmol) in CH$_3$CN (45 mL) was added dropwise and the resulting mixture was stirred at room temperature for 72 h. The mixture was concentrated under reduced pressure. The residue was taken up with EtOAc and washed with HCl 1N (twice), dried over MgSO$_4$, filtered, and the solvent was evaporated under reduced pressure. The crude residue (4 g) was combined with another fraction (1 g) and purified by flash chromatography on silica gel (15-40 µm, 120 g, CH$_2$Cl$_2$/CH$_3$OH 99/1). The pure fractions were combined and evaporated to dryness to give 2-(4-fluoro-2-(2-hydroxyethoxy)phenyl)-2-((3-methoxy-5-(methylsulfonyl)phenyl)-amino)-1-(6-methoxy-5-methyl-1H-indol-3-yl)ethanone (Compound 6, 1.3 g) as a racemic mixture.

The enantiomers of Compound 6 (1.55 g) were separated via chiral SFC (Stationary phase: Chiralcel® OD-H 5 µm 250×30 mm, Mobile phase: 60% CO$_2$, 40% EtOH (+0.3% iPrNH$_2$)) yielding 590 mg of the first eluted enantiomer and 613 mg of the second eluted enantiomer. The first eluted enantiomer was crystallized from Et$_2$O. The precipitate was filtered off and dried to give 529 mg of Enantiomer 6A. The second eluted enantiomer was crystallized from Et$_2$O. The precipitate was filtered off and dried to give 517 mg of Enantiomer 6B.

Compound 6

$^1$H NMR (500 MHz, DMSO-d$_6$) δ ppm 2.21 (s, 3H) 3.08 (s, 3H) 3.71 (s, 3H) 3.79 (s, 3H) 3.90-3.97 (m, 1H) 3.98-4.06 (m, 1H) 4.17 (t, J=4.6 Hz, 2H) 5.29 (br t, J=4.9 Hz, 1H) 6.31 (d, J=7.6 Hz, 1H) 6.56 (t, J=1.7 Hz, 1H) 6.64 (s, 1H) 6.71 (td, J=8.4, 2.4 Hz, 1H) 6.89 (s, 1H) 6.91-6.95 (m, 2H) 6.99 (d, J=7.9 Hz, 1H) 7.37 (dd, J=8.5, 6.9 Hz, 1H) 7.91 (s, 1H) 8.48 (s, 1H) 11.82 (s, 1H)

LC/MS (method LC-G): R$_t$ 2.67 min, MH$^+$ 557

Enantiomer 6A $^1$H NMR (500 MHz, DMSO-d$_6$) δ ppm 2.21 (s, 3H) 3.08 (s, 3H) 3.71 (s, 3H) 3.79 (s, 3H) 3.94 (dq, J=8.2, 4.1 Hz, 1H) 4.03 (dq, J=11.7, 5.6 Hz, 1H) 4.17 (t, J=4.6 Hz, 2H) 5.29 (t, J=5.5 Hz, 1H) 6.32 (d, J=7.9 Hz, 1H) 6.56 (m, 1H) 6.64 (br s, 1H) 6.71 (td, J=8.5, 2.2 Hz, 1H) 6.89 (s, 1H) 6.91-6.96 (m, 2H) 6.99 (d, J=7.9 Hz, 1H) 7.37 (dd, J=8.5, 6.9 Hz, 1H) 7.91 (s, 1H) 8.48 (s, 1H) 11.82 (br s, 1H)

LC/MS (method LC-C): R$_t$ 2.87 min, MH$^+$ 557
[α]$_D^{20}$: +125.5° (C 0.2527, DMF)
Chiral SFC (method SFC-C): R$_t$ 2.52 min, MH$^+$ 557, chiral purity 100%.
Melting point: 232° C.

Enantiomer 6B $^1$H NMR (500 MHz, DMSO-d$_6$) δ ppm 2.21 (s, 3H) 3.08 (s, 3H) 3.71 (s, 3H) 3.79 (s, 3H) 3.90-3.97 (m, 1H) 3.99-4.07 (m, 1H) 4.17 (t, J=4.6 Hz, 2H) 5.29 (br s, 1H) 6.32 (d, J=7.9 Hz, 1H) 6.56 (m, 1H) 6.64 (br s, 1H) 6.71 (td, J=8.4, 2.4 Hz, 1H) 6.89 (s, 1H) 6.91-6.96 (m, 2H) 6.99 (d, J=7.6 Hz, 1H) 7.37 (dd, J=8.4, 7.1 Hz, 1H) 7.91 (s, 1H) 8.48 (s, 1H) 11.82 (br s, 1H)

LC/MS (method LC-C): R$_t$ 2.87 min, MH$^+$ 557
[α]$_D^{20}$: −127.1 (C 0.2455, DMF)
Chiral SFC (method SFC-C): R$_t$ 4.14 min, MH$^+$ 557, chiral purity 100%.
Melting point: 235° C.

Example 7: Synthesis of 2-(4-fluoro-2-(2-hydroxyethoxy)phenyl)-1-(6-fluoro-5-methyl-1H-indol-3-yl)-2-((3-methoxy-5-(methylsulfonyl)phenyl)amino) ethanone (Compound 7) and Chiral Separation into Enantiomers 7A and 7B

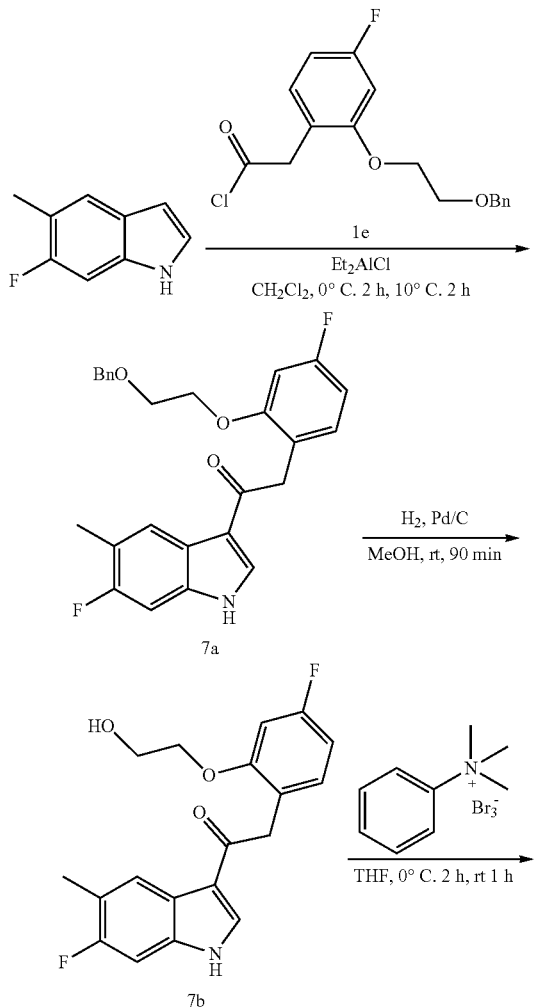

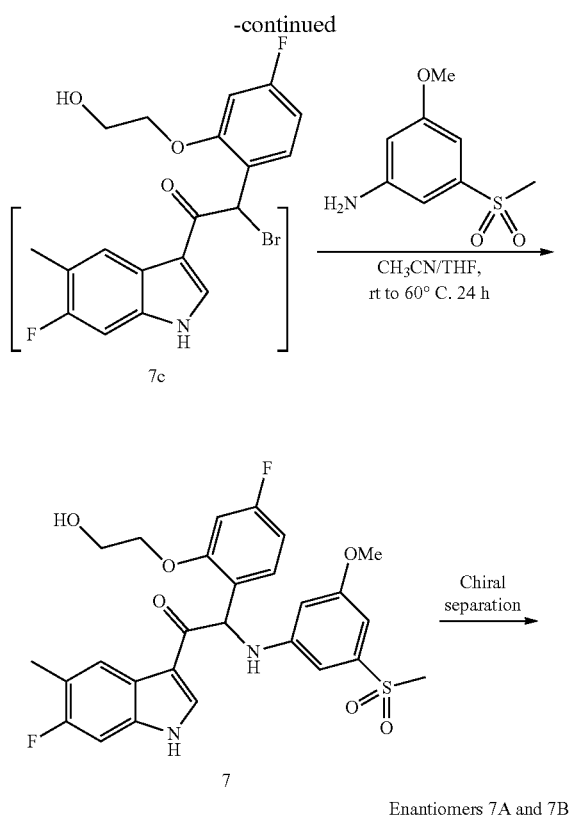

Synthesis of Intermediate 7a

Diethylaluminum chloride 1M in hexane (25.1 mL, 25.1 mmol) was added dropwise, at 0° C. and under N₂-flow, to a solution of 6-fluoro-5-methyl-1H-indole [CAS 162100-95-0] (2.5 g, 16.8 mmol) in CH₂Cl₂ (135 mL). After 10 min at 0° C., a solution of 2-(2-(2-(benzyloxy)ethoxy)-4-fluorophenyl)acetyl chloride 1e (8.11 g, 25.1 mmol) in CH₂Cl₂ (50 mL) was added dropwise at 0° C. over a period of 45 min, while keeping the reaction temperature below 5° C. The reaction was stirred at 0° C. for 2 h and at 10° C. for 2 h. The reaction mixture was cooled to 0° C., and a solution of Rochelle salt [6100-16-9] (9.46 g, 33.5 mmol) in water (10 mL) was added dropwise. After addition, the reaction mixture was stirred at 0° C. for 10 minutes and then allowed to warm to room temperature. THF (150 mL) and Na₂SO₄ (40 g) were added, and the mixture was stirred for 18 h. The mixture was filtered over Dicalite® and washed with plenty of THF. The combined filtrates were evaporated under reduced pressure, and co-evaporated with toluene. The residue was crystallized from CH₃CN (10 mL), filtered off, washed with CH₃CN (2×), and dried under vacuum at 40° C. to provide a first fraction of 2-(2-(2-(benzyloxy)ethoxy)-4-fluorophenyl)-1-(6-fluoro-5-methyl-1H-indol-3-yl)ethanone 7a (1.86 g). The filtrate was evaporated under reduced pressure. The residue (7.7 g) was purified by flash chromatography (Stationary phase: Grace Reveleris® silica 120 g, Mobile phase: heptane/EtOAc gradient 100/0 to 0/100). The fractions containing product were combined and left standing in an open recipient to allow evaporation of the solvent and crystallization of the product. The precipitate was isolated by filtration, washed 3× with heptane/EtOAc (1/1) and dried under vacuum at 40° C. to provide a second (1.51 g) and third (0.75 g) fraction of intermediate 7a.

Synthesis of Intermediate 7b

A mixture of 2-(2-(2-(benzyloxy)ethoxy)-4-fluorophenyl)-1-(6-fluoro-5-methyl-1H-indol-3-yl)ethanone 7a (1.86 g, 4.27 mmol) in methanol (80 mL) was hydrogenated under atmospheric pressure of H₂ for 90 min with 10% Pd/C (0.5 g). The mixture was filtered through a pad of Dicalite® and washed with MeOH. The filtrate was concentrated under reduced pressure. The solid residue was stirred up in diisopropyl ether (10 mL). The precipitate was filtered off, washed with DIPE (4×1.5 mL) and dried under vacuum at 50° C. to afford 2-(4-fluoro-2-(2-hydroxy-ethoxy)phenyl)-1-(6-fluoro-5-methyl-1H-indol-3-yl)ethanone 7b (330 mg).

Synthesis of Compound 7 and Chiral Separation of Enantiomers 7A and 7B

Under a N₂ flow, at 0° C., a solution of phenyltrimethylammonium tribromide [CAS 4207-56-1] (447 mg, 1.24 mmol) in THF (25 mL) was added dropwise to a solution of 2-(4-fluoro-2-(2-hydroxyethoxy)phenyl)-1-(6-fluoro-5-methyl-1H-indol-3-yl)-ethanone 7b (390 mg, 1.13 mmol) in THF (25 mL). The mixture was stirred at 0° C. for 2 h and at room temperature for 1 h. The reaction mixture, containing crude 2-bromo-2-(4-fluoro-2-(2-hydroxyethoxy)phenyl)-1-(6-fluoro-5-methyl-1H-indol-3-yl)ethanone 7c, was mixed with a solution of 3-methoxy-5-(methylsulfonyl)-aniline [CAS 62606-02-4] (579 mg, 2.88 mmol) and diisopropylethylamine (165 µL, 0.96 mmol) in CH₃CN (100 mL) and the reaction mixture was stirred at room temperature overnight, under N₂-atmosphere. The reaction temperature was subsequently increased to 50° C. for 4 h and to 60° C. for 24 h. The solvents were evaporated under reduced pressure. The residue was dissolved in DCM (100 mL) and washed with 1N HCl (100 mL). The organic layer was washed with water (100 mL), dried over MgSO₄, filtered and evaporated under reduced pressure. The residue was purified via column chromatography (Stationary phase: Grace Reveleris® 120 g, eluent: EtOAc/EtOH (3:1)/heptane gradient 0/100 to 50/50). The fraction containing product were combined and evaporated under reduced pressure. The solid residue was crystallized from MeOH/water. The precipitate was isolated by filtration, washed with MeOH/water 1/1 (4 mL) and dried under vacuum at 50° C. to provide racemic 2-(4-fluoro-2-(2-hydroxyethoxy)phenyl)-1-(6-fluoro-5-methyl-1H-indol-3-yl)-2-((3-methoxy-5-(methylsulfonyl)phenyl)amino)-ethanone (Compound 7, 205 mg).

The chiral separation of the enantiomers of Compound 7 was performed via preparative SFC (Stationary phase: Chiralpak® Diacel AS 20×250 mm, Mobile phase: CO₂, EtOH+ 0.4% iPrNH₂). The fractions containing product were combined and evaporated to provide Enantiomer 7A as the first eluted product and Enantiomer 7B as the second eluted product. Both enantiomers were stirred up in MeOH/water 1/1 (10 mL) and stirred for 1 h. The solids were filtered off and dried under vacuum at 40° C. to provide Enantiomer 7A (8 mg) and Enantiomer 7B (32 mg) as white powders.

Enantiomer 7A $^1$H NMR (400 MHz, DMSO-$d_6$) δ ppm 2.30 (d, J=1.1 Hz, 3H) 3.07 (s, 3H) 3.72 (s, 3H) 3.89-4.07 (m, 2H) 4.18 (t, J=4.5 Hz, 2H) 5.28 (br s, 1H) 6.33 (d, J=7.7 Hz, 1H) 6.57 (t, J=1.7 Hz, 1H) 6.64 (t, J=2.3 Hz, 1H) 6.71 (td, J=8.5, 2.4 Hz, 1H) 6.89-6.96 (m, 2H) 6.99 (d, J=7.9 Hz, 1H) 7.19 (d, J=10.1 Hz, 1H) 7.37 (dd, J=8.6, 7.0 Hz, 1H) 8.03 (d, J=7.7 Hz, 1H) 8.61 (s, 1H) 11.89 (br s, 1H)

LC/MS (method LC-B): $R_t$ 1.95 min, MH$^+$ 545

$[α]_D^{20}$: +141.4° (c 0.43, DMF)

Chiral SFC (method SFC-E): $R_t$ 3.36 min, MH$^+$ 545, chiral purity 98.9%.

Enantiomer 7B $^1$H NMR (400 MHz, DMSO-$d_6$) δ ppm 2.30 (d, J=1.3 Hz, 3H) 3.07 (s, 3H) 3.72 (s, 3H) 3.88-4.05 (m, 2H) 4.18 (t, J=4.6 Hz, 2H) 5.34 (br s, 1H) 6.32 (d, J=7.7 Hz, 1H) 6.56 (t, J=1.8 Hz, 1H) 6.64 (t, J=2.1 Hz, 1H) 6.70 (td, J=8.4, 2.3 Hz, 1H) 6.89-6.95 (m, 2H) 6.98 (d, J=7.7 Hz, 1H) 7.19 (d, J=10.1 Hz, 1H) 7.37 (dd, J=8.6, 6.8 Hz, 1H) 8.02 (d, J=7.7 Hz, 1H) 8.62 (s, 1H)

LC/MS (method LC-B): $R_t$ 1.95 min, MH$^+$ 545

$[α]_D^{20}$: −144.7° (c 0.465, DMF)

Chiral SFC (method SFC-E): $R_t$ 3.77 min, MH$^+$ 545, chiral purity 100%.

Example 8: Synthesis of 2-(4-fluoro-2-(2-hydroxyethoxy)phenyl)-1-(7-fluoro-5-methyl-1H-indol-3-yl)-2-((3-methoxy-5-(methylsulfonyl)phenyl)amino)ethanone (Compound 8) and Chiral Separation into Enantiomers 8A and 8B

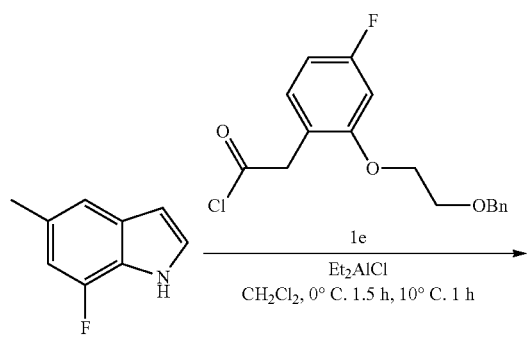

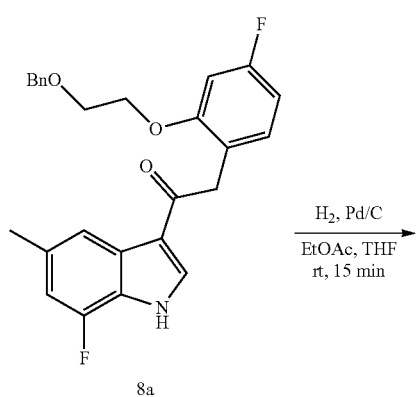

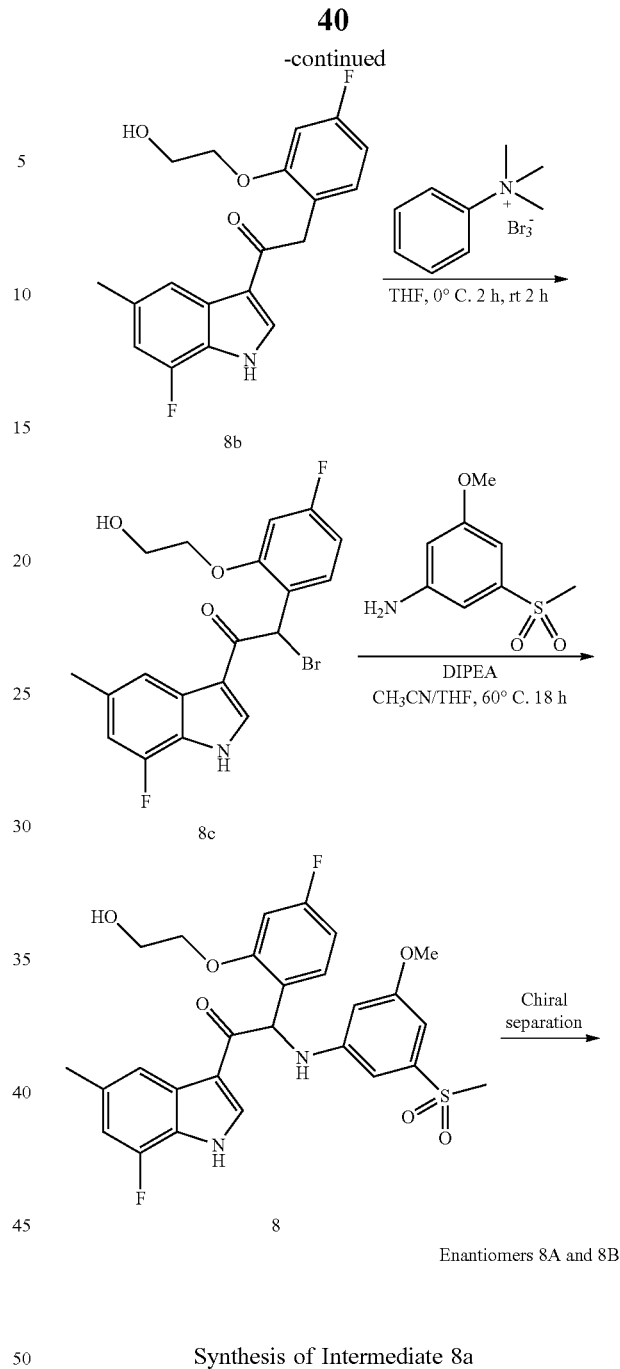

Enantiomers 8A and 8B

Synthesis of Intermediate 8a

Diethylaluminum chloride 1M in hexane (18.6 mL, 18.6 mmol) was added dropwise, at 0° C. and under N$_2$-flow, to a solution of 7-fluoro-5-methyl-1H-indole [CAS 442910-91-0] (1.85 g, 12.4 mmol) in CH$_2$Cl$_2$ (100 mL). After 5 min at 0° C., a solution of 2-(2-(2-(benzyloxy)ethoxy)-4-fluorophenyl)acetyl chloride 1e (6.0 g, 18.6 mmol) in CH$_2$Cl$_2$ (35 mL) was added dropwise at 0° C. over a period of 50 min, while keeping the reaction temperature below 6° C. The reaction was stirred at 0° C. for 90 min and at 10° C. for 1 h. The reaction mixture was cooled to 0° C., and a solution of Rochelle salt [6100-16-9] (7.0 g, 24.8 mol) in water (7.5 mL) was added dropwise. After addition, the reaction mixture was stirred at 0° C. for 10 minutes and then allowed to warm to room temperature. THF (125 mL) and Na$_2$SO$_4$ (30 g) were added, and the mixture was stirred for 18 h. The mixture was filtered over Dicalite®, washed with plenty of THF and the combined filtrates were evaporated under reduced pressure. The residue was stirred up in CH$_3$CN (7.5 mL) at 40° C. for 1 h. The precipitate was filtered off, washed with CH$_3$CN (2×), and dried under vacuum at 40° C. to provide 2-(2-(2-(benzyloxy)ethoxy)-4-fluorophenyl)-1-(7-fluoro-5-methyl-1H-indol-3-yl)ethanone 8a (two crops: 0.55 g and 1.86 g).

Synthesis of Intermediate 8b

A mixture of 2-(2-(2-(benzyloxy)ethoxy)-4-fluorophenyl)-1-(7-fluoro-5-methyl-1H-indol-3-yl)ethanone 8a (2.4 g, 5.51 mmol) in EtOAc (80 mL) and THF (10 mL) was hydrogenated under atmospheric pressure of H$_2$ for 15 min with 10% Pd/C (0.5 g). The mixture was filtered through a pad of Dicalite® and the filter cake was washed with EtOAc and THF. The filtrate was concentrated under reduced pressure. The solid residue was stirred up in diisopropyl ether/diethyl ether 1/1 (30 mL). The precipitate was filtered off, washed with DIPE/Et$_2$O 1/1 (3×) and dried under vacuum at 50° C. to afford 2-(4-fluoro-2-(2-hydroxyethoxy)phenyl)-1-(7-fluoro-5-methyl-1H-indol-3-yl)ethanone 8b (1.47 g).

Synthesis of Intermediate 8c

A solution of 2-(4-fluoro-2-(2-hydroxyethoxy)phenyl)-1-(7-fluoro-5-methyl-1H-indol-3-yl)ethanone 8b (1.47 g, 4.26 mmol) in THF (40 mL) was cooled to 0° C., under a N$_2$ flow. Phenyltrimethylammonium tribromide [CAS 4207-56-1] (1.68 g, 4.47 mmol) was added portionwise and the reaction mixture was stirred at 0° C. for 2 h and at room temperature for 2 h. The precipitate was filtered off, washed with THF and the combined filtrates were evaporated under reduced pressure to give 2-bromo-2-(4-fluoro-2-(2-hydroxyethoxy)phenyl)-1-(7-fluoro-5-methyl-1H-indol-3-yl)ethanone 8c (1.81 g) which was used without further purification in the next step.

Synthesis of Compound 8 and Chiral Separation of Enantiomers 8A and 8B

2-Bromo-2-(4-fluoro-2-(2-hydroxyethoxy)phenyl)-1-(7-fluoro-5-methyl-1H-indol-3-yl)ethanone 8c (1.81 g, 4.26 mmol), 3-methoxy-5-(methylsulfonyl)aniline [CAS 62606-02-4] (1.71 g, 8.51 mmol) and diisopropylethylamine (1.47 mL, 8.51 mmol) were dissolved in CH$_3$CN (60 mL) and THF (40 mL) and the reaction mixture was stirred at 60° C. for 18 h under N$_2$-atmosphere. The reaction mixture was allowed to reach room temperature, and poured out into water (400 mL). The product was extracted with Et$_2$O (2×). The combined organic layers were washed with brine, dried over MgSO$_4$, filtered, and evaporated under reduced pressure. The residue (3.4 g) was purified by flash chromatography (Stationary phase: Grace Reveleris® silica 80 g, Mobile phase: heptane/EtOAc/EtOH gradient 100/0/0 to 40/45/15). The desired fractions were combined and evaporated under reduced pressure. The product was further purified via preparative HPLC (Stationary phase: Uptisphere® C18 ODB—10 μm, 200 g, 5 cm, Mobile phase: 0.25% NH$_4$HCO$_3$ solution in water, CH$_3$CN). The desired fractions were combined and the organic volatiles were evaporated very slowly on a rotary evaporator under reduced pressure (bath temperature 40° C.), allowing precipitation of the product. The solids were filtered off, washed with water (4×), and dried under vacuum at 50° C. to provide racemic 2-(4-fluoro-2-(2-hydroxyethoxy)phenyl)-1-(7-fluoro-5-methyl-1H-indol-3-yl)-2-((3-methoxy-5-(methylsulfonyl) phenyl)amino)ethanone (Compound 8, 1.26 g). The chiral separation of the enantiomers of Compound 8 was performed via Normal Phase Chiral separation (Stationary phase: AS 20 μm, Mobile phase: 100% methanol). The fractions containing product were combined and evaporated to provide Enantiomer 8A as the first eluted product and Enantiomer 8B as the second eluted product. Both residues were stirred up in water (3 mL) and MeOH (2 mL), filtered off, washed (3×) with MeOH/water (1/2), and dried under vacuum at 45° C. to provide Enantiomer 8A (416 mg) and Enantiomer 8B (399 mg).

Compound 8

$^1$H NMR (400 MHz, DMSO-d$_6$) δ ppm 2.39 (s, 3H) 3.08 (s, 3H) 3.72 (s, 3H) 3.90-4.03 (m, 2H) 4.16 (t, J=4.7 Hz, 2H) 5.22 (t, J=5.6 Hz, 1H) 6.37 (d, J=7.7 Hz, 1H) 6.57 (t, J=1.8 Hz, 1H) 6.65 (t, J=2.3 Hz, 1H) 6.71 (td, J=8.5, 2.4 Hz, 1H) 6.87-6.96 (m, 3H) 6.99 (d, J=7.7 Hz, 1H) 7.38 (dd, J=8.6, 6.8 Hz, 1H) 7.80 (br s, 1H) 8.60 (s, 1H) 12.50 (s, 1H)
LC/MS (method LC-B): R$_t$ 1.97 min, MH$^+$ 545

Enantiomer 8A $^1$H NMR (400 MHz, DMSO-d$_6$) δ ppm 2.39 (s, 3H) 3.08 (s, 3H) 3.72 (s, 3H) 3.89-4.03 (m, 2H) 4.16 (t, J=4.6 Hz, 2H) 5.22 (t, J=5.5 Hz, 1H) 6.37 (d, J=7.9 Hz, 1H) 6.57 (t, J=1.9 Hz, 1H) 6.65 (t, J=2.3 Hz, 1H) 6.71 (td, J=8.5, 2.4 Hz, 1H) 6.87-6.96 (m, 3H) 6.99 (d, J=7.9 Hz, 1H) 7.38 (dd, J=8.6, 6.8 Hz, 1H) 7.80 (s, 1H) 8.60 (s, 1H) 12.50 (br s, 1H)
LC/MS (method LC-A): R$_t$ 1.05 min, MH$^+$ 545
[α]$_D^{20}$: +146.7° (c 0.54, DMF)
Chiral SFC (method SFC-E): R$_t$ 3.18 min, MH$^+$ 545, chiral purity 100%.

Enantiomer 8B $^1$H NMR (400 MHz, DMSO-d$_6$) δ ppm 2.39 (s, 3H) 3.08 (s, 3H) 3.72 (s, 3H) 3.89-4.03 (m, 2H) 4.16 (t, J=4.6 Hz, 2H) 5.22 (br t, J=5.3 Hz, 1H) 6.36 (d, J=7.7 Hz, 1H) 6.57 (t, J=1.8 Hz, 1H) 6.65 (t, J=2.1 Hz, 1H) 6.71 (td, J=8.5, 2.4 Hz, 1H) 6.86-6.96 (m, 3H) 6.99 (d, J=7.7 Hz, 1H) 7.37 (dd, J=8.6, 6.8 Hz, 1H) 7.80 (s, 1H) 8.60 (s, 1H) 12.50 (br s, 1H)
LC/MS (method LC-A): R$_t$ 1.05 min, MH$^+$ 545
[α]$_D^{20}$: −144.5° (c 0.53, DMF)
Chiral SFC (method SFC-E): R$_t$ 3.59 min, MH$^+$ 545, chiral purity 99.3%.

Example 9: Synthesis of 1-(5-chloro-7-methyl-1H-indol-3-yl)-2-(4-fluoro-2-(2-hydroxyethoxy)phenyl)-2-((3-methoxy-5-(methylsulfonyl)phenyl)amino)-ethanone (Compound 9) and Chiral Separation into Enantiomers 9A and 9B

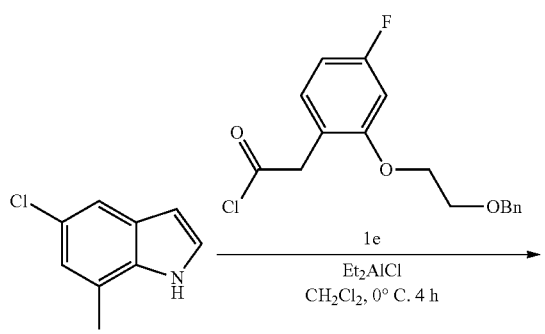

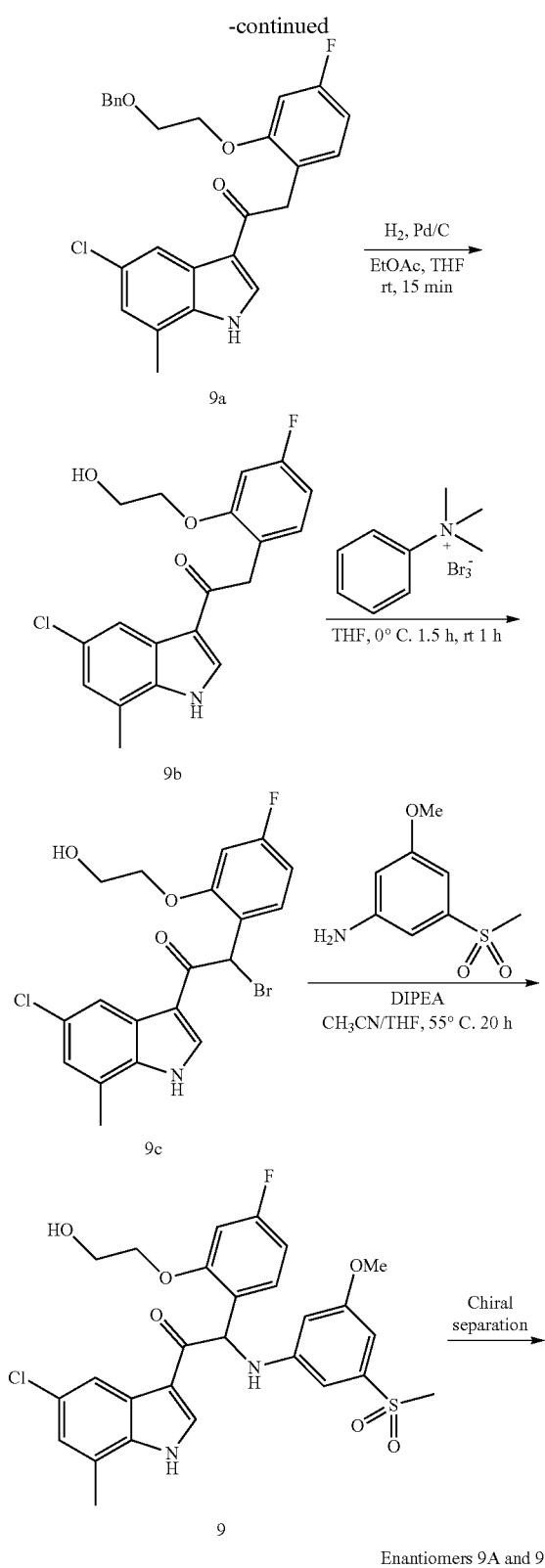

Synthesis of Intermediate 9a

Diethylaluminum chloride 1M in hexane (28.1 mL, 28.1 mmol) was added dropwise, at 0° C. and under N₂-flow, to a solution of 5-chloro-7-methyl-1H-indole [CAS 15936-77-3] (3.1 g, 18.7 mmol) in CH₂Cl₂ (175 mL). After stirring for 15 min at 0° C., a solution of 2-(2-(2-(benzyloxy)ethoxy)-4-fluorophenyl)acetyl chloride 1e (9.06 g, 28.1 mmol) in CH₂Cl₂ (75 mL) was added dropwise at 0° C. over a period of 75 min, while keeping the reaction temperature below 4° C. The reaction was stirred at 0° C. for 4 h. The reaction mixture was cooled to 0° C., and a solution of Rochelle salt [6100-16-9] (10.6 g, 37.4 mol) in water (11 mL) was added dropwise. After addition, the reaction mixture was stirred at 0° C. for 10 minutes and then allowed to warm to room temperature. THF (200 mL) and Na₂SO₄ (45 g) were added, and the mixture was stirred for 18 h. The mixture was filtered over Dicalite®, washed with plenty of THF and the combined filtrates were evaporated under reduced pressure. The residue was stirred up in CH₃CN (15 mL) at 40° C. The precipitate was filtered off, washed with CH₃CN (2×), and dried under vacuum at 40° C. to provide 2-(2-(2-(benzyloxy)ethoxy)-4-fluorophenyl)-1-(5-chloro-7-methyl-1H-indol-3-yl)ethanone 9a (4.0 g).

Synthesis of Intermediate 9b

A mixture of 2-(2-(2-(benzyloxy)ethoxy)-4-fluorophenyl)-1-(5-chloro-7-methyl-1H-indol-3-yl)ethanone 9a (4.0 g, 8.85 mmol) in EtOAc (80 mL) and THF (50 mL) was hydrogenated under atmospheric pressure of H₂ for 15 min with 10% Pd/C (0.5 g). The mixture was filtered through a pad of Dicalite® and the filter cake was washed with THF. The filtrate was concentrated under reduced pressure. The solid residue was stirred up in diisopropyl ether/diethyl ether 1/1 (40 mL). The precipitate was filtered off, washed with DIPE/Et₂O 1/1 (3×) and dried under vacuum at 45° C. to afford 1-(5-chloro-7-methyl-1H-indol-3-yl)-2-(4-fluoro-2-(2-hydroxyethoxy)phenyl)-ethanone 9b (2.88 g).

Synthesis of Intermediate 9c

A solution of 1-(5-chloro-7-methyl-1H-indol-3-yl)-2-(4-fluoro-2-(2-hydroxyethoxy)-phenyl)ethanone 9b (1.5 g, 4.15 mmol) in THF (40 mL) was cooled to 0° C., under a N₂ flow. Phenyltrimethylammonium tribromide [CAS 4207-56-1] (1.64 g, 4.35 mmol) was added portionwise and the reaction mixture was stirred at 0° C. for 90 min and at room temperature for 1 h. The precipitate was filtered off, washed with THF (3×) and the combined filtrates were evaporated under reduced pressure to give 2-bromo-1-(5-chloro-7-methyl-1H-indol-3-yl)-2-(4-fluoro-2-(2-hydroxy-ethoxy)phenyl)ethanone 9c (1.83 g) which was used without further purification in the next step.

Synthesis of Compound 9 and Chiral Separation of Enantiomers 9A and 9B

2-Bromo-1-(5-chloro-7-methyl-1H-indol-3-yl)-2-(4-fluoro-2-(2-hydroxyethoxy)-phenyl)ethanone 9c (1.83 g, 4.15 mmol), 3-methoxy-5-(methylsulfonyl)aniline [CAS 62606-02-4] (1.67 g, 8.29 mmol) and diisopropylethylamine (1.43 mL, 8.29 mmol) were dissolved in CH₃CN (60 mL) and THF (40 mL) and the reaction mixture was stirred at 55° C. for 20 h under N₂-atmosphere. The reaction mixture was allowed to reach room temperature, and poured out into water (400 mL). The product was extracted with Et₂O (2×). The combined organic layers were washed with brine, dried over MgSO₄, filtered, and evaporated under reduced pressure. The residue was stirred up in CH₂Cl₂ (7.5 mL). The solids were filtered off, washed (2×) with CH₂Cl₂, and dried under vacuum at 45° C. to provide racemic 1-(5-chloro-7-methyl-1H-indol-3-yl)-2-(4-fluoro-2-(2-hydroxyethoxy)phenyl)-2-((3-methoxy-5-(methylsulfonyl)phenyl)amino)ethanone (Compound 9, 1.08 g).

The chiral separation of the enantiomers of Compound 9 was performed via Normal Phase Chiral separation (Stationary phase: AS 20 μm, Mobile phase: 100% methanol). The fractions containing product were combined and evaporated to provide Enantiomer 9A as the first eluted product and Enantiomer 9B as the second eluted product. Both enantiomers were crystallized from $CH_2Cl_2$ (4 mL), filtered off, washed (3×) with $CH_2Cl_2$, and dried under vacuum at 45° C. to provide Enantiomer 9A (256 mg) and Enantiomer 9B (183 mg).

Enantiomer 9A $^1$H NMR (400 MHz, DMSO-$d_6$) δ ppm 2.47 (s, 3H) 3.08 (s, 3H) 3.72 (s, 3H) 3.90-4.07 (m, 2H) 4.18 (t, J=4.6 Hz, 2H) 5.28 (t, J=5.7 Hz, 1H) 6.38 (d, J=7.7 Hz, 1H) 6.58 (t, J=1.8 Hz, 1H) 6.67 (t, J=2.2 Hz, 1H) 6.71 (td, J=8.5, 2.4 Hz, 1H) 6.89-6.97 (m, 2H) 7.01 (d, J=7.7 Hz, 1H) 7.07 (d, J=1.1 Hz, 1H) 7.37 (dd, J=8.6, 6.8 Hz, 1H) 7.99 (d, J=1.8 Hz, 1H) 8.64 (s, 1H) 12.29 (br s, 1H)

LC/MS (method LC-B): $R_t$ 2.06 min, MH$^+$ 561

$[α]_D^{20}$: +145.3° (C 0.45, DMF)

Chiral SFC (method SFC-E): Rt 3.63 min, MH+ 561, chiral purity 100%.

Enantiomer 9B $^1$H NMR (400 MHz, DMSO-$d_6$) δ ppm 2.47 (s, 3H) 3.08 (s, 3H) 3.72 (s, 3H) 3.90-4.07 (m, 2H) 4.17 (t, J=4.7 Hz, 2H) 5.28 (t, J=5.7 Hz, 1H) 6.38 (d, J=7.9 Hz, 1H) 6.57 (t, J=1.8 Hz, 1H) 6.66 (t, J=2.1 Hz, 1H) 6.71 (td, J=8.5, 2.4 Hz, 1H) 6.90-6.97 (m, 2H) 7.01 (d, J=7.7 Hz, 1H) 7.06-7.09 (m, 1H) 7.37 (dd, J=8.6, 7.0 Hz, 1H) 7.99 (d, J=1.8 Hz, 1H) 8.64 (d, J=3.3 Hz, 1H) 12.29 (d, J=2.9 Hz, 1H)

LC/MS (method LC-A): $R_t$ 1.13 min, MH$^+$ 561

$[α]_D^{20}$: −144.6° (C 0.605, DMF)

Chiral SFC (method SFC-E): $R_t$ 4.14 min, MH$^+$ 561, chiral purity 100%.

Example 10: Synthesis of 2-(4-fluoro-2-(2-hydroxyethoxy)phenyl)-2-((3-methoxy-5-(methylsulfonyl)phenyl)amino)-1-(5-(trifluoromethoxy)-1H-indol-3-yl)ethanone (Compound 10) and Chiral Separation into Enantiomers 10A and 10B

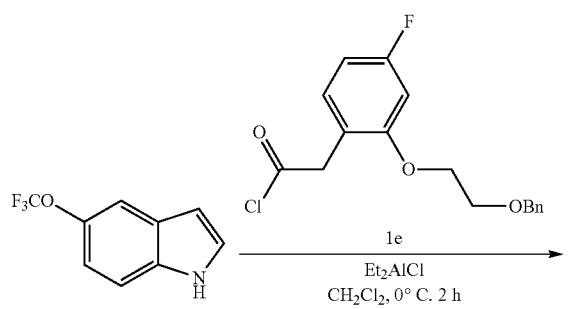

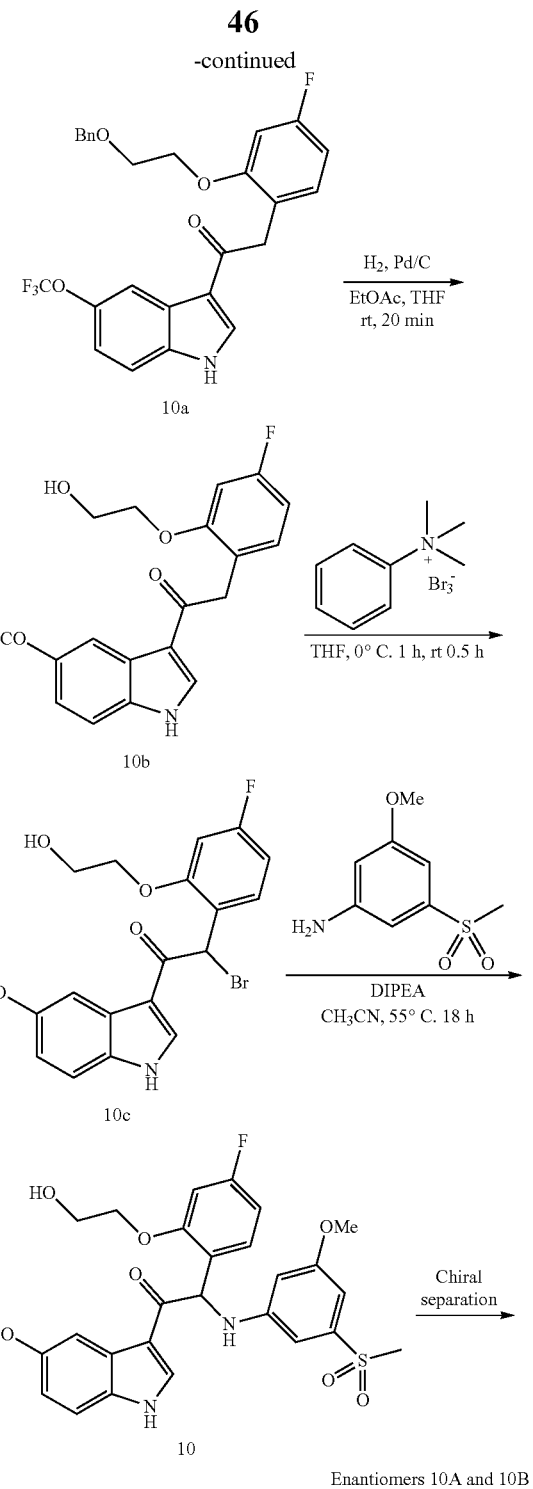

Synthesis of Intermediate 10a

Diethylaluminum chloride 1M in hexane (18.6 mL, 18.6 mmol) was added dropwise, at 0° C. and under $N_2$-flow, to a solution of 5-(trifluoromethoxy)-1H-indole [CAS 262593-63-5] (2.5 g, 12.4 mmol) in $CH_2Cl_2$ (150 mL). After stirring for 15 min at 0° C., a solution of 2-(2-(2-(benzyloxy)ethoxy)-4-fluorophenyl)acetyl chloride 1e (6.02 g, 18.6 mmol) in $CH_2Cl_2$ (100 mL) was added dropwise at 0° C., while keeping the reaction temperature below 7° C. The reaction was stirred at 0° C. for 1.5 h and at room temperature for 2 h. The reaction mixture was cooled to 0° C., and a solution of Rochelle salt [6100-16-9] (7.02 g, 24.9 mmol) in water (7 mL) was added dropwise. The reaction mixture was stirred at 0° C. for 30 minutes and was then allowed to warm to room temperature. THF (150 mL) and $Na_2SO_4$ (25 g) were added, and the mixture was stirred for 1.5 h. The mixture was filtered over Dicalite®. The filter cake was washed with THF (4×150 mL) and the combined filtrates were evaporated under reduced pressure and co-evaporated with $CH_3CN$. The residual oil solidified upon standing overnight. The product was stirred up in $CH_3CN$ (5 mL). The precipitate was filtered off, washed with $CH_3CN$ (3×1 mL), and dried under vacuum at 50° C. to provide a first fraction of 2-(2-(2-(benzyloxy)-ethoxy)-4-fluorophenyl)-1-(5-(trifluoromethoxy)-1H-indol-3-yl)ethanone 10a (1.3 g).

The combined filtrates were evaporated under reduced pressure. The residue (7 g) was purified by flash chromatography (Stationary phase: Biotage® SNAP Ultra silica 100 g, Mobile phase: heptane/EtOAc/EtOH gradient 100/0/0 to 40/45/15). The desired fractions were combined, evaporated under reduced pressure, and co-evaporated with $CH_3CN$ and toluene. The remaining oil was triturated with a mixture of toluene/heptane 1/1 (30 mL). The solids were filtered off, washed 2× with toluene/heptane 1/1, and dried under vacuum at 50° C. to provide a second fraction of intermediate 10a (1.97 g).

Synthesis of Intermediate 10b

A mixture of 2-(2-(2-(benzyloxy)ethoxy)-4-fluorophenyl)-1-(5-(trifluoromethoxy)-1H-indol-3-yl)ethanone 10a (1.97 g, 4.04 mmol) in EtOAc (75 mL) and THF (10 mL) was hydrogenated at room temperature under atmospheric pressure of $H_2$ for 20 min over 10% Pd/C (0.5 g). The mixture was filtered through a pad of Dicalite® and washed with THF. The combined filtrates were concentrated under reduced pressure. The solid residue was stirred up in $CH_2Cl_2$ (3.5 mL). The precipitate was filtered off, washed with $CH_2Cl_2$ (3×1 mL) and dried under vacuum at 45° C. to afford 2-(4-fluoro-2-(2-hydroxyethoxy)phenyl)-1-(5-(trifluoromethoxy)-1H-indol-3-yl)ethanone 10b (1.49 g).

Synthesis of Intermediate 10c

A solution of 2-(4-fluoro-2-(2-hydroxyethoxy)phenyl)-1-(5-(trifluoromethoxy)-1H-indol-3-yl)ethanone 10b (1.49 g, 3.75 mmol) in THF (60 mL) was cooled to 0° C., under a $N_2$ flow. Phenyltrimethylammonium tribromide [CAS 4207-56-1] (1.48 g, 3.94 mmol) was added and the reaction mixture was stirred at 0° C. for 1 h and at room temperature for 30 min. The precipitate was filtered off, wash with THF (2×) and the combined filtrates were evaporated under reduced pressure to give 2-bromo-2-(4-fluoro-2-(2-hydroxyethoxy)phenyl)-1-(5-(trifluoromethoxy)-1H-indol-3-yl)ethanone 10c (1.79 g) which was used without further purification in the next step.

Synthesis of Compound 10 and Chiral Separation of Enantiomers 10A and 10B

2-Bromo-2-(4-fluoro-2-(2-hydroxyethoxy)phenyl)-1-(5-(trifluoromethoxy)-1H-indol-3-yl)ethanone 10c (1.79 g, 3.76 mmol), 3-methoxy-5-(methylsulfonyl)aniline [CAS 62606-02-4] (3.41 g, 17.0 mmol) and diisopropylethylamine (2.92 mL, 17.0 mmol) were dissolved in $CH_3CN$ (90 mL) and the reaction mixture was stirred at 55° C. for 18 h under $N_2$-atmosphere. A solid fraction was removed by filtration, washed with THF (2×) and discarded (unreacted starting material 3-methoxy-5-(methylsulfonyl)-aniline). Water was added to the combined filtrates and the product was extracted with $Et_2O$. The combined organic layers were washed with brine, dried over $MgSO_4$, filtered, and evaporated under reduced pressure. The residue was purified by column chromatography (Stationary phase: Grace Reveleris® silica 80 g, Mobile phase: EtAOc:EtOH (3:1)/heptane gradient 0/100 to 40/60). The product fractions were combined and evaporated under reduced pressure. The residue was further purified via preparative HPLC (Stationary phase: RP XBridge® Prep C18 OBD—10 µm, 50×150 mm, Mobile phase: 0.25% $NH_4HCO_3$ solution in water, $CH_3CN$). The fractions containing product were combined, evaporated under reduced pressure and co-evaporated with MeOH to give racemic 2-(4-fluoro-2-(2-hydroxyethoxy)phenyl)-2-((3-methoxy-5-(methylsulfonyl)phenyl)-amino)-1-(5-(trifluoromethoxy)-1H-indol-3-yl)ethanone (Compound 10, 861 mg). The chiral separation of the enantiomers of Compound 10 (810 mg) was performed via Normal Phase Chiral separation (Stationary phase: Whelk-O1 (R,R), Mobile phase: 80% heptane, 20% ethanol). The fractions containing product were combined and evaporated to provide Enantiomer 10A as the first eluted product and Enantiomer 10B as the second eluted product. Both enantiomers were further purified by column chromatography (Grace Reveleris® silica 12 g, eluent: EtAOc:EtOH (3:1)/heptane gradient 0/100 to 40/60). The product fractions were combined, evaporated under reduced pressure and co-evaporated with MeOH. The residues were solidified by precipitation from a solvent mixture of MeOH and water, filtered off and dried at 50° C. under vacuum to provide Enantiomer 10A (119 mg) and Enantiomer 10B (78 mg).

Enantiomer 10A $^1$H NMR (360 MHz, DMSO-$d_6$) δ ppm 3.08 (s, 3H) 3.72 (s, 3H) 3.85-4.08 (m, 2H) 4.14-4.21 (m, 2H) 5.32 (t, J=5.5 Hz, 1H) 6.37 (d, J=7.7 Hz, 1H) 6.57 (t, J=1.8 Hz, 1H) 6.64 (br s, 1H) 6.69-6.78 (m, 1H) 6.90-6.99 (m, 2H) 7.08 (d, J=7.3 Hz, 1H) 7.21 (br d, J=9.1 Hz, 1H) 7.38 (dd, J=8.8, 7.0 Hz, 1H) 7.56 (d, J=8.4 Hz, 1H) 8.07 (d, J=1.5 Hz, 1H) 8.78 (s, 1H) 12.37 (br s, 1H)

LC/MS (method LC-A): $R_t$ 1.11 min, MH$^+$ 597

$[α]_D^{20}$: −112.2° (c 0.565, DMF)

Chiral SFC (method SFC-E): $R_t$ 2.95 min, MH$^+$ 597, chiral purity 99.8%.

Enantiomer 10B $^1$H NMR (360 MHz, DMSO-$d_6$) δ ppm 3.08 (s, 3H) 3.72 (s, 3H) 3.88-4.07 (m, 2H) 4.14-4.21 (m, 2H) 5.32 (t, J=5.5 Hz, 1H) 6.37 (d, J=7.7 Hz, 1H) 6.56-6.59 (m, 1H) 6.65 (t, J=2.2 Hz, 1H) 6.73 (td, J=8.4, 2.6 Hz, 1H) 6.91-6.98 (m, 2H) 7.08 (d, J=7.7 Hz, 1H) 7.21 (dd, J=9.0, 2.0 Hz, 1H) 7.38 (dd, J=8.8, 7.0 Hz, 1H) 7.56 (d, J=8.8 Hz, 1H) 8.08 (d, J=1.5 Hz, 1H) 8.78 (s, 1H) 12.38 (br s, 1H)

LC/MS (method LC-A): $R_t$ 1.11 min, MH$^+$ 597

$[α]_D^{20}$: +112.1° (c 0.527, DMF)

Chiral SFC (method SFC-E): $R_t$ 2.65 min, MH$^+$ 597, chiral purity 98.2%.

Example 11: Synthesis of 2-(4-chloro-2-(2-hydroxyethoxy)phenyl)-2-((3-methoxy-5-(methylsulfonyl)phenyl)amino)-1-(6-methoxy-5-(trifluoromethoxy)-1H-indol-3-yl)ethanone (Compound 11) and Chiral Separation to Enantiomers 11A and 11B

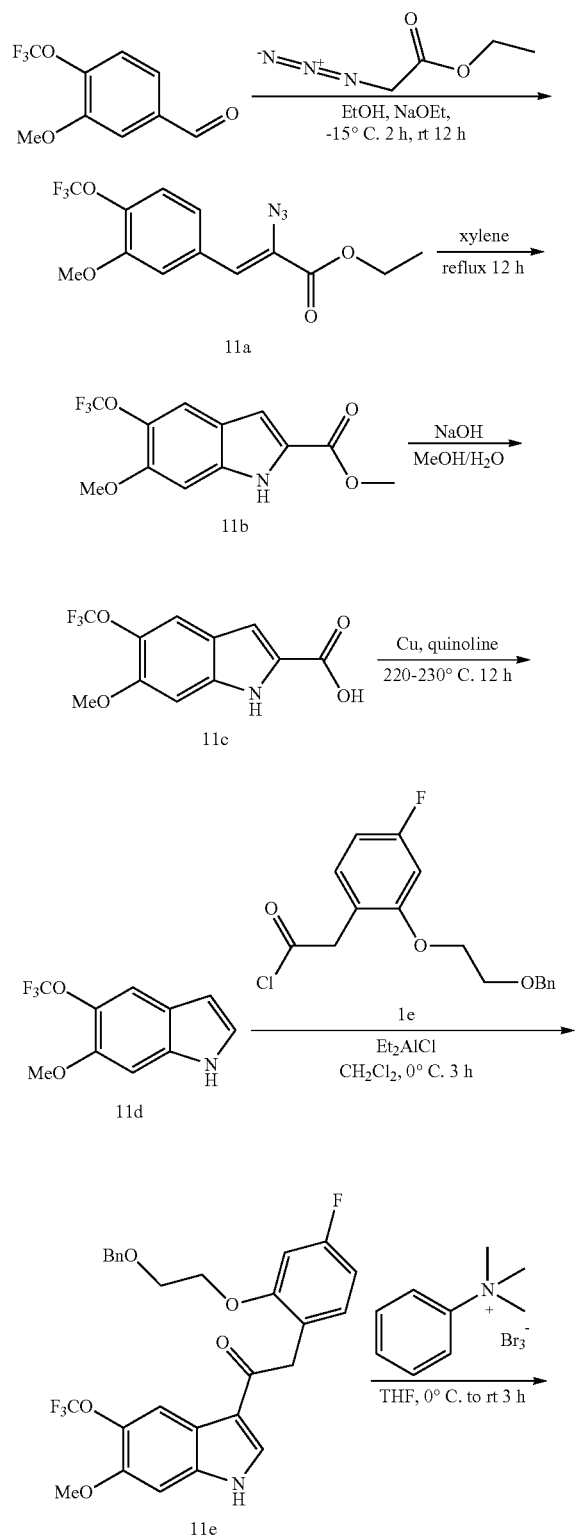

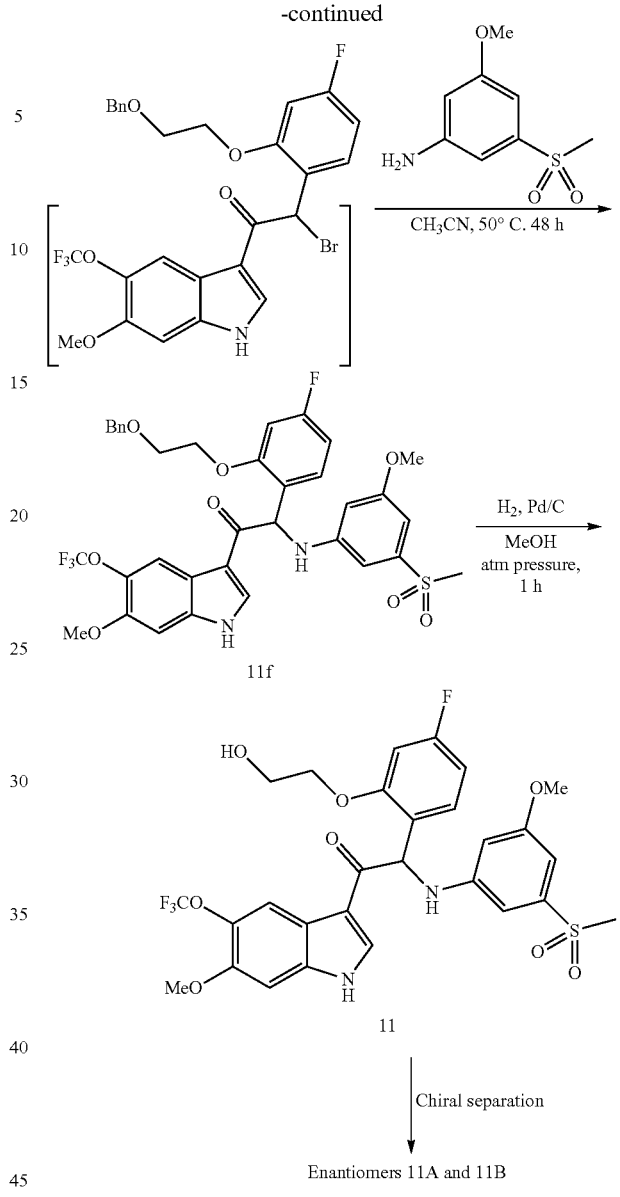

Synthesis of Intermediate 1a

To a cooled (−15° C.) solution of 3-methoxy-4-(trifluoromethoxy)benzaldehyde [CAS 853771-90-1] (50 g, 230 mmol) and ethyl azidoacetate (89 g, 690 mmol) in EtOH (400 mL) was added dropwise, over a period of 2 h, a solution of NaOEt (0.69 mol, prepared from 15.9 g Na and 700 mL of EtOH). The reaction mixture was stirred at room temperature overnight. After cooling on an ice-bath, the reaction was quenched with a saturated $NH_4Cl$ solution (1.2 L), and stirred for 10 min. The precipitate was filtered off, washed with water, and dried to give (Z)-ethyl 2-azido-3-(3-methoxy-4-(trifluoromethoxy)phenyl)acrylate 11a (32 g) as a yellowish solid.

Synthesis of Intermediate 11b

A solution of (Z)-ethyl 2-azido-3-(3-methoxy-4-(trifluoromethoxy)phenyl)acrylate 11a (3 g, 10 mmol) in xylene (40 mL) was heated under reflux overnight. After cooling to room temperature, the solvent was evaporated to dryness. The residue was triturated with hexane (50 mL) and the precipitate was filtered off to afford methyl 6-methoxy-5-(trifluoromethoxy)-1H-indole-2-carboxylate 11 b (yield: 1.4-1.6 g) as a yellow solid.

Synthesis of Intermediate 11c

To a mixture of methyl 6-methoxy-5-(trifluoromethoxy)-1H-indole-2-carboxylate 11b (25 g, 87 mmol) in MeOH/$H_2O$ (2/1, 300 mL) was added NaOH (7 g, 175 mmol) and the mixture was heated under reflux until a clear solution was obtained. After cooling to room temperature, most of the methanol was removed under reduced pressure and the remaining aqueous solution was acidified with conc. HCl to pH 3-4. The product was extracted with EtOAc (2×250 mL). The combined organic layers were washed with brine, dried, and evaporated under reduced pressure to give 6-methoxy-5-(trifluoromethoxy)-1H-indole-2-carboxylic acid 11c (22.7 g) as a grey solid.

Synthesis of Intermediate 11d

A suspension of 6-methoxy-5-(trifluoromethoxy)-1H-indole-2-carboxylic acid 11c (7.5 g, 27 mmol) and Cu (1.22 g, 0.7 equiv.) in quinoline (150 mL) was heated to 220-230° C. under inert atmosphere for 12 h. After cooling to room temperature, the mixture was diluted with methyl tert-butyl ether (MTBE, 400 mL) and washed with a saturated aqueous $NaHSO_4$ solution (2×500 mL). The organic layer was dried over $MgSO_4$, filtered through short pad of silica gel, and evaporated under reduced pressure. The residue was purified by column chromatography to afford 6-methoxy-5-(trifluoromethoxy)-1H-indole 11d (3.75 g) as a yellow solid.

Synthesis of the Intermediate 11e

Diethylaluminium chloride 1M in hexane (7.8 mL, 7.8 mmol) was added dropwise at 0° C. to a solution of 6-methoxy-5-(trifluoromethoxy)-1H-indole (1.2 g, 5.19 mmol) in $CH_2Cl_2$ (25 mL). After 30 min at 0° C., 2-(2-(2-(benzyloxy)ethoxy)-4-fluoro-phenyl)acetyl chloride 1e (1.94 g, 6.0 mmol) in $CH_2Cl_2$ (25 mL) was added dropwise. The reaction was stirred at 0° C. for 3 h. The reaction was carefully quenched at 0° C. with ice and then with water. The layers were separated and the aqueous layer was extracted with $CH_2Cl_2$. The combined organic layers were dried over $MgSO_4$, filtered and the solvent was evaporated under reduced pressure. The residue was purified by flash chromatography on silica gel (15-40 μm, 80 g, eluent: $CH_2Cl_2$). The pure fractions were combined and evaporated to dryness to afford 2-(2-(2-(benzyloxy)ethoxy)-4-fluorophenyl)-1-(6-methoxy-5-(trifluoromethoxy)-1H-indol-3-yl)ethanone 11e (1.6 g).

Synthesis of the Intermediate 11f

Under a $N_2$ flow, at 0° C., a solution of trimethylphenylammonium tribromide (1.1 g, 2.9 mmol) in THF (40 mL) was added dropwise to a solution of 2-(2-(2-(benzyl-oxy)ethoxy)-4-fluorophenyl)-1-(6-methoxy-5-(trifluoromethoxy)-1H-indol-3-yl)-ethanone 11e (1.5 g, 2.9 mmol) in THF (40 mL). The mixture was stirred at 0° C. for 1 h, the cooling bath was removed and stirring was continued at room temperature for 3 h. 3-Methoxy-5-(methylsulfonyl) aniline [CAS 62606-02-04] (1.75 g, 8.7 mmol) in $CH_3CN$ (40 mL) was added and the resulting mixture was stirred for 48 h at 50° C. The mixture was concentrated under reduced pressure. The residue was taken up with EtOAc, washed with water, 1N HCl (3×), and then with water. The organic layer was dried over $MgSO_4$, filtered and the solvent was evaporated under reduced pressure. The residue was purified by flash chromatography on silica gel (15-40 μm, 80 g, eluent: $CH_2Cl_2$). The pure fractions were combined and evaporated to dryness yielding 2-(2-(2-(benzyloxy)ethoxy)-4-fluorophenyl)-2-((3-methoxy-5-(methylsulfonyl)phenyl)amino)-1-(6-methoxy-5-(trifluoromethoxy)-1H-indol-3-yl) ethanone 11f (1 g).

Synthesis of Compound 11 and Chiral Separation into Enantiomers 11A and 11B

A mixture of 2-(2-(2-(benzyloxy)ethoxy)-4-fluorophenyl)-2-((3-methoxy-5-(methyl-sulfonyl)phenyl)amino)-1-(6-methoxy-5-(trifluoromethoxy)-1H-indol-3-yl)ethanone 11f (1 g, 1.39 mmol) in $CH_3OH$ (30 mL) was hydrogenated under atmospheric pressure of $H_2$ for 1 h using Pd/C 10% (300 mg, 0.28 mmol) as the catalyst. The reaction was diluted with $CH_2Cl_2$ and filtered through a pad of Celite®. The filtrate was evaporated under reduced pressure. The residue was purified by flash chromatography on silica gel (15-40 μm, 40 g, eluent: $CH_2Cl_2/CH_3OH$ 99/1). A second purification was performed via reverse phase HPLC (Stationary phase: XBridge®-C18 10 μM, 30×150 mm, Mobile phase: gradient from 50% $NH_4HCO_3$ (0.2%)/50% MeOH to 0% $NH_4HCO_3$ (0.2%)/100% MeOH). The pure fractions were combined and evaporated to dryness to afford, after solidification in diisopropyl ether, 2-(4-fluoro-2-(2-hydroxyethoxy)phenyl)-2-((3-methoxy-5-(methyl-sulfonyl)phenyl) amino)-1-(6-methoxy-5-(trifluoromethoxy)-1H-indol-3-yl) ethanone (compound 11, 170 mg) as a racemic mixture. The enantiomers of Compound 11 (150 mg) were separated via chiral SFC (Stationary phase: Chiralpak® AD-H 5 μm 250×20 mm, Mobile phase: 70% $CO_2$, 30% iPrOH (+0.3% iPrNH$_2$)) yielding 67 mg of the first eluted enantiomer and 70 mg of the second eluted enantiomer. The first eluted enantiomer was solidified from diisopropyl ether/petroleum ether to give 58 mg of Enantiomer 11A. The second eluted enantiomer was solidified from diisopropyl ether/petroleum ether to give 58 mg of Enantiomer 11B.

Compound 11

$^1$H NMR (400 MHz, DMSO-$d_6$) δ ppm 3.07 (s, 3H) 3.71 (s, 3H) 3.86 (s, 3H) 3.88-4.06 (m, 2H) 4.17 (t, J=4.5 Hz, 2H) 5.26 (brs, 1H) 6.33 (d, J=8.1 Hz, 1H) 6.57 (d, J=1.5 Hz, 1H) 6.63 (s, 1H) 6.72 (td, J=8.6, 2.5 Hz, 1H) 6.89-6.97 (m, 2H) 7.01 (d, J=7.6 Hz, 1H) 7.17 (s, 1H) 7.38 (dd, J=8.6, 7.1 Hz, 1H) 8.03 (d, J=1.0 Hz, 1H) 8.61 (s, 1H) 12.14 (br s, 1H)
LC/MS (method LC-C): $R_t$ 2.99 min, MH$^+$ 627

Compound 11A $^1$H NMR (500 MHz, DMSO-$d_6$) δ ppm 3.08 (s, 3H) 3.72 (s, 3H) 3.87 (s, 3H) 3.89-4.08 (m, 2H) 4.16-4.19 (m, 2H) 5.30 (br s, 1H) 6.34 (d, J=7.6 Hz, 1H) 6.57 (s, 1H) 6.63 (br s, 1H) 6.72 (td, J=8.4, 1.9 Hz, 1H) 6.90-6.98 (m, 2H) 7.05 (br d, J=7.9 Hz, 1H) 7.17 (s, 1H) 7.38 (t, J=7.7 Hz, 1H) 8.04 (s, 1H) 8.63 (s, 1H) 12.14 (br s, 1H)
LC/MS (method LC-C): $R_t$ 2.99 min, MH$^+$ 627
$[α]_D^{20}$: −90.3° (c 0.29, DMF)

Chiral SFC (method SFC-F): Rt 2.31 min, MH+ 627, chiral purity 100%.

Compound 11B $^1$H NMR (500 MHz, DMSO-d$_6$) δ ppm 3.08 (s, 3H) 3.72 (s, 3H) 3.87 (s, 3H) 3.89-4.08 (m, 2H) 4.14-4.20 (m, 2H) 5.30 (br s, 1H) 6.34 (d, J=7.6 Hz, 1H) 6.57 (s, 1H) 6.63 (br s, 1H) 6.72 (td, J=8.4, 2.0 Hz, 1H) 6.90-6.99 (m, 2H) 7.05 (d, J=7.6 Hz, 1H) 7.17 (s, 1H) 7.38 (t, J=7.6 Hz, 1H) 8.04 (s, 1H) 8.63 (s, 1H) 12.10 (br s, 1H)

LC/MS (method LC-C): R$_t$ 2.99 min, MH$^+$ 627

[α]$_D^{20}$: +95.4° (C 0.26, DMF)

Chiral SFC (method SFC-F): R$_t$ 3.29 min, MH$^+$ 627, chiral purity 100%.

Example 12: Synthesis of 2-(4-fluoro-2-(2-hydroxyethoxy)phenyl)-2-((3-methoxy-5-(methylsulfonyl)phenyl)amino)-1-(7-methyl-5-(trifluoromethoxy)-1H-indol-3-yl)-ethanone (Compound 12) and Chiral Separation to Enantiomers 12A and 12B

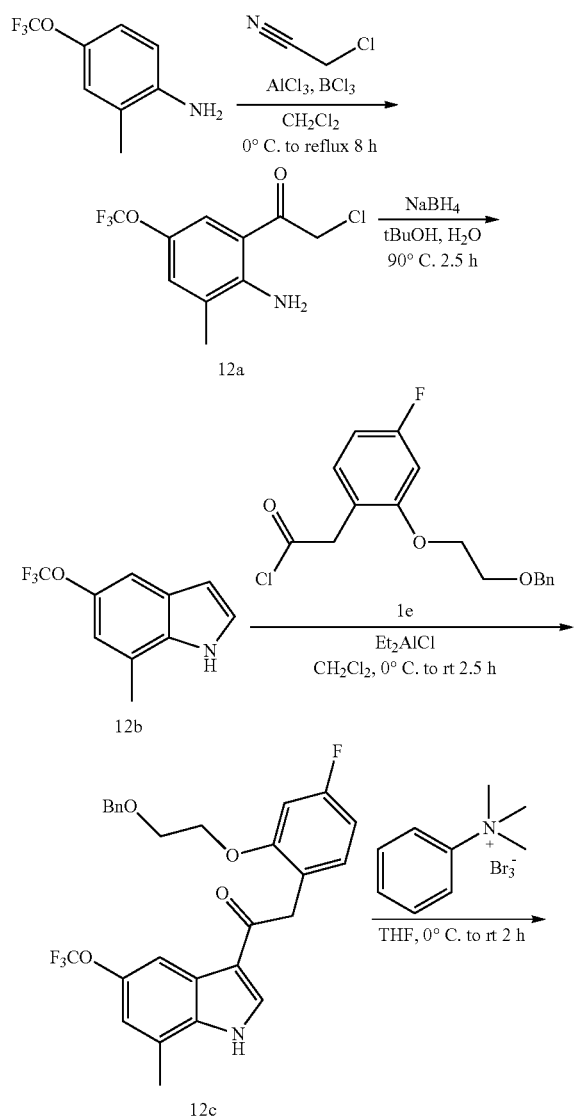

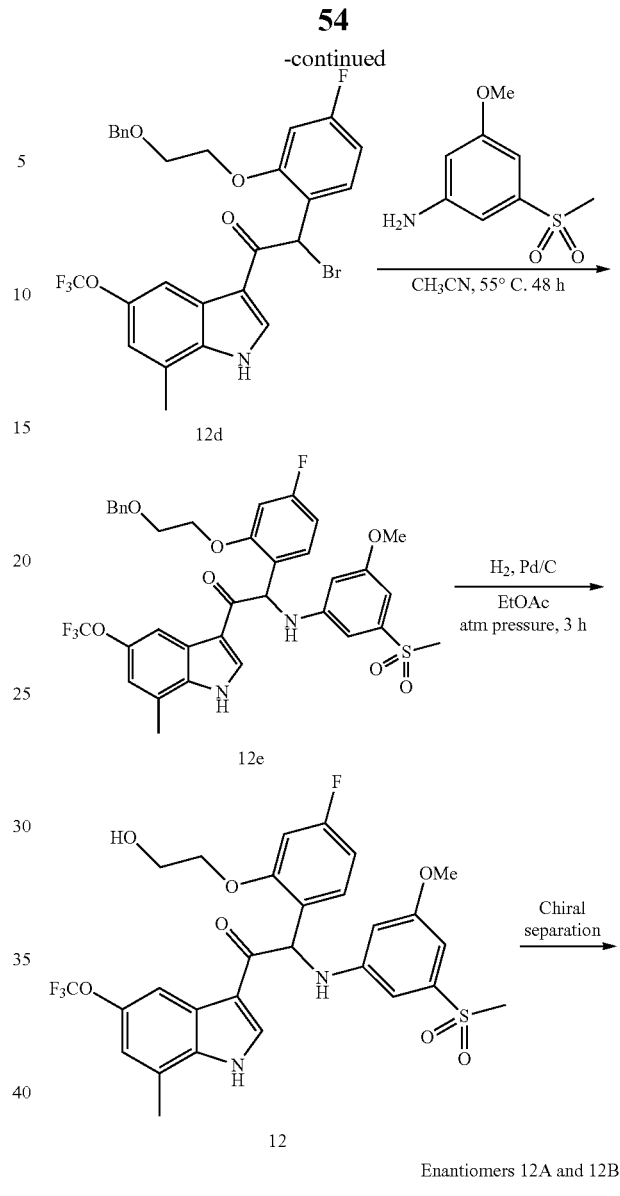

Synthesis of Intermediate 12a

A mixture of boron(III) chloride 1M in CH$_2$Cl$_2$ (25.5 mL, 25.5 mmol) and aluminum(III) chloride (3.40 g, 25.5 mmol) was diluted with CH$_2$Cl$_2$ (20 mL) and cooled on an ice-bath under N$_2$-atmosphere. A solution of 2-methyl-4-(trifluoromethoxy)aniline [CAS 86256-59-9] (4.88 g, 25.5 mmol) and chloroacetonitrile (3.24 mL, 51.0 mmol) in CH$_2$Cl$_2$ (7.5 mL) was added dropwise. After addition, the ice-bath was removed and the mixture was heated under reflux for 8 h. The mixture was cooled again to 0° C. using an ice-bath. 2N HCl (75 mL) was added dropwise, causing heavy precipitation. The resulting suspension was heated under reflux for 90 min, and cooled to room temperature. The solids were removed by filtration. The filter cake was washed with CH$_2$Cl$_2$ (4×). The filtrates were combined and the phases were separated. The organic layer was isolated, washed with an aqueous NaHCO$_3$ solution, dried over MgSO$_4$, filtered and evaporated under reduced pressure. The residue was purified by flash chromatography (Stationary phase: Biotage® SNAP Ultra Silica 100 g, Mobile phase: heptane/

CH₂Cl₂ gradient 100/0 to 0/100). The desired fractions were combined and concentrated to a residual volume of 30 mL. The precipitate was filtered off, washed with heptane and CH₂Cl₂, and dried under vacuum at 50° C. to provide 1-(2-amino-3-methyl-5-(trifluoromethoxy)phenyl)-2-chloroethanone 12a (1.37 g). The filtrate was concentrated under reduced pressure. The solid residue was stirred up in a mixture of heptane (20 mL) and diisopropyl ether (3 mL), filtered off, washed with heptane (3×) and dried under vacuum at 50° C. to provide a second fraction of 12a (0.24 g).

Synthesis of Intermediate 12b

Sodium borohydride (326 mg, 8.61 mmol) was added to a stirred solution of 1-(2-amino-3-methyl-5-(trifluoromethoxy)phenyl)-2-chloroethanone 12a (1.92 g, 7.17 mmol) in tert-butanol (50 mL) and water (5 mL). The reaction mixture was stirred at room temperature for 30 min and at 90° C. for 2.5 h. Water (50 mL) was added and the product was extracted with diethyl ether (2×). The combined organic layers were washed with brine, dried over MgSO₄, filtered and evaporated under reduced pressure. The residue was purified by flash chromatography (Stationary phase: Biotage® SNAP Ultra silica 25 g, Mobile phase: heptane/EtOAc gradient 100/0 to 20/80). The desired fractions were combined, concentrated under reduced pressure, co-evaporated with heptane and dried under vacuum at 50° C. to provide 7-methyl-5-(trifluoromethoxy)-1H-indole 12b (1.2 g).

Synthesis of the Intermediate 12c

Diethylaluminium chloride 1M in hexane (16.5 mL, 16.5 mmol) was added dropwise at 0° C. to a solution of 7-methyl-5-(trifluoromethoxy)-1H-indole 12b (2.36 g, 11.0 mmol) in CH₂Cl₂ (150 mL). After stirring for 25 min at 0° C., a solution of 2-(2-(2-(benzyloxy)ethoxy)-4-fluorophenyl)acetyl chloride 1e (5.3 g, 16.4 mmol) in CH₂Cl₂ (75 mL) was added dropwise, while keeping the reaction temperature below 5° C. The reaction was stirred at 0° C. for 1 h and at room temperature for 2.5 h. The reaction was cooled to 0° C. and a solution of Rochelle salt (6.20 g, 22.0 mmol) in water (6 mL) was added dropwise. The reaction mixture was stirred for 30 min at 0° C. The ice-bath was removed and the mixture was allowed to reach room temperature. THF (200 mL) and Na₂SO₄ (25 g) were added and the mixture was stirred overnight. The reaction mixture was filtered over Dicalite® and the filter cake was washed with THF (4×150 mL). The filtrates were combined and evaporated under reduced pressure. The solid residue was stirred up in a solvent mixture of DIPE (25 mL) and EtOAc (2 mL). The solids were filtered off, washed with DIPE (3×) and dried at 50° C. under vacuum to give 2-(2-(2-(benzyloxy)ethoxy)-4-fluorophenyl)-1-(7-methyl-5-(trifluoromethoxy)-1H-indol-3-yl)ethanone 12c (4.3 g).

Synthesis of the Intermediate 12d

Under N₂ flow, at 0° C., phenyltrimethylammonium tribromide (3.39 g, 9.0 mmol) was added to a stirred solution of 2-(2-(2-(benzyloxy)ethoxy)-4-fluorophenyl)-1-(7-methyl-5-(trifluoromethoxy)-1H-indol-3-yl)ethanone 12c (4.3 g, 8.6 mmol) in THF (40 mL). The mixture was stirred at 0° C. for 1 h and at room temperature for 2 h. The solids were removed by filtration, and the filter was rinsed with THF (2×). The combined filtrates were evaporated under reduced pressure to give 2-(2-(2-(benzyloxy)ethoxy)-4-fluorophenyl)-2-bromo-1-(7-methyl-5-(trifluoromethoxy)-1H-indol-3-yl)ethanone 12d (6.9 g), which was used without further purification in the next step.

Synthesis of Intermediate 12e

Under N₂-atmosphere, a mixture of 2-(2-(2-(benzyloxy)ethoxy)-4-fluorophenyl)-2-bromo-1-(7-methyl-5-(trifluoromethoxy)-1H-indol-3-yl)ethanone 12d (6.73 g, 11.6 mmol), 3-methoxy-5-(methylsulfonyl)aniline [CAS 62606-02-04] (4.67 g, 23.2 mmol) and diisopropyethylamine (4.00 mL, 23.2 mmol) in CH₃CN (90 mL) was stirred for 48 h at 55° C. Water (125 mL) was added and the product was extracted with Et₂O (2×). The combined organic layers were washed with brine, dried over MgSO₄, filtered and the solvent was evaporated under reduced pressure. The residue was stirred up in CH₂Cl₂, resulting in the precipitation of unreacted starting material 3-methoxy-5-(methylsulfonyl)aniline. The solids were removed by filtration and the filtrate was evaporated under reduced pressure. The residue was purified by flash chromatography (Stationary phase: Grace Reveleris® silica 80 g, mobile phase: heptane/EtOAc/EtOH gradient 100/0/0 to 40/45/15). The pure product fractions were combined and evaporated to dryness yielding 2-(2-(2-(benzyloxy)ethoxy)-4-fluorophenyl)-2-((3-methoxy-5-(methyl-sulfonyl)phenyl)amino)-1-(7-methyl-5-(trifluoromethoxy)-1H-indol-3-yl)ethanone 12e (4.37 g).

Synthesis of Compound 12 and Chiral Separation into Enantiomers 12A and 12B

A mixture of 2-(2-(2-(benzyloxy)ethoxy)-4-fluorophenyl)-2-((3-methoxy-5-(methyl-sulfonyl)phenyl)amino)-1-(7-methyl-5-(trifluoromethoxy)-1H-indol-3-yl)ethanone 12e (4.37 g, 5.11 mmol) in EtOAc was hydrogenated at room temperature under atmospheric pressure of H₂ for 3 h using Pd/C 10% (500 mg) as the catalyst. The reaction was filtered through a pad of Dicalite® and the filter cake was washed with plenty of THF. The volatiles were evaporated under reduced pressure. The residue was stirred up in CH₂Cl₂/EtOAc (90/10) during 30 min. The solids were filtered off and dried under vacuum at 50° C. overnight to give a racemic 2-(4-fluoro-2-(2-hydroxyethoxy)phenyl)-2-((3-methoxy-5-(methylsulfonyl)phenyl)amino)-1-(7-methyl-5-(trifluoromethoxy)-1H-indol-3-yl)ethanone (Compound 12, 2.02 g, purity by LC/MS: 95%). A fraction of Compound 12 (505 mg) was further purified by preparative HPLC (Stationary phase: RP XBridge® Prep C18 OBD—10 μm, 30×150 mm, Mobile phase: 0.25% NH₄HCO₃ solution in water, MeOH). The product fractions were combined, evaporated under reduced pressure and co-evaporated with MeOH. The residue was solidified from a solution of MeOH by the slow addition of water. The precipitate was filtered off and dried at 50° C. under vacuum to provide pure Compound 12 (300 mg).

The enantiomers of Compound 12 (1569 mg) were separated via Chiral SFC (Stationary phase: Daicel Chiralpak® IA Mobile phase: isocratic 75% CO₂, 20% dichloormethaan+0.2% isopropylamine, 5% methanol+0.2% isopropylamine). The product fractions were combined and evaporated under reduced pressure. The first eluted enantiomer was further purified by flash chromatography (Stationary phase: Grace Reveleris® Silica 40 g, Mobile phase: heptane/EtOAc/EtOH gradient 100/0/0 to 40/45/15). The desired fractions were combined and concentrated to a residual volume of ~15 mL. The mixture was left standing for 30 minutes. The solids were filtered off, washed 3× with heptane/EtOAC 4/1, and dried under vacuum at 45° C. to provide Enantiomer 12A (324 mg). The second eluted enantiomer was further purified by flash chromatography (Stationary phase: Grace Reveleris® Silica 40 g, Mobile phase: heptane/EtOAc/EtOH gradient 100/0/0 to 40/45/15). The desired fractions were combined and concentrated to a residual volume of ~10 mL. The mixture was left standing for 18 h. The solids were filtered off, washed 3× with heptane/EtOAc 4/1, and dried under vacuum at 50° C. to provide Enantiomer 12B (295 mg).

Compound 12

$^1$H NMR (600 MHz, DMSO-$d_6$) δ ppm 2.52 (s, 3H) 3.06 (s, 3H) 3.74 (s, 3H) 3.93-4.05 (m, 2H) 4.19 (t, J=4.8 Hz, 2H) 5.07 (br t, J=5.3 Hz, 1H) 6.37 (d, J=7.8 Hz, 1H) 6.59 (t, J=1.8 Hz, 1H) 6.65 (t, J=2.1 Hz, 1H) 6.70 (td, J=8.4, 2.4 Hz, 1H) 6.89 (d, J=7.8 Hz, 1H) 6.90-6.95 (m, 2H) 7.01 (br s, 1H) 7.40 (dd, J=8.7, 6.9 Hz, 1H) 7.93 (brs, 1H) 8.63 (s, 1H) 12.10-12.32 (m, 1H)

LC/MS (method LC-A): $R_t$ 1.17 min, MH$^+$611

Compound 12A $^1$H NMR (400 MHz, DMSO-$d_6$) δ ppm 2.51 (s, 3H) 3.08 (s, 3H) 3.73 (s, 3H) 3.91-4.08 (m, 2H) 4.18 (t, J=4.6 Hz, 2H) 5.29 (t, J=5.7 Hz, 1H) 6.40 (d, J=7.7 Hz, 1H) 6.58 (t, J=1.9 Hz, 1H) 6.66 (t, J=2.3 Hz, 1H) 6.72 (td, J=8.5, 2.4 Hz, 1H) 6.91-6.98 (m, 2H) 7.00-7.06 (m, 2H) 7.38 (dd, J=8.6, 6.8 Hz, 1H) 7.92 (br s, 1H) 8.70 (d, J=3.3 Hz, 1H) 12.37 (d, J=2.9 Hz, 1H)

LC/MS (method LC-A): $R_t$ 1.16 min, MH$^+$ 611

$[α]_D^{20}$: +77.9° (c 0.425, DMF)

Chiral SFC (method SFC-E): $R_t$ 2.65 min, MH$^+$ 611, chiral purity 91.1%.

Compound 12B $^1$H NMR (400 MHz, DMSO-$d_6$) δ ppm 2.51 (s, 3H) 3.08 (s, 3H) 3.72 (s, 3H) 3.90-4.07 (m, 2H) 4.18 (t, J=4.6 Hz, 2H) 5.29 (t, J=5.7 Hz, 1H) 6.40 (d, J=7.7 Hz, 1H) 6.58 (t, J=1.9 Hz, 1H) 6.66 (t, J=2.1 Hz, 1H) 6.72 (td, J=8.5, 2.4 Hz, 1H) 6.89-6.98 (m, 2H) 6.99-7.08 (m, 2H) 7.38 (dd, J=8.6, 6.8 Hz, 1H) 7.92 (br s, 1H) 8.70 (s, 1H) 12.37 (br s, 1H)

LC/MS (method LC-A): $R_t$ 1.15 min, MH$^+$611

$[α]_D^{20}$: −81.4° (c 0.435, DMF)

Chiral SFC (method SFC-E): $R_t$ 3.01 min, MH$^+$ 611, chiral purity 92.5%.

Antiviral Activity of the Compounds of the Invention
DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 μM-0.000064 μM or 2.5 μM-0.0000064 μM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 μL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 μL of virus suspension was added to all the wells containing test compound and to the wells assigned as virus control. In parallel, 15 μL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 μL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | $EC_{50}$ (μM) | N | $CC_{50}$ (μM) | N | SI | N |
| --- | --- | --- | --- | --- | --- | --- |
| 1 | 0.0018 | 4 | 7.6 | 5 | 3520 | 4 |
| 1A | 0.00078 | 2 | 8.6 | 2 | 9210 | 2 |
| 1B | 0.085 | 4 | 13 | 4 | 149 | 4 |
| 2 | 0.00081 | 4 | 6.2 | 4 | 7600 | 4 |
| 2A | 0.00032 | 6 | 4.9 | 6 | 16800 | 6 |

TABLE 1-continued

EC$_{50}$, CC$_{50}$, and SI for the compounds of the invention in the DENV-2 antiviral assay

| compound# | EC$_{50}$ (µM) | N | CC$_{50}$ (µM) | N | SI | N |
|---|---|---|---|---|---|---|
| 2B | 0.021 | 4 | 12 | 4 | 589 | 4 |
| 3 | 0.0012 | 4 | 5.1 | 4 | 4360 | 4 |
| 3A | 0.00040 | 6 | 4.0 | 6 | 8380 | 6 |
| 3B | 0.029 | 4 | 11 | 4 | 366 | 4 |
| 4 | 0.00037 | 4 | 3.5 | 5 | 8960 | 4 |
| 4A | 0.011 | 4 | 11 | 4 | 1020 | 4 |
| 4B | 0.00020 | 4 | 3.8 | 4 | >16800 | 4 |
| 5 | 0.0010 | 4 | 6.9 | 4 | 6760 | 4 |
| 5A | 0.00051 | 5 | 3.4 | 5 | 6320 | 5 |
| 5B | 0.016 | 4 | 11 | 4 | 670 | 4 |
| 6 | 0.0014 | 4 | 5.8 | 5 | 4220 | 4 |
| 6A | 0.00047 | 5 | 5.6 | 5 | 8410 | 5 |
| 6B | 0.16 | 4 | 13 | 4 | 80 | 4 |
| 7A | 0.00054 | 3 | 3.1 | 4 | 6080 | 3 |
| 7B | 0.036 | 3 | 8.0 | 3 | 224 | 3 |
| 8 | 0.0023 | 3 | 6.9 | 3 | 3050 | 3 |
| 8A | 0.0011 | 3 | 3.4 | 3 | 3620 | 3 |
| 8B | 0.048 | 3 | 8.2 | 3 | 170 | 3 |
| 9A | 0.00039 | 4 | 3.2 | 7 | 6210 | 4 |
| 9B | 0.051 | 3 | 13 | 3 | 253 | 3 |
| 10A | 0.020 | 3 | 12 | 3 | 597 | 3 |
| 10B | 0.00012 | 3 | 2.6 | 3 | 21200 | 3 |
| 11 | 0.00048 | 3 | 9.0 | 4 | 18400 | 3 |
| 11A | 0.019 | 3 | 12 | 3 | 613 | 3 |
| 11B | 0.00020 | 5 | 2.4 | 6 | 24900 | 5 |
| 12 | 0.00022 | 4 | 3.7 | 4 | 16900 | 3 |
| 12A | 0.000099 | 3 | 2.2 | 3 | 22100 | 3 |
| 12B | 0.0012 | 3 | 9.9 | 3 | 8540 | 3 |

Tetravalent Reverse Transcriptase Quantitative-PCR (RT-qPCR) Assay: Protocol A.

The antiviral activity of the compounds of the invention was tested against DENV-1 strain TC974#666 (NCPV), DENV-2 strain 16681, DENV-3 strain H87 (NCPV) and DENV-4 strains H241 (NCPV) and EDEN (SG/06K2270DK1/2005; GenBank accession number QG398256) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound results in a shift of Cp's for the 3'UTR gene. On the other hand, if a test compound is toxic to the cells, a similar effect on β-actin expression will be observed. The comparative ΔΔCp method is used to calculate EC$_{50}$, which is based on the relative gene expression of the target gene (3'UTR) normalized with the cellular housekeeping gene (β-actin). In addition, CC$_{50}$ values are determined based on the Cp values acquired for the housekeeping gene β-actin.

TABLE 2

Primers and probes used for the real-time, quantitative RT-PCR.

| Primer/probe | Target | Sequence[a, b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | FAM-5'-AAGGACTAG-*ZEN*-AGGTTAGAGGAGACCCCCC-3'-*IABkFQ* |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | HEX-5'-TTCCGCTGC-*ZEN*-CCTGAGGCTCTC-3'-*IABkFQ* |

[a] Reporter dyes (FAM, HEX) and quenchers (ZEN and IABkFQ) elements are indicated in bold and italics.
[b] The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 µL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 µM-0.000064 µM or 2.5 µM-0.0000064 µM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% CO$_2$) until the next day. Dengue viruses serotype-1, 2, 3 and 4 were diluted in order to obtain a Cp of ~22-24 in the assay. Therefore, 25 µL of virus suspension, was added to all the wells containing test compound and to the wells assigned as virus control. In parallel, 25 µL of culture medium was added to the cell controls. Next, the plates were incubated for 3 days in a fully humidified incubator (37° C., 5% CO$_2$). After 3 days, the supernatant was removed from the wells and the cells were washed twice with ice-cold PBS (−100 µL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 µL/well was dispensed in a 96-well plate. After addition of 5 µL of the cell lysates, a five minute denaturation step at 75° C. was performed (table 3B). Afterwards, 7.43 µL of mix B was added (table 3C) and the reverse transcription step was initiated (table 3D) to generate cDNA.

Finally, a RT-qPCR mix was prepared, mix C (table 4A), and 22.02 µL/well was dispensed in 96-well LightCycler qPCR plates to which 3 µL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 5-8).

TABLE 3 cDNA synthesis using Mix A, denaturation, Mix B and reverse transcription.

A
Mix A

| Plates | 8 | | | | |
|---|---|---|---|---|---|
| Samples | 828 | | | Reaction Vol. (µl) | 20 |
| | | Concentration | | Volume for (µl) | |
| Mix Item | Unit | Stock | Final | 1 sample | x samples |
| Milli-Q $H_2O$ | | | | 7.27 | 6019.56 |
| R3utr425 | µM | 20 | 0.27 | 0.15 | 124.20 |
| Ractin876 | µM | 20 | 0.27 | 0.15 | 124.20 |
| | | Volume mix/well (µl) | | 7.57 | |
| | | Cell lysates | | 5.00 | |

B
Denaturation step:

| Step | Temp | Time |
|---|---|---|
| Denaturation | 75° C. | 5' |
| Hold | 4° C. | hold |

C
Mix B

| Samples | 864 | | | | |
|---|---|---|---|---|---|
| | | Concentration | | Volume for (µl) | |
| Mix Item | Unit | Stock | Final | 1 sample | x samples |
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/µl | 40.00 | 1.00 | 0.50 | 432.0 |
| Expand RT | U/µl | 50.00 | 0.33 | 0.13 | 112.3 |
| | | Total Volume Mix (µl) | | 7.43 | |

D
Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A
Mix C

| Samples | 833 | | | Reaction Vol. (µl) | 25 |
|---|---|---|---|---|---|
| | | Concentration | | Volume for (µl) | |
| Mix Item | Unit | Stock | Final | 1 sample | x samples |
| $H_2O$ PCR grade Roche | | | | 7.74 | 6447.42 |
| Roche 2xMM mix | X | 2 | 1 | 12.50 | 10412.50 |
| F3utr258 | µM | 20 | 0.3 | 0.38 | 316.54 |
| R3utr425 | µM | 20 | 0.3 | 0.38 | 316.54 |
| P3utr343 | µM | 20 | 0.1 | 0.13 | 108.29 |

TABLE 4-continued qPCR mix and protocol.

| Factin743 | µM | 20 | 0.3 | 0.38 | 316.54 |
|---|---|---|---|---|---|
| Ractin876 | µM | 20 | 0.3 | 0.38 | 316.54 |
| Pactin773 | µM | 20 | 0.1 | 0.13 | 108.29 |
| | Volume Mix/Tube (µl) | | 22.02 | | |
| | cDNA | | 3.00 | | |

B
Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

$EC_{50}$, $CC_{50}$, and SI for the compounds against serotype 1 in the RT-qPCR assays Protocol A
RT-qPCR serotype 1 TC974#666

| compound# | $EC_{50}$ (µM) | N | $CC_{50}$ (µM) | N | SI | N |
|---|---|---|---|---|---|---|
| 1A | 0.0085 | 3 | 6.4 | 3 | 755 | 3 |
| 2A | 0.0028 | 4 | 4.8 | 3 | 1960 | 3 |
| 3A | 0.0033 | 4 | >2.5 | 3 | >1180 | 3 |
| 4B | 0.0033 | 3 | >2.5 | 3 | >836 | 3 |
| 5A | 0.0041 | 4 | >2.5 | 4 | >862 | 4 |
| 6A | 0.0035 | 6 | 4.8 | 5 | 1140 | 5 |
| 7A | 0.0013 | 3 | >2.4 | 3 | >2220 | 3 |
| 8A | 0.0023 | 3 | >2.5 | 3 | >1410 | 3 |
| 9A | 0.0014 | 3 | >2.5 | 3 | >3350 | 3 |
| 10B | 0.00020 | 3 | >2.5 | 3 | >21400 | 3 |
| 11B | 0.00060 | 3 | >2.5 | 3 | >5380 | 3 |
| 12A | 0.00020 | 3 | >1.0 | 3 | >6740 | 3 |

N = the number of independent experiments in which the compounds were tested.

TABLE 6

$EC_{50}$, $CC_{50}$, and SI for the compounds against serotype 2 in the RT-qPCR assays Protocol A
RT-qPCR serotype 2 16681

| compound# | $EC_{50}$ (µM) | N | $CC_{50}$ (µM) | N | SI | N |
|---|---|---|---|---|---|---|
| 1A | 0.0011 | 3 | 6.6 | 3 | 5790 | 3 |
| 2A | 0.00040 | 5 | 5.1 | 6 | 11100 | 5 |
| 3A | 0.00043 | 5 | >2.4 | 5 | >5560 | 5 |
| 4B | 0.00021 | 4 | 3.8 | 5 | >12700 | 4 |
| 5A | 0.00071 | 5 | 3.9 | 5 | 5370 | 5 |
| 6A | 0.00084 | 6 | 5.2 | 7 | 6320 | 6 |
| 7A | 0.00077 | 4 | 3.2 | 3 | 5870 | 3 |
| 8A | 0.0014 | 4 | 3.5 | 4 | 2160 | 4 |
| 9A | 0.00061 | 4 | >2.4 | 4 | >4010 | 4 |
| 10B | 0.000057 | 3 | >2.5 | 3 | >100553 | 3 |
| 11B | 0.00014 | 4 | >2.5 | 4 | >43200 | 4 |
| 12A | 0.000075 | 3 | >1.0 | 3 | >20500 | 3 |

N = the number of independent experiments in which the compounds were tested.

TABLE 7

EC$_{50}$, CC$_{50}$, and SI for the compounds against serotype 3 in the RT-qPCR assays

| | Protocol A RT-qPCR serotype 3 H87 | | | | | |
|---|---|---|---|---|---|---|
| compound# | EC$_{50}$ (μM) | N | CC$_{50}$ (μM) | N | SI | N |
| 1A | 0.068 | 3 | 5.8 | 2 | 94 | 2 |
| 2A | 0.048 | 4 | 4.0 | 3 | 64 | 3 |
| 3A | 0.045 | 4 | >2.5 | 2 | >80 | 2 |
| 4B | 0.055 | 3 | >2.5 | 2 | >76 | 2 |
| 5A | 0.061 | 4 | >2.0 | 3 | >36 | 3 |
| 6A | 0.043 | 6 | 1.5 | 3 | 37 | 3 |
| 7A | 0.020 | 3 | 2.2 | 2 | 126 | 2 |
| 8A | 0.036 | 3 | >2.5 | 3 | >75 | 3 |
| 9A | 0.016 | 3 | >2.5 | 3 | >206 | 3 |
| 10B | 0.0021 | 3 | >2.5 | 3 | >1630 | 3 |
| 11B | 0.0073 | 3 | >2.5 | 3 | >502 | 3 |
| 12A | 0.0032 | 3 | >1.0 | 3 | >463 | 3 |

N = the number of independent experiments in which the compounds were tested.

TABLE 8

EC$_{50}$, CC$_{50}$, and SI for the compounds against serotype 4 in the RT-qPCR assays.

| | Protocol A RT-qPCR serotype 4 H241 | | | | | |
|---|---|---|---|---|---|---|
| compound# | EC$_{50}$ (μM) | N | CC$_{50}$ (μM) | N | SI | N |
| 1A | 0.29 | 4 | 3.0 | 2 | 9.7 | 2 |
| 2A | 0.17 | 6 | 3.3 | 5 | 19 | 5 |
| 3A | 0.19 | 5 | 2.9 | 3 | 15 | 3 |
| 4B | 0.14 | 5 | 2.1 | 4 | 15 | 4 |
| 5A | 0.18 | 5 | 2.6 | 5 | >18 | 5 |
| 6A | 0.11 | 5 | 3.3 | 3 | 28 | 3 |
| 7A | 0.12 | 4 | 1.9 | 3 | 17 | 3 |
| 8A | 0.22 | 3 | 1.1 | 3 | 4.9 | 3 |
| 9A | 0.11 | 4 | >2.2 | 3 | >22 | 3 |
| 10B | 0.012 | 3 | 1.8 | 3 | 89 | 3 |
| 11B | 0.034 | 3 | >2.5 | 3 | >102 | 3 |
| 12A | 0.014 | 3 | 0.69 | 2 | 47 | 2 |

| | Protocol A RT-qPCR serotype 4 EDEN | | | | | |
|---|---|---|---|---|---|---|
| compound# | EC$_{50}$ (μM) | N | CC$_{50}$ (μM) | N | SI | N |
| 1A | 0.0036 | 1 | 5.0 | 1 | 1386 | 1 |
| 2A | 0.0023 | 4 | 2.8 | 4 | 1178 | 4 |
| 3A | 0.0051 | 4 | >2.5 | 3 | >1194 | 3 |
| 4B | 0.0032 | 3 | >2.5 | 3 | >1231 | 3 |
| 5A | 0.0037 | 4 | >2.5 | 4 | >1250 | 4 |
| 6A | 0.0034 | 5 | 3.7 | 4 | 1048 | 4 |

N = the number of independent experiments in which the compounds were tested.

The invention claimed is:

1. A compound of formula (I)

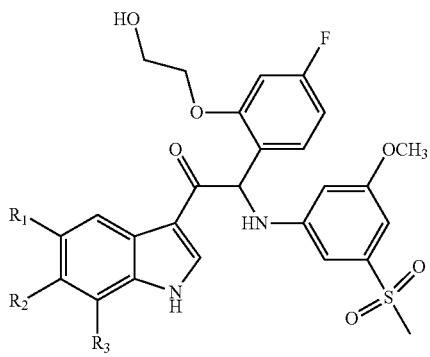

or a stereo-isomeric form, a pharmaceutically acceptable salt, solvate or polymorph thereof comprising a mono- or di-substituted indole group; wherein said formula (I) is selected from the group consisting of:

$R_1$ is H, $R_2$ is F or Cl and $R_3$ is H or $CH_3$;

$R_1$ is F, $R_2$ is F and $R_3$ is H;

$R_1$ is $CH_3$, $R_2$ is $OCH_3$ and $R_3$ is H;

$R_1$ is $CH_3$, $R_2$ is F and $R_3$ is H;

$R_1$ is $CH_3$, $R_2$ is H and $R_3$ is F;

$R_1$ is Cl, $R_2$ is H and $R_3$ is $CH_3$;

$R_1$ is $OCF_3$, $R_2$ is H or $OCH_3$ and $R_3$ is H; and $R_1$ is $OCF_3$, $R_2$ is H and $R_3$ is $CH_3$.

2. The compound of claim 1 wherein said formula (I) is selected from the group:

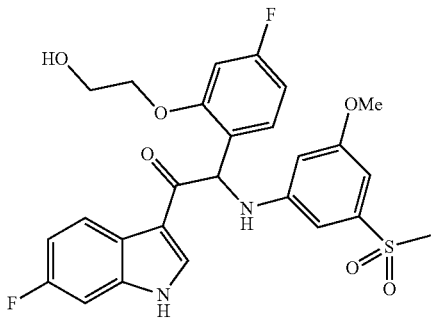

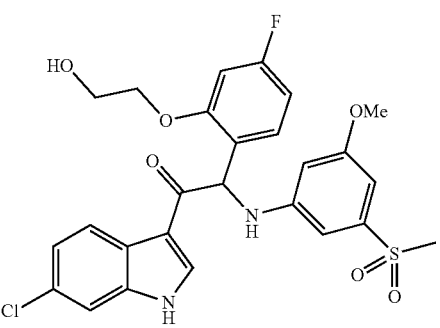

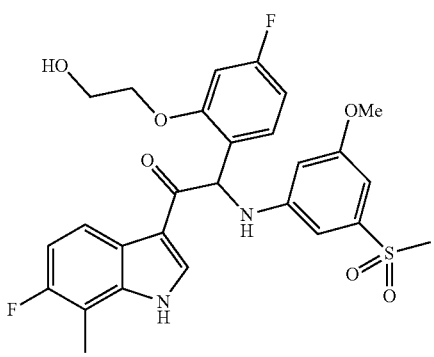

-continued

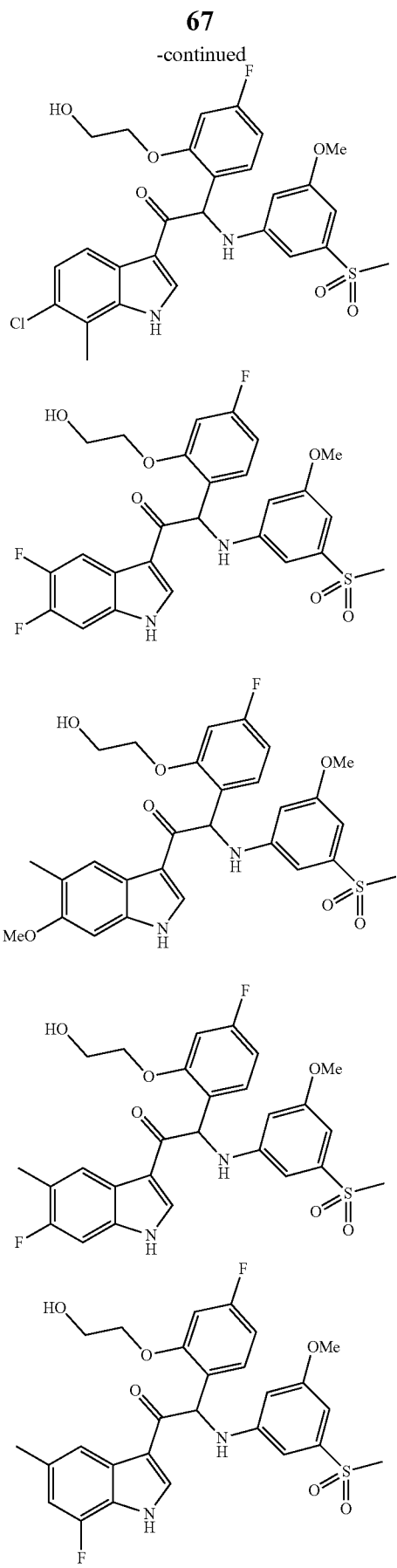

-continued

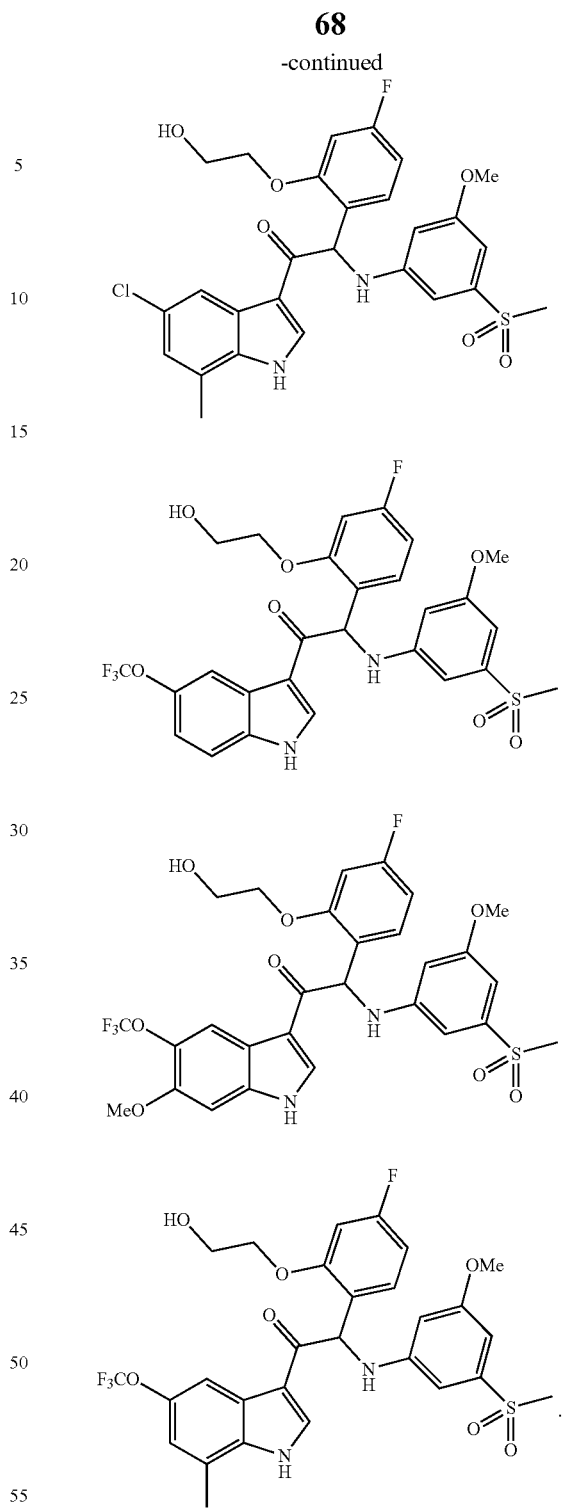

3. A pharmaceutical composition comprising a compound of claim 1 and one or more pharmaceutically acceptable excipients, diluents or carriers.

4. A method of treating a dengue infection comprising administering an effective amount of the pharmaceutical composition of claim 3 to a patient in need thereof.

5. The method of claim 4, wherein said method further comprises administering another antiviral agent to said patient.

6. The compound of claim 2, which is:
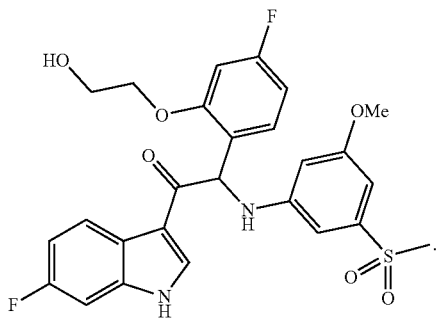 [SMILES: COc1cc(NC(C(=O)c2c[nH]c3cc(F)ccc23)c2ccc(F)cc2OCCO)cc(S(C)(=O)=O)c1]
7. The compound of claim 2, which is:
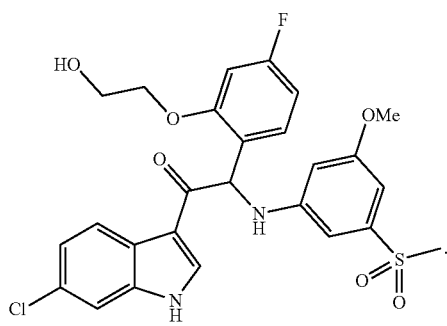 [SMILES: COc1cc(NC(C(=O)c2c[nH]c3cc(Cl)ccc23)c2ccc(F)cc2OCCO)cc(S(C)(=O)=O)c1]
8. The compound of claim 2, which is:
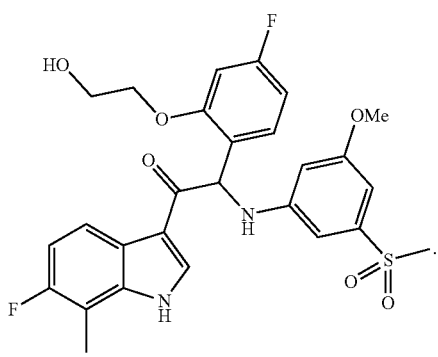 [SMILES: COc1cc(NC(C(=O)c2c[nH]c3c(C)c(F)ccc23)c2ccc(F)cc2OCCO)cc(S(C)(=O)=O)c1]
9. The compound of claim 2, which is:
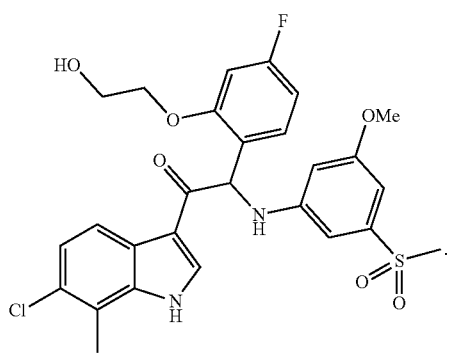 [SMILES: COc1cc(NC(C(=O)c2c[nH]c3c(C)c(Cl)ccc23)c2ccc(F)cc2OCCO)cc(S(C)(=O)=O)c1]
10. The compound of claim 2, which is:
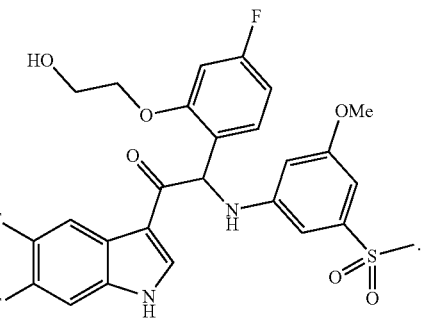
11. The compound of claim 2, which is:
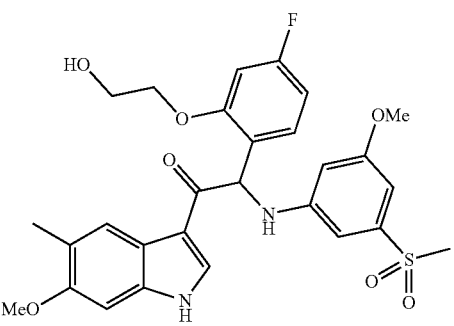
12. The compound of claim 2, which is:
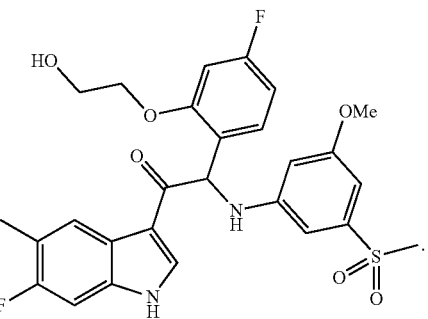
13. The compound of claim 2, which is:
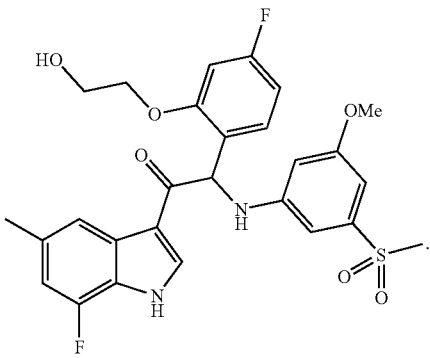

14. The compound of claim 2, which is:
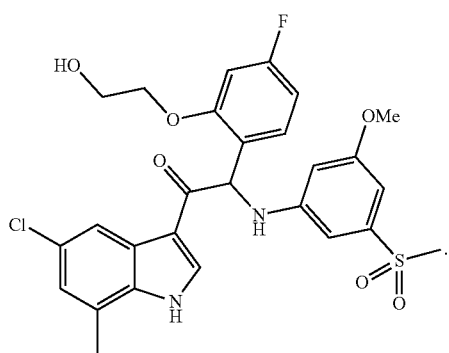 [SMILES: COc1cc(NC(C(=O)c2c[nH]c3c(C)cc(Cl)cc23)c2ccc(F)cc2OCCO)cc(S(C)(=O)=O)c1]
15. The compound of claim 2, which is:
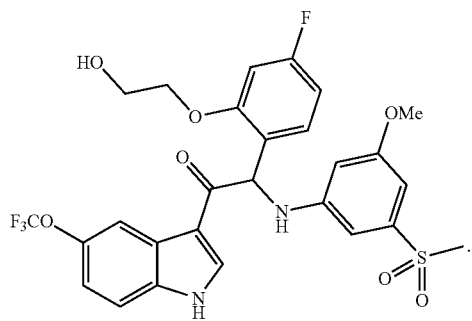 [SMILES: COc1cc(NC(C(=O)c2c[nH]c3ccc(OC(F)(F)F)cc23)c2ccc(F)cc2OCCO)cc(S(C)(=O)=O)c1]
16. The compound of claim 2, which is:
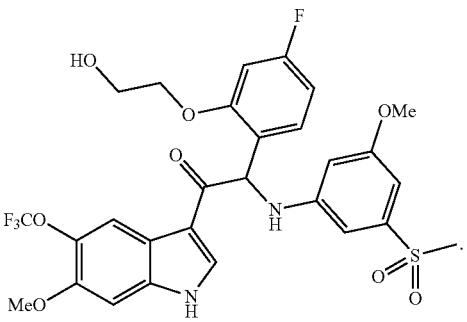 [SMILES: COc1cc(NC(C(=O)c2c[nH]c3cc(OC)c(OC(F)(F)F)cc23)c2ccc(F)cc2OCCO)cc(S(C)(=O)=O)c1]
17. The compound of claim 2, which is:
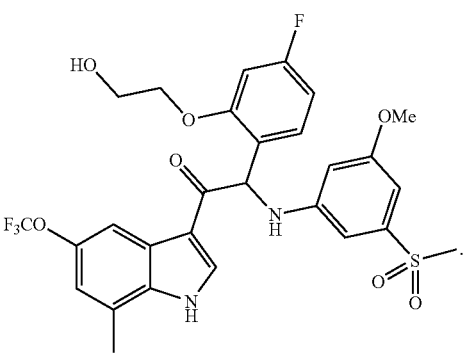 [SMILES: COc1cc(NC(C(=O)c2c[nH]c3c(C)cc(OC(F)(F)F)cc23)c2ccc(F)cc2OCCO)cc(S(C)(=O)=O)c1]
* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Dengue virus

<400> SEQUENCE: 1
cggttagagg agacccctc                                                 19

<210> SEQ ID NO 2
<211> LENGTH: 21
<212> TYPE: DNA
<213> ORGANISM: Dengue virus

<400> SEQUENCE: 2
gagacagcag gatctctggt c                                              21

<210> SEQ ID NO 3
<211> LENGTH: 28
<212> TYPE: DNA
<213> ORGANISM: Dengue virus

<400> SEQUENCE: 3
aaggactaga ggttagagga gacccccc                                       28

<210> SEQ ID NO 4
<211> LENGTH: 18

```
<212> TYPE: DNA
<213> ORGANISM: Dengue virus

<400> SEQUENCE: 4
ggccaggtca tcaccatt                                              18

<210> SEQ ID NO 5
<211> LENGTH: 21
<212> TYPE: DNA
<213> ORGANISM: Dengue virus

<400> SEQUENCE: 5
atgtccacgt cacacttcat g                                          21

<210> SEQ ID NO 6
<211> LENGTH: 21
<212> TYPE: DNA
<213> ORGANISM: Dengue virus

<400> SEQUENCE: 6
ttccgctgcc ctgaggctct c                                          21
```